US012286669B2

(12) United States Patent
Buse et al.

(10) Patent No.: US 12,286,669 B2
(45) Date of Patent: *Apr. 29, 2025

(54) APPARATUS FOR APPLYING THERMAL ENERGY TO A RECEPTACLE AND DETECTING AN EMISSION SIGNAL FROM THE RECEPTACLE

(71) Applicant: Gen-Probe Incorporated, San Diego, CA (US)

(72) Inventors: David Buse, San Diego, CA (US); David Howard Combs, San Diego, CA (US); Norbert D. Hagen, Carlsbad, CA (US); David Opalsky, San Diego, CA (US); Bruce Richardson, Los Gatos, CA (US); Anita Prasad, Los Gatos, CA (US); Keith Moravick, Los Gatos, CA (US); Tyler Moore, Los Gatos, CA (US); Byron J. Knight, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 452 days.

This patent is subject to a terminal disclaimer.

(21) Appl. No.: 17/027,363

(22) Filed: Sep. 21, 2020

(65) Prior Publication Data
US 2021/0062245 A1 Mar. 4, 2021

Related U.S. Application Data

(63) Continuation of application No. 17/025,735, filed on Sep. 18, 2020, now Pat. No. 11,230,733, which is a
(Continued)

(51) Int. Cl.
*C12Q 1/686* (2018.01)
*B01L 7/00* (2006.01)
(Continued)

(52) U.S. Cl.
CPC ............... *C12Q 1/686* (2013.01); *B01L 7/52* (2013.01); *G01N 21/6452* (2013.01); *B01L 9/06* (2013.01);
(Continued)

(58) Field of Classification Search
None
See application file for complete search history.

(56) References Cited

U.S. PATENT DOCUMENTS 5,250,261 A    10/1993   Porte
5,346,672 A *   9/1994   Stapleton .................. B01L 7/52
                                                               422/947

(Continued)

FOREIGN PATENT DOCUMENTS

CN      1876800 A     12/2006
CN    101241075 A     8/2008
(Continued)

OTHER PUBLICATIONS

PCT International Search Report, International Application No. PCT/US13/052966, Feb. 7, 2014.
(Continued)

*Primary Examiner* — Matthew D Krcha
(74) *Attorney, Agent, or Firm* — Richard Wydeven, Rothwell, Figg, Ernst & Manbeck, P.C.; Charles B. Cappellari

(57) ABSTRACT

An apparatus for performing nucleic acid amplification reactions includes a thermally-conductive receptacle holder that includes multiple receptacle wells. Each well can receive a receptacle and has a through-hole extending from an inner surface of the well to an outer surface of the holder. The apparatus includes multiple optical fibers, and each optical fiber has a first end in optical communication with an associated well and a second end in optical communication (Continued)

with an excitation signal source and/or an emission signal detector. The first end of each optical fiber is moveable with respect to the through-hole. A cover is movable between an open position and a closed position relative to the receptacle holder, and the first end of each optical fiber moves with respect to the through-hole of the associated well as the cover moves to the open or closed position or when the cover moves into or out of contact with any receptacles within the wells.

24 Claims, 32 Drawing Sheets

Related U.S. Application Data continuation of application No. 16/434,910, filed on Jun. 7, 2019, now Pat. No. 10,961,572, which is a continuation of application No. 13/956,022, filed on Jul. 31, 2013, now Pat. No. 10,494,668.

(60) Provisional application No. 61/783,952, filed on Mar. 14, 2013, provisional application No. 61/677,976, filed on Jul. 31, 2012.

(51) Int. Cl.
   *G01N 21/64*     (2006.01)
   *B01L 9/06*      (2006.01)

(52) U.S. Cl.
   CPC ... *B01L 2200/141* (2013.01); *B01L 2200/142* (2013.01); *B01L 2300/042* (2013.01); *B01L 2300/0654* (2013.01); *B01L 2300/0829* (2013.01); *B01L 2300/0851* (2013.01); *B01L 2300/1822* (2013.01); *G01N 2021/6482* (2013.01); *G01N 2021/6484* (2013.01)

(56) References Cited

U.S. PATENT DOCUMENTS

| | | | |
|---|---|---|---|
| 5,473,437 A | 12/1995 | Blumenfeld et al. | |
| 5,604,130 A | 2/1997 | Warner et al. | |
| 5,804,144 A * | 9/1998 | Tervamaki | B01L 3/0217 |
| | | | 73/864.18 |
| 5,935,524 A | 8/1999 | Bass et al. | |
| 6,134,000 A | 10/2000 | Schmid et al. | |
| 6,143,496 A | 11/2000 | Brown et al. | |
| 6,144,448 A * | 11/2000 | Mitoma | B01L 7/52 |
| | | | 435/808 |
| 6,197,572 B1 | 3/2001 | Schneebeli | |
| 8,017,380 B2 | 9/2011 | Moriwaki et al. | |
| 10,494,668 B2 | 12/2019 | Buse et al. | |
| 2001/0019826 A1 | 9/2001 | Ammann | |
| 2005/0206895 A1* | 9/2005 | Salmelainen | G01N 21/6408 |
| | | | 356/318 |
| 2005/0282270 A1 | 12/2005 | Shin et al. | |
| 2006/0030035 A1 | 2/2006 | Joseph et al. | |
| 2006/0246576 A1 | 11/2006 | Shirazi | |
| 2007/0077646 A1* | 4/2007 | Okamoto | B01L 7/00 |
| | | | 435/305.3 |
| 2008/0022808 A1* | 1/2008 | Owen | G01N 35/026 |
| | | | 81/3.2 |
| 2009/0149351 A1 | 6/2009 | Tajima | |
| 2010/0081583 A1 | 4/2010 | Shirazi | |
| 2010/0136632 A1 | 6/2010 | Lipscomb et al. | |
| 2011/0312102 A1* | 12/2011 | Jo | G01J 3/0216 |
| | | | 436/164 |
| 2021/0062705 A1 | 3/2021 | Kennedy et al. | |

FOREIGN PATENT DOCUMENTS

| | | | | |
|---|---|---|---|---|
| CN | 101302473 A | 11/2008 | | |
| CN | 101952412 A | 1/2011 | | |
| CN | 102329725 A | 1/2012 | | |
| CN | 102892508 A | 1/2013 | | |
| EP | 0580362 A1 | 1/1994 | | |
| EP | 0583066 A1 | 2/1994 | | |
| EP | 0571033 B1 | 3/1997 | | |
| EP | 0953379 A1 | 11/1999 | | |
| EP | 1930078 A1 | 6/2008 | | |
| JP | H06-034536 A | 2/1994 | | |
| JP | H06-181744 A | 7/1994 | | |
| JP | H07-132236 A | 5/1995 | | |
| JP | 2000-051684 A | 2/2000 | | |
| JP | 2002-513936 A | 5/2002 | | |
| JP | 2010-508813 A | 3/2010 | | |
| WO | 1999057561 A | 11/1999 | | |
| WO | 2004105947 A2 | 12/2004 | | |
| WO | 2008-057375 A2 | 5/2008 | | |
| WO | 20090012924 A1 | 1/2009 | | |
| WO | 2009030908 A3 | 3/2009 | | |
| WO | 2011124918 A1 | 10/2011 | | |
| WO | WO-2012012779 A2 * | 1/2012 | ............. | B01L 3/021 |

OTHER PUBLICATIONS

PCT Written Opinion, International Application No. PCT/US13/052966, Feb. 7, 2014.
PCT International Preliminary Report on Patentability, International Application No. PCT/US13/052966, Feb. 12, 2015.
IPA Examination Report No. 1, Australian Patent Application No. 2013202793, Feb. 28, 2014.
IPA Notice of Acceptance, Australian Patent Application No. 2013202793, Sep. 4, 2014.
IPA Examination Report No. 1, Australian Application No. 2017210511, Jul. 19, 2018.
IPA Examination Report No. 1, Australian Application No. 2019206128, Mar. 6, 2020.
IPA Notice of Acceptance, Australian Application No. 2019206128, Feb. 23, 2021.
IPA Examination Report No. 1, Australian Application No. 2020233639, Jan. 29, 2021.
IPA Notice of Acceptance, Australian Application No. 2020233639, Feb. 26, 2021.
CNIPA Search Report, Chinese Patent Application No. 201380046526.7, Dec. 7, 2015.
CNIPA First Office Action, Chinese Patent Application No. 201380046526.7, Dec. 23, 2015.
CNIPA Second Office Action, Chinese Patent Application No. 201380046526.7, Sep. 14, 2016.
CNIPA Third Office Action, Chinese Patent Application No. 201380046526.7, Feb. 28, 2017.
CNIPA Search Report, Chinese Patent Application No. 201380046526.7, Jun. 29, 2017.
CNIPA Search Report, Chinese Patent Application No. 202010576517.0, Sep. 20, 2021.
CNIPA First Office Action, Chinese Patent Application No. 202010576517.0, Sep. 28, 2021.
CNIPA Second Office Action, Chinese Patent Application No. 202010576517.0, May 9, 2022.
CNIPA Search Report, Chinese Patent Application No. 202010576517.0, May 1, 2021.
EPO Extended European Search Report, European Application No. 13826240.7, Feb. 29, 2016.
EPO Communication Pursuant to Article 94(3) EPC, European Application No. 13826240.7, Feb. 15, 2017.
EPO Communication under Rule 71(3) EPC, European Application No. 13826240.7, May 7, 2018.
EPO Communication under Rule 71(3) EPC, European Application No. 13826240.7, Sep. 24, 2018.
EPO Partial European Search Report, European Application No. 19161986.5, Aug. 8, 2019.
EPO Extended European Search Report, European Application No. 19161986.5, Sep. 25, 2019.
EPO Communication under Rule 71(3) EPC, European Application No. 19161986.5, Oct. 29, 2020.

(56) References Cited

OTHER PUBLICATIONS

EPO Extended European Search Report, European Application No. 19161987.3, Aug. 7, 2019.
EPO Communication under Rule 71(3) EPC, European Application No. 19161987.3, Nov. 2, 2020.
EPO Extended European Search Report, European Application No. 20197378.1, Dec. 11, 2020.
JPO Official Action No. 1, Japanese Patent Application No. 2015-525551, Apr. 24, 2017.
JPO Official Action No. 2, Japanese Patent Application No. 2015-525551, Dec. 6, 2017.
JPO Final Official Action, Japanese Patent Application No. 2015-525551, Oct. 30, 2018.
JPO Notice of Allowance, Japanese Patent Application No. 2015-525551, May 13, 2019.
JPO Notice of Allowance, Japanese Patent Application No. 2019-148745, Jul. 30, 2020.
JPO Notice of Allowance, Japanese Patent Application No. 2019-148746, Aug. 2, 2020.
USPTO Non-Final Rejection, U.S. Appl. No. 17/027,433, filed Sep. 13, 2022.
CNIPA Search Report, Chinese Patent Application No. 201710826817.8, Mar. 20, 2019.
CNIPA Office Action, Chinese Patent Application No. 201710826817.8, Mar. 28, 2019.
CNIPA Office Action, Chinese Patent Application No. 201710826817.8, Jan. 22, 2020.
EPO Communication pursuant to Article 94(3) EPC, European Application No. 20197378.1, Apr. 4, 2023.
USPTO Interview Summary, U.S. Appl. No. 17/027,433, filed Dec. 7, 2022.
USPTO Notice of Allowance, U.S. Appl. No. 17/027,433, filed Feb. 15, 2023.

\* cited by examiner

APPARATUS FOR APPLYING THERMAL ENERGY TO A RECEPTACLE AND DETECTING AN EMISSION SIGNAL FROM THE RECEPTACLE

CROSS REFERENCE TO RELATED APPLICATIONS

This application is a continuation application claiming the benefit under 35 U.S.C. § 120 of the filing date of non-provisional patent application Ser. No. 17/025,735 filed Sep. 18, 2020, now U.S. Pat. No. 11,230,733, which is a continuation application claiming the benefit under 35 U.S.C. § 120 of the filing date of non-provisional patent application Ser. No. 16/434,910 filed Jun. 7, 2019, now U.S. Pat. No. 10,961,572, which is a continuation application claiming the benefit under 35 U.S.C. § 120 of the filing date of non-provisional patent application Ser. No. 13/956,022 filed Jul. 31, 2013, now U.S. Pat. No. 10,494,668, which claims the benefit under 35 U.S.C. § 119(e) of the filing date of provisional patent application Serial Nos. 61/677,976, filed Jul. 31, 2012, and 61/783,952, filed Mar. 14, 2013, the respective disclosures of which are incorporated herein by reference.

BACKGROUND

The present disclosure relates generally to a system and apparatus for automated heating and/or cooling of samples.

BACKGROUND INFORMATION

Automated molecular assay instrumentation offers numerous advantages, however most automated instruments suffer from a limited set of assay capabilities. These limited capabilities complicate or inhibit parallel processing of multiple assays and, as a result, reduce sample throughput and flexibility in assay choices. This is particularly true for assays requiring incubation of some sort, such as the temperature cycling necessary for polymerase chain reaction (PCR) based assays. In PCR instruments a thermocycler is included that is capable of cycling the temperature of many samples, such as a batch of samples held within a 96-well microtiter plate. This assay format requires the preparation of the entire batch of samples prior to subjecting them to an initial temperature cycle. For example, the first sample that is fully prepared for temperature cycling must wait until the last sample is prepared prior to temperature cycling. In the case of a 96-well plate, this wait time can be substantial, thus slowing the throughput of the instrument. In addition, since all samples are subject to the same temperature profile and cycling parameters, the types of assays that can be run in parallel are limited. Different assays often must be run in completely different thermocycler units or await availability of the thermocycler from a prior batch of samples. This too inhibits the ability to provide rapid assay results.

The present disclosure addresses these and other needs in the art.

All documents referred to herein, or the indicated portions, are hereby incorporated by reference herein. No document, however, is admitted to be prior art to the claimed subject matter.

SUMMARY

The present disclosure relates to a system and apparatus for altering the temperature of at least one receptacle holder that is adapted for use in an automated instrument capable of performing biochemical assays.

In an aspect of the present disclosure, there is provided an apparatus that includes one or more receptacle holders made of a heat-conducting material. Each receptacle holder includes a plurality of receptacle wells, each receptacle well being configured to receive a receptacle therein; a plurality of through-holes, each through-hole extending from an inner surface of one of the receptacle wells to an outer surface of the receptacle holder; a plurality of optical fibers, each optical fiber having first and second ends, wherein the first end is in optical communication with one of the receptacle wells, and the second end is in optical communication with at least one of an excitation signal source and an emission signal detector, the first end of each optical fiber being disposed outside, within, or extending through, a corresponding through-hole in each receptacle well, and wherein the first end of each optical fiber is moveable or fixedly disposed within one of the through-holes relative to the surface of the receptacle well; and one or more thermal elements positioned proximal to the receptacle holder for altering a temperature or temperatures of the receptacle holder. In certain embodiments, the apparatus includes a cover movable between an opened position and a closed position relative to the receptacle holder, wherein one or more receptacles disposed within one or more of the receptacle wells are seated or secured into the receptacle well by the cover when the cover is moved into the closed position. In an exemplary embodiment, the first end of each optical fiber moves within its corresponding through-hole when (1) the cover is moved to the closed and/or opened position, or (2) a receptacle is present in the receptacle well and the cover is moved to the closed and/or open position. In a variety of these embodiments, the apparatus does not include a cover. Also, in a variety of these embodiments, when these apparatuses are comprised in a system, one or more of these apparatuses do/does not include a cover. One or more receptacle transport mechanism(s) are often included in such systems to transport receptacles to the receptacles wells, deposit the receptacles in the receptacles wells, optionally ensure each receptacle is securely seated in its respective receptacle well by using, for example, physical contact, and removing each receptacle from its respective receptacle well. More than one receptacle transport mechanism may be utilized in such embodiments to effect one or more of these steps.

In various embodiments, the thermal element is positioned proximal to a side surface of the receptacle holder and provides thermal energy through the receptacle holder to each of the plurality of receptacle wells. The thermal energy may be uniform. In frequent embodiments, the apparatus further includes one or more support(s), each positioned proximal to a side surface of one or more of the receptacle holders, and the thermal element is positioned between the support and the receptacle holder. One or more thermistors may be disposed in contact with the receptacle holder. In a variety of embodiments, the one or more thermistors and/or associated wiring thereof are disposed within a channel formed in the receptacle holder. In certain embodiments, the apparatus further includes one or more closed-ended channels formed on opposing sides of a receptacle well of the receptacle holder, each having one of the thermistors disposed therein.

In certain embodiments the apparatus further includes one or more cross-braces positioned to provide compressive force between the receptacle holder and the support. In other embodiments, the apparatus further includes one or more bodies having a low thermal conductivity, each connected directly or indirectly with a linker, positioned to provide compressive force between the receptacle holder and the support. In various embodiments, the support of the apparatus is a heat sink or the support is provided in thermal communication with a heat sink. The apparatus may include a first controller electrically connected to the thermal element to cycle the temperature of the thermal element and may include one or more motors electrically connected to the first controller disposed in moveable communication with the cover, if present. In various embodiments, if present, the cover may include a rigid element and one or more flexible extensions, wherein the flexible extensions are attached to, and extend laterally away from, the rigid element to apply a force when the cover is in the closed position to at least a portion of one or more receptacles when present within the receptacle wells.

In exemplary embodiments, the apparatus further includes a stripper plate in movable association with the receptacle holder for removing a receptacle from a receptacle transport mechanism that delivers a receptacle to the receptacle holder. The stripper plate may be moveable relative to the receptacle well into unlocked and locked positions, wherein the unlocked position permits access of a receptacle to the receptacle well, and wherein the locked position inhibits removal of the receptacle from the receptacle well without inhibiting access to the receptacle by the receptacle transport mechanism.

In another aspect, the disclosure provides a system that includes one or more apparatus of the present disclosure. In various embodiments, each of the one or more apparatus is in independent thermal communication with a single heat sink. The thermal element corresponding to each receptacle holder within the system may be independently controllable to only alter the temperature of its corresponding receptacle holder. In frequent embodiments, the system includes one or more controllers electrically connected to the thermal elements, and to one or more motors disposed in moveable communication with a cover corresponding to each receptacle holder. In various embodiments, the system does not include a cover. The system may include at least ten receptacle wells and at least ten corresponding optical fibers, wherein the second ends of all of the optical fibers are in optical communication with one or more excitation signal sources and/or one or more emission signal detectors. In frequent embodiments, the system is disposed in a single housing.

In another aspect, the disclosure provides a method of conducting an automated, random-access incubation process. In one exemplary embodiment, the method includes the automated steps of transferring a first set of receptacles to a first receptacle holder and subjecting the contents of the first set of receptacles to a first incubation process, and during the first incubation process, transferring a second set of receptacles to a second receptacle holder and subjecting the contents of the second set of receptacles to a second incubation process. In another exemplary embodiment, the first and second receptacle holders are components of the apparatus as disclosed herein. Each of the first and second sets of receptacles may be sealed to prevent contamination and/or evaporation. In various exemplary embodiments, the first and second receptacle holders are each in thermal communication with a single temperature cycling apparatus, as described herein.

In frequent embodiments, the method further includes, during the second incubation process, beginning a third of three or more independent processes comprising: transferring a third or higher set of receptacles to a third or higher receptacle holder and subjecting the contents of the third or higher set of receptacles to a third or higher incubation process, wherein the transfer of each successive set of receptacles is begun prior to completion of the incubation process for each immediately preceding set of receptacles. The transfer of the first and second sets of receptacles may be effected by a receptacle transport mechanism. As described herein, each set of receptacles may be removed from its respective receptacle holder prior to completion of the next successive incubation process.

In another aspect, the disclosure provides a method of establishing optical communication between a receptacle and an excitation signal source and/or an emission signal detector within a housing of an apparatus. The method includes the automated steps of providing a receptacle to a well of a receptacle holder comprised of a heat-conducting material, applying a first force to the receptacle, thereby seating the receptacle within the well, and either of (1) while the force is being applied to the receptacle, effecting movement of an end of an optical fiber toward and into contact with the seated receptacle, or (2) while the force is being applied to the receptacle, the receptacle applies a second force to an end of an optical fiber disposed within the well such that the end of the optical fiber moves within the well in a direction opposite from the direction of the applied second force.

In various embodiments, the receptacle is in contact with the optical fiber during or after step (a), and while the force is being applied to the receptacle, the receptacle contacts and applies force to the end of the optical fiber disposed within the well such that the end of the optical fiber moves within the well in a direction opposite from the direction of the applied force. The end of or an area proximal to the end of the optical fiber may be connected, directly or indirectly, with a resilient element to the receptacle holder such that the resilient element compresses when force is applied to the receptacle.

In yet another exemplary aspect, the disclosure provides an apparatus that includes a housing, a plurality of receptacle holders contained within the housing, each comprised of a heat-conducting material, wherein each receptacle holder comprises a plurality of receptacle wells, one or more thermal elements positioned proximal to each receptacle holder for altering a temperature or temperatures of the plurality of receptacle wells. In various embodiments, the apparatus further includes a plurality of covers, each disposed in moveable association with a receptacle holder, wherein a first controller controls movement of each cover between an opened and a closed position. When at least one receptacle is present in the plurality of receptacle wells it is secured within the receptacle wells by the cover when in the closed position. When the cover is in the opened position, a receptacle transport mechanism can access the plurality of receptacle wells to introduce or remove a receptacle. In addition, each cover can move between the opened and closed positions together with, or independently of, one or more other covers. In other various embodiments, the apparatus does not include a cover.

In various embodiments, the apparatus further includes an optical fiber associated with each receptacle well such that optical communication is established between an interior of each receptacle well and an excitation signal source and/or an emission signal detector. The apparatus may further include one or more receptacles in the plurality of receptacle wells, and optical communication is established between each receptacle and the excitation signal source and/or the emission signal detector by the optical fibers. In frequent embodiments, the apparatus further includes a stripper plate in moveable association with each receptacle holder for removing a receptacle from the receptacle transport mechanism.

In various embodiments, the support of the apparatus is a heat sink or the support is provided in thermal communication with a heat sink. The apparatus may include a first controller electrically connected to the thermal element to cycle the temperature of the thermal element and may include one or more motors electrically connected to the first controller disposed in moveable communication with the cover, if present. In various embodiments, if present, the cover may include a rigid element and one or more flexible extensions, wherein the flexible extensions are attached to, and extend laterally away from, the rigid element to apply a force when the cover is in the closed position to at least a portion of one or more receptacles when present within the receptacle wells.

In yet another exemplary aspect, the disclosure provides an apparatus that includes a housing, a plurality of receptacle holders contained within the housing, each comprised of a heat-conducting material, wherein each receptacle holder comprising a plurality of receptacle wells, and one or more thermal elements electrically connected to a first controller, and positioned proximal to each receptacle holder for altering a temperature or temperatures of the plurality of receptacle wells. In various embodiments, the apparatus may further include a plurality of covers, each being movable between a first non-engagement position and a second engagement position with respect to a receptacle holder, wherein each cover comprises a series of flexible extensions, wherein each individual flexible extension is associated with a single receptacle well within the receptacle holder, and wherein the movement of each cover between the first non-engagement position and second engagement position is controlled by a second controller. When at least one receptacle is present in the plurality of receptacle wells it is secured within the receptacle well by the cover when in the second position. When the cover is in the first position, a receptacle transport mechanism can access the plurality of receptacle wells to introduce or remove a receptacle. In addition, each cover can move between the first and second positions together with, or independently of, one or more other covers. The first controller and the second controller may be the same unit. In other various embodiments, the apparatus does not include a cover or a plurality of covers.

In various embodiments, the support of the apparatus is a heat sink or the support is provided in thermal communication with a heat sink. The apparatus may include a first controller electrically connected to the thermal element to cycle the temperature of the thermal element and may include one or more motors electrically connected to the first controller disposed in moveable communication with the cover, if present. In various embodiments, if present, the cover may include a rigid element and one or more flexible extensions, wherein the flexible extensions are attached to, and extend laterally away from, the rigid element to apply a force when the cover is in the closed position to at least a portion of one or more receptacles when present within the receptacle wells.

In yet another exemplary aspect, the disclosure provides an apparatus that includes one or more receptacle holders made of a heat-conducting material. Each receptacle holder includes a plurality of receptacle wells, each receptacle well being configured to receive a receptacle therein; a plurality of through-holes, each through-hole extending from an inner surface of one of the receptacle wells to an outer surface of the receptacle holder; and a plurality of optical fibers, each optical fiber having first and second ends, wherein the first end is in optical communication with one of the receptacle wells, and the second end is in optical communication with at least one of an excitation signal source and/or an emission signal detector, the first end of each optical fiber being disposed outside, within, or extending through, a corresponding through-hole in each receptacle well, one or more thermal elements positioned proximal to the receptacle holder for altering a temperature or temperatures of the receptacle holder. In various embodiments, the apparatus does not have a cover. In various embodiments, the apparatus further includes a primary cover fixedly positioned over the receptacle holder and having one or more securing arms in alignment with and disposed in a surrounding arrangement with each receptacle well of the receptacle holder, wherein one or more receptacles disposed within one or more of the receptacle wells are seated or secured into the receptacle well by the securing arms; and a secondary cover fixedly positioned over the primary cover and having one or more releasing arms in alignment with and in sliding contact with the securing arms of the primary cover. In an exemplary embodiment, application of a force onto the releasing arms urges the securing arms to flex in a radial outward direction relative to an axial center of the receptacle well, thereby releasing the receptacle disposed within the receptacle well. One, two, three, four, or more securing arms are contemplated. In other various embodiments, the apparatus does not include a primary or secondary cover. In a variety of embodiments, the one or more thermistors and/or associated wiring thereof are disposed within a channel formed in the receptacle holder. In certain embodiments, the apparatus further includes one or more closed-ended channels formed on opposing sides of a receptacle well of the receptacle holder, each having one of the thermistors disposed therein.

In yet another exemplary aspect, the disclosure provides an apparatus that includes one or more receptacle holders made of a heat-conducting material. Each receptacle holder includes a plurality of receptacle wells, each receptacle well being configured to receive a receptacle therein; a plurality of through-holes, each through-hole extending from an inner surface of one of the receptacle wells to an outer surface of the receptacle holder; a plurality of optical fibers, each optical fiber having first and second ends, wherein the first end is in optical communication with one of the receptacle wells, and the second end is in optical communication with at least one of an excitation signal source and an emission signal detector, the first end of each optical fiber being disposed outside, within, or extending through, a corresponding through-hole in each receptacle well, and wherein the first end of each optical fiber is moveable within one of the through-holes relative to the surface of the receptacle well; and one or more thermal elements positioned proximal to the receptacle holder for altering a temperature or temperatures of the receptacle holder. In various embodiments, the apparatus may further include a cover movable between an opened position and a closed position relative to the receptacle holder. When present, one or more receptacles disposed within one or more of the receptacle wells are securely seated to maximize contact with the inner surfaces of the receptacle wells without the need for contact with the cover. In certain embodiments, the apparatus may not include a cover. In a variety of embodiments, the one or more thermistors and/or associated wiring thereof are disposed within a channel formed in the receptacle holder. In certain embodiments, the apparatus further includes one or more closed-ended channels formed on opposing sides of a receptacle well of the receptacle holder, each having one of the thermistors disposed therein.

In other embodiments, the present disclosure provides methods of introducing and removing a receptacle from a receptacle holder utilizing a fluid transfer apparatus, wherein the fluid transfer apparatus is configured to fixedly introduce the receptacle to the receptacle holder and to release the receptacle from a securing mechanism disposed within the receptacle holder that fixedly holds the receptacle within the receptacle holder.

In yet another exemplary aspect, the disclosure provides a system that includes one or more apparatus of the present disclosure. In various embodiments, the system also includes a receptacle transport mechanism, which may be a modified pipettor. The receptacle transport mechanism includes a body having a plunger slidingly disposed therein, and one or more limbs hingedly attached to the body and positioned in sliding communication with a knob fixedly attached to the plunger. When the plunger is in a first position, a lower portion of the one or more limbs are proximal to the body, and when the plunger is in a second position, the lower portion of the one or more limbs are extended in a radial outward direction relative to the body.

DETAILED DESCRIPTION

Figure 1:
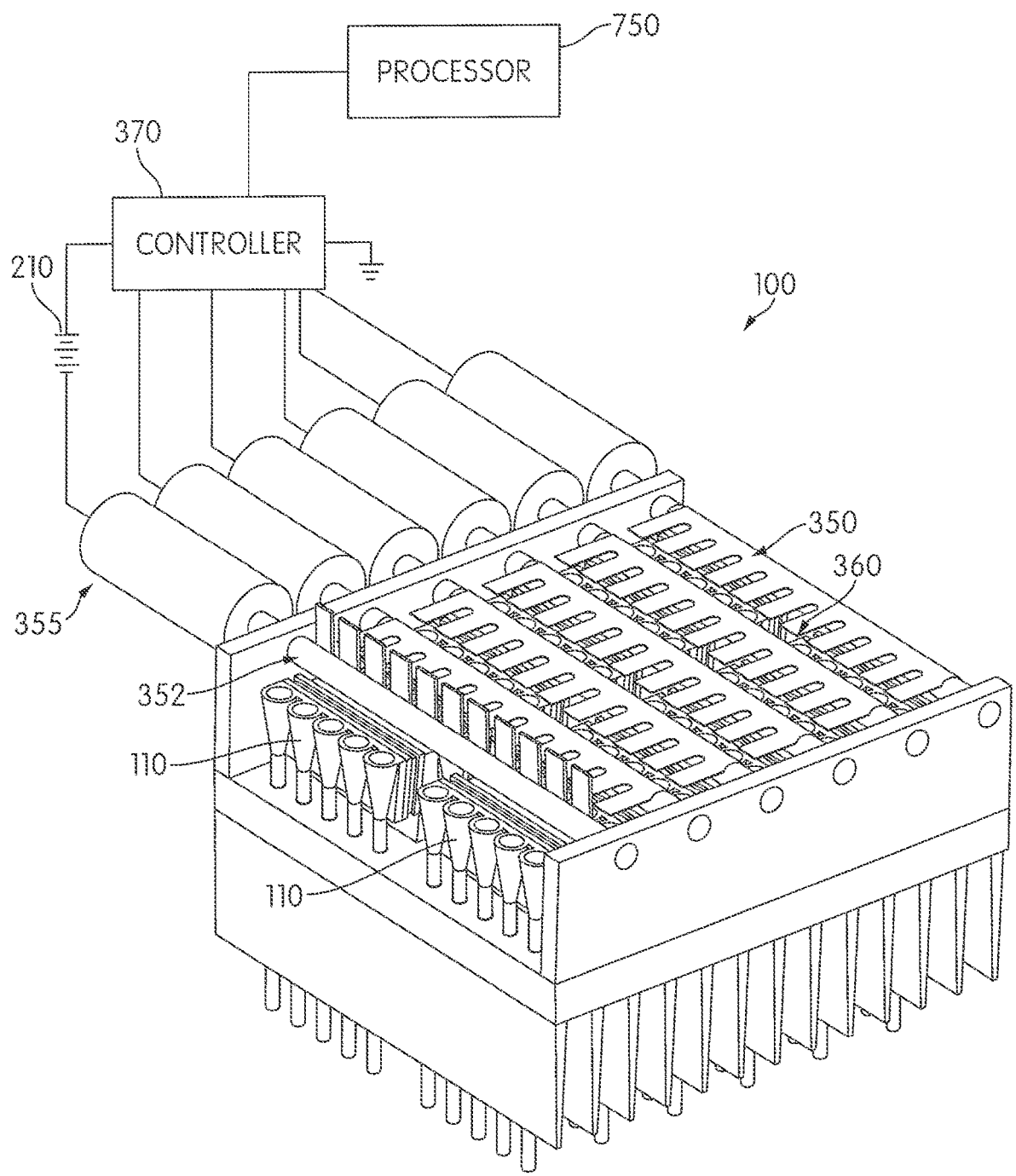
FIG. 1 is a pictorial diagram showing an apparatus of the present disclosure.

The present disclosure relates to a system, apparatus, and method for incubating at least one receptacle holder that is adapted for use in an automated instrument capable of performing nucleic acid-based amplification assays. Also provided are methods for conducting automated, random-access temperature cycling processes using the same.

Before the present systems, methods, and apparatuses are described, it is to be understood that this disclosure is not limited to particular methods and experimental conditions described, as such methods and conditions may vary. It is also to be understood that the terminology used herein is for purposes of describing particular embodiments only, and is not intended to be limiting, since the scope of the present disclosure will be limited only in the appended claims.

As used in this specification and the appended claims, the singular forms "a," "an," and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," "having," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the disclosed subject matter. The present disclosure contemplates exemplary embodiments of an apparatus and methods of use thereof corresponding to the scope of each of these phrases. Thus, an apparatus or method comprising recited elements or steps contemplates particular embodiments in which the apparatus or method consists essentially of or consists of those elements or steps.

Unless defined otherwise, all technical and scientific terms used herein have the same meaning as commonly understood by one of ordinary skill in the art to which this disclosure belongs. Although any methods and materials similar or equivalent to those described herein can be used in the practice or testing disclosed herein, the preferred methods and materials are now described.

As used herein, a "reaction mixture" refers to a volume of fluid comprising one or more of a buffer for a nucleic acid amplification reaction, one or more nucleotides, an enzyme, and a sample containing or suspected of containing a nucleic acid.

As used herein, a "sample" or a "test sample" refers to any substance suspected of containing a target organism or biological molecule, such as nucleic acid. The substance may be, for example, an unprocessed clinical specimen, a buffered medium containing the specimen, a medium containing the specimen and lytic agents for releasing nucleic acid belonging to the target organism, or a medium containing nucleic acid derived from a target organism which has been isolated and/or purified in a reaction receptacle or on a reaction material or device. In some instances, a sample or test sample may comprise a product of a biological specimen, such as an amplified nucleic acid to be detected.

As used herein, "analyte" refers to a substance, such as a nucleic acid or protein, that is detected or measured in an analytical procedure. The analyte may be contained in a sample undergoing testing.

As used herein, "polynucleotide" refers to either RNA, DNA, or a chimeric molecule containing both RNA and DNA.

As used herein, "nucleic acid" refers to a multimeric compound comprising nucleosides or nucleoside analogs which have nitrogenous heterocyclic bases, or base analogs, which are linked by phosphodiester bonds or other linkages to form a polynucleotide. Nucleic acids include RNA, DNA, or chimeric DNA-RNA polymers, and analogs thereof. A nucleic acid "backbone" may be made up of a variety of linkages, including one or more of sugar-phosphodiester linkages, peptide-nucleic acid (PNA) bonds (PCT No. WO 95/32305), phosphorothioate linkages, methylphosphonate linkages, or combinations thereof. Sugar moieties of the nucleic acid may be either ribose or deoxyribose, or similar compounds having known substitutions, such as 2' methoxy substitutions and 2' halide substitutions (e.g., 2'-F). Nitrogenous bases may be conventional bases (A, G, C, T, U), analogs thereof (e.g., inosine), derivatives of purine or pyrimidine bases, such as $N^4$-methyl deoxyguanosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo[3,4-d]pyrimidine (U.S. Pat. Nos. 5,378,825, 6,949,367 and PCT No. WO 93/13121). Nucleic acids may include "abasic" positions in which the backbone does not include a nitrogenous base for one or more residues (see U.S. Pat. No. 5,585,481). Nucleic acids also include "locked nucleic acids" (LNA), an analog containing one or more LNA nucleotide monomers with a bicyclic furanose unit locked in an RNA mimicking sugar conformation (Vester et al., 2004, *Biochemistry* 43(42): 13233-41). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Methods for synthesizing nucleic acids in vitro are well known in the art.

As used herein "oligonucleotide" or "oligomer" refers to a polymer made up of two or more nucleoside subunits or nucleobase subunits coupled together. Oligonucleotides preferably have a length in the range of from 10-100 nucleotides, more preferably 10-80 nucleotides, and still more preferably from 15-60 nucleotides. The oligonucleotide may be DNA and/or RNA and analogs thereof. The sugar groups of the nucleoside subunits may be ribose, deoxyribose and analogs thereof, including, for example, ribonucleosides having a 2'-O-methylsubstitution to the ribofuranosyl moiety. Oligonucleotides including nucleoside subunits having 2' substitutions and which are useful as detection probes, capture oligos and/or amplification oligonucleotides are disclosed in U.S. Pat. No. 6,130,038. The nucleoside subunits may be joined by linkages such as phosphodiester linkages, modified linkages, or by non-nucleotide moieties, which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo-peptide backbone, such as a 2-aminoethylglycine backbone which couples the nucleobase subunits by means of a carboxymethyl linker to the central secondary amine. (DNA analogs having a pseudo-peptide backbone are commonly referred to as "peptide nucleic acids" or "PNA," and are disclosed in U.S. Pat. No. 5,539,082). Other non-limiting examples of oligonucleotides or oligomers contemplated by the present disclosure include nucleic acid analogs containing bicyclic and tricyclic nucleoside and nucleotide analogs referred to as "Locked Nucleic Acids," "Locked Nucleoside Analogues" or "LNA." (see, e.g., U.S. Pat. Nos. 6,083,482; 6,268,490; and 6,670,461). Any nucleic acid analog is contemplated by the present disclosure, provided that the modified oligonucleotide can hybridize to a target nucleic acid under either stringent hybridization conditions or amplification reaction conditions.

As used herein, the term "biochemical assay" refers to a scientific investigative procedure for qualitatively assessing or quantitatively measuring the presence or amount or the functional activity of a target entity, such as, but not limited to, a biochemical substance, a cell, organic sample, or target nucleic acid sequence. Included in the term "biochemical assay" are nucleic acid amplification and heat denaturation (i.e., melting). Nucleic acid melting typically involves precise warming of a double stranded nucleic acid molecule to a temperature at which the two strands separate or "melt" apart. The melting process typically occurs at a temperature of about 50° C. to about 95° C.

As used herein, a "target nucleic acid sequence" or "target sequence" refers to a strand of nucleic acid molecules that is to be assayed. Thus, when used in the context of an amplification assay, a target sequence refers to a sequence of nucleotides or a portion of a nucleic acid molecule that is intended to be copied.

As used herein, "amplification" or "amplifying" refers to an in vitro procedure for obtaining multiple copies of a target nucleic acid sequence, its complement or fragments thereof. For example, an in vitro amplification reaction is an enzyme-catalyzed reaction that results in the synthesis of multiple copies of a target nucleic acid sequence, its complement or fragments thereof. Examples of amplification methods that can be used for preparing in vitro amplification reactions are given below. Preferred in vitro amplification reactions synthesize amplicons in an exponential fashion, meaning that one amplicon serves as the template for production of new amplicons. As used herein, the term "amplicon" or "amplification product" refers to a nucleic acid molecule generated in a nucleic acid amplification reaction. An amplicon or amplification product contains a target nucleic acid sequence that may be of the same or opposite sense as the target nucleic acid.

Target nucleic acid amplification involves the use of amplification oligonucleotides (e.g., primer sequences) and enzymes (e.g., polymerases) to synthesize nucleic acid amplification products (copies) containing a sequence that is either complementary or homologous to the template nucleic acid sequence being amplified. As used herein, an "amplification oligonucleotide" refers to a strand of nucleic acid that serves as a starting point for the production of amplification products. The amplification products may be either extension products or transcripts generated in a transcription-based amplification procedure. The amplification oligonucleotides may be provided to a reaction mixture free in solution or one or more of the amplification oligonucleotides may be immobilized on a solid support, including the inner surface of a chamber or chambers within a receptacle. See, e.g., U.S. Pat. Nos. 5,641,658 and 7,582,470. Examples of nucleic acid amplification procedures practiced in the art include, but are not limited to, the polymerase chain reaction (PCR), strand displacement amplification (SDA), helicase dependent amplification (HDA), loop-mediated isothermal amplification (LAMP), and a variety of transcription-based amplification procedures, including transcription-mediated amplification (TMA), nucleic acid sequence based amplification (NASBA), and self-sustained sequence replication (3SR). See, e.g., Mullis, "Process for Amplifying, Detecting, and/or Cloning Nucleic Acid Sequences," U.S. Pat. No. 4,683,195; Walker, "Strand Displacement Amplification," U.S. Pat. No. 5,455,166; Kong et al., "Helicase Dependent Amplification of Nucleic Acids," U.S. Pat. No. 7,282,328, Notomi et al., "Process for Synthesizing Nucleic Acid," U.S. Pat. No. 6,410,278; Kacian et al., "Nucleic Acid Sequence Amplification Methods," U.S. Pat. No. 5,399,491; Becker et al., "Single-Primer Nucleic Acid Amplification Methods," U.S. Pat. No. 7,374,885; Malek et al., "Enhanced Nucleic Acid Amplification Process," U.S. Pat. No. 5,130,238; and Lizardi et al. (1988) BioTechnology 6:1197. With some procedures, the formation of detectable amplification products depends on an initial antibody/antigen interaction. See, e.g., Cashman, "Blocked-Polymerase Polynucleotide Immunoassay Method and Kit," U.S. Pat. No. 5,849,478. Nucleic acid amplification is especially beneficial when the amount of analyte (e.g., targeted nucleic acid, antigen or antibody) present in a sample is very low. By amplifying a target sequence associated with the analyte and detecting the synthesized amplification product, the sensitivity of an assay can be vastly improved, since less analyte is needed at the beginning of the assay to ensure detection of the analyte.

As used herein, the term "incubate," "incubation," "incubation process" and all variants thereof, refer collectively to altering the temperature of an object in a controlled manner such that conditions are sufficient for conducting the desired biochemical assay. Thus, it is envisioned that the terms encompass heating a receptacle to a desired temperature and maintaining such temperature for a fixed time interval. Also included in the terms is the act of subjecting a receptacle to one or more heating and cooling cycles (i.e., "temperature cycling"). While temperature cycling typically occurs at relatively high rates of change in temperature, the term is not limited thereto, and may encompass any rate of change in temperature.

As used herein, a "detectable label," or simply "label," refers to a chemical moiety that can be detected or can lead to a detectable response. Detectable labels in accordance with the present disclosure can be linked to probes, such as hybridization probes, either directly or indirectly. Examples of detectable labels include, but are not limited to, radioisotopes, enzymes, haptens, chromophores such as dyes or particles that impart a detectable color (e.g., latex beads or metal particles), luminescent compounds (e.g., bioluminescent, phosphorescent or chemiluminescent moieties) and fluorescent compounds.

Receptacle Holder

Figure 2:
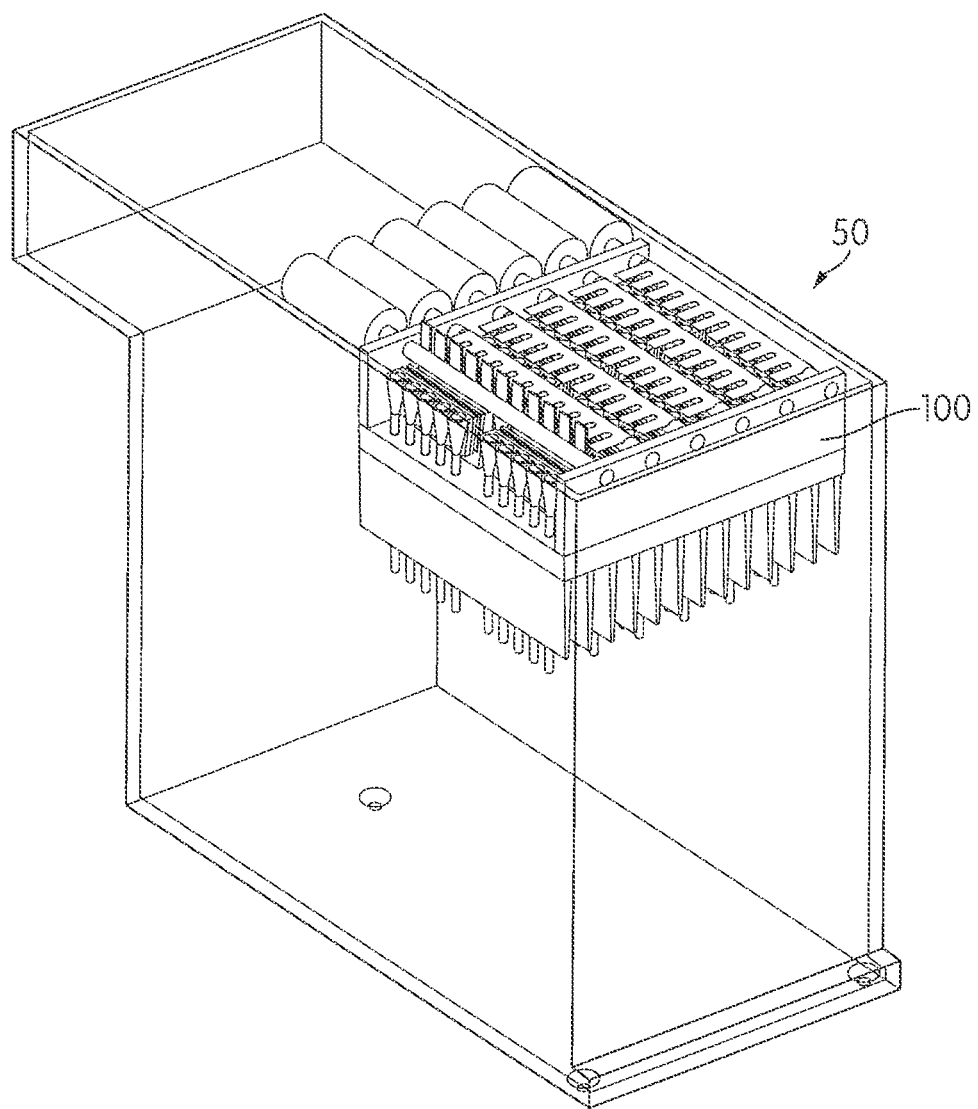
FIG. 2 is a pictorial diagram showing an apparatus of the present disclosure mounted in a housing.

The conditions of a nucleic acid amplification reaction may be substantially isothermal or they may require periodic temperature changes, as with PCR thermal cycling. The apparatus described herein may be used to heat and maintain a nucleic acid containing sample to a constant or ambient temperature or it may be used to fluctuate the temperature thereof. Target nucleic acid amplification reactions may be either "real-time" or "end-point" assays. Accordingly, in an exemplary aspect, there is provided an apparatus to perform the heating (i.e., isothermal or temperature cycling) necessary for a nucleic acid amplification assay. As shown in FIG. 1, the apparatus 100 includes one or more (i.e., 1, 2, 3, 4, 5, 6, 7, 8, 9, 10, 11, 12, or any whole number between 1 and 20, or more) receptacle holders 110 (see also FIG. 3). In an exemplary embodiment, the apparatus 100 includes two or more receptacle holders 110. Such an apparatus may include a housing 50 (see FIGS. 2 and 4) within which the one or more receptacle holders 110 are located. The housing 50 may be made from any suitable structural material such as, for example, plastic or metal.

Figure 4:
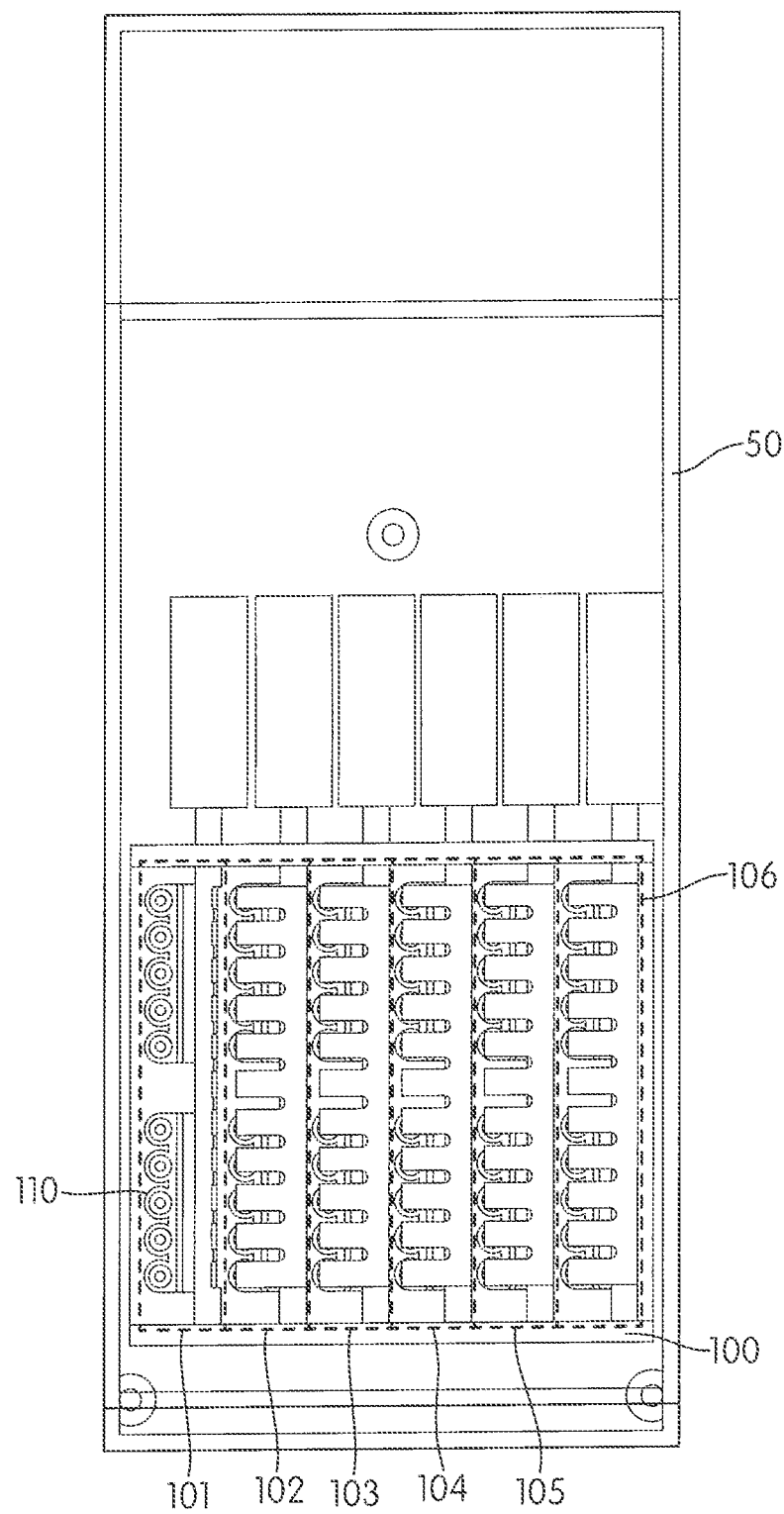
FIG. 4 is a pictorial diagram showing the top view of an apparatus of the present disclosure mounted in a housing.

When multiple receptacle holders 110 are provided in an apparatus described herein, each receptacle holder 110 disposed within the apparatus may be disposed in alignment with one another to facilitate the automated processing steps involved in nucleic acid amplification assays. It should be understood that any alignment may be used in accordance with the size and shape of the apparatus. In an exemplary embodiment, the receptacle holders are disposed within the apparatus in one or more (i.e., 1, 2, 3, 4, 5, 6, 7, 8, 9, 10, or more) rows of two receptacle holders per row, as shown in FIG. 4. Thus, two receptacle holders may be disposed in a row either in thermal connection with, or thermally separated from, one another. In an exemplary embodiment, the apparatus 100 includes six rows of two receptacle holders per row.

Figure 3A:
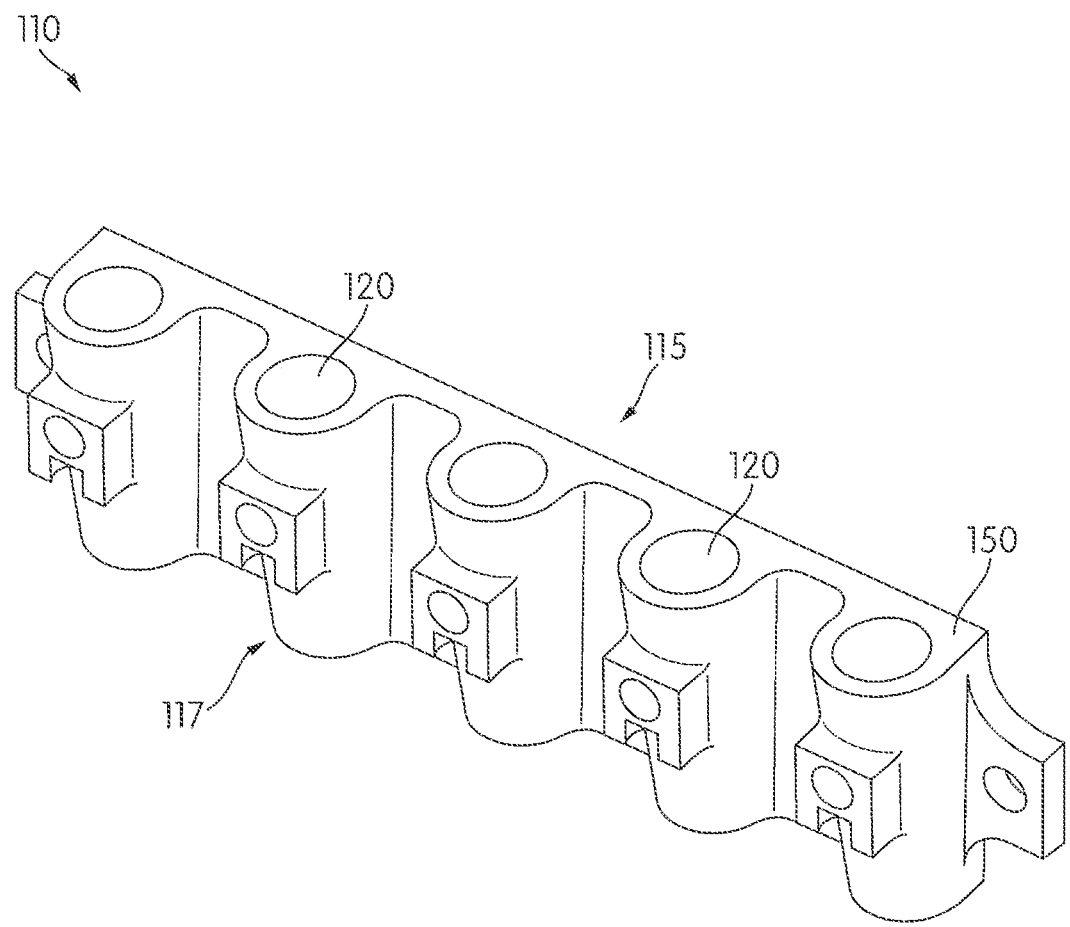
FIGS. 3A-3C are pictorial diagrams showing a receptacle holder of the present disclosure.
Figure 3B:
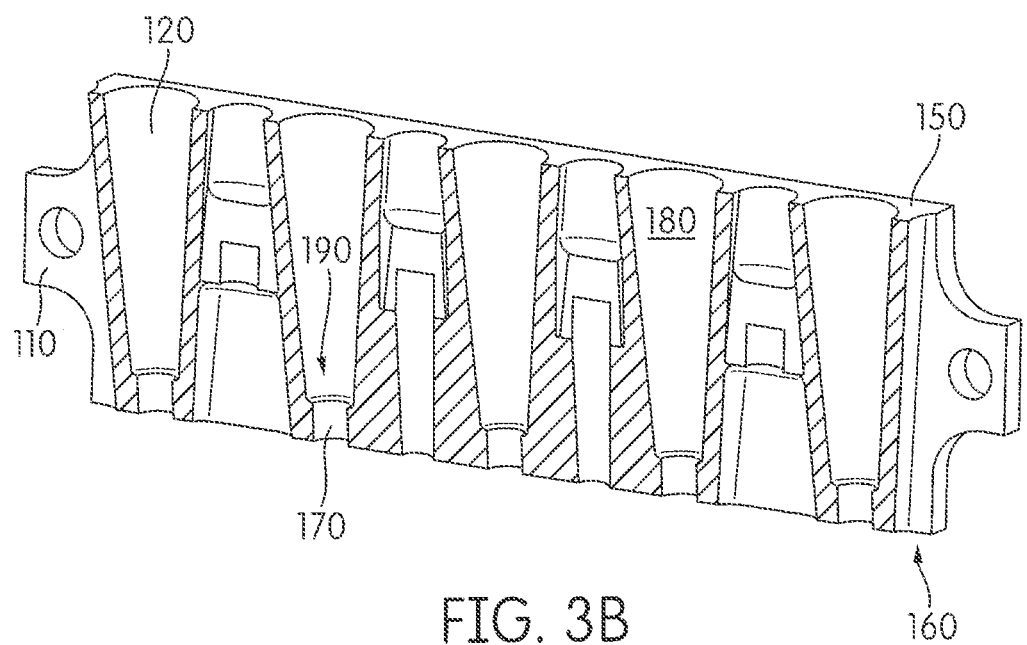
Figure 3C:
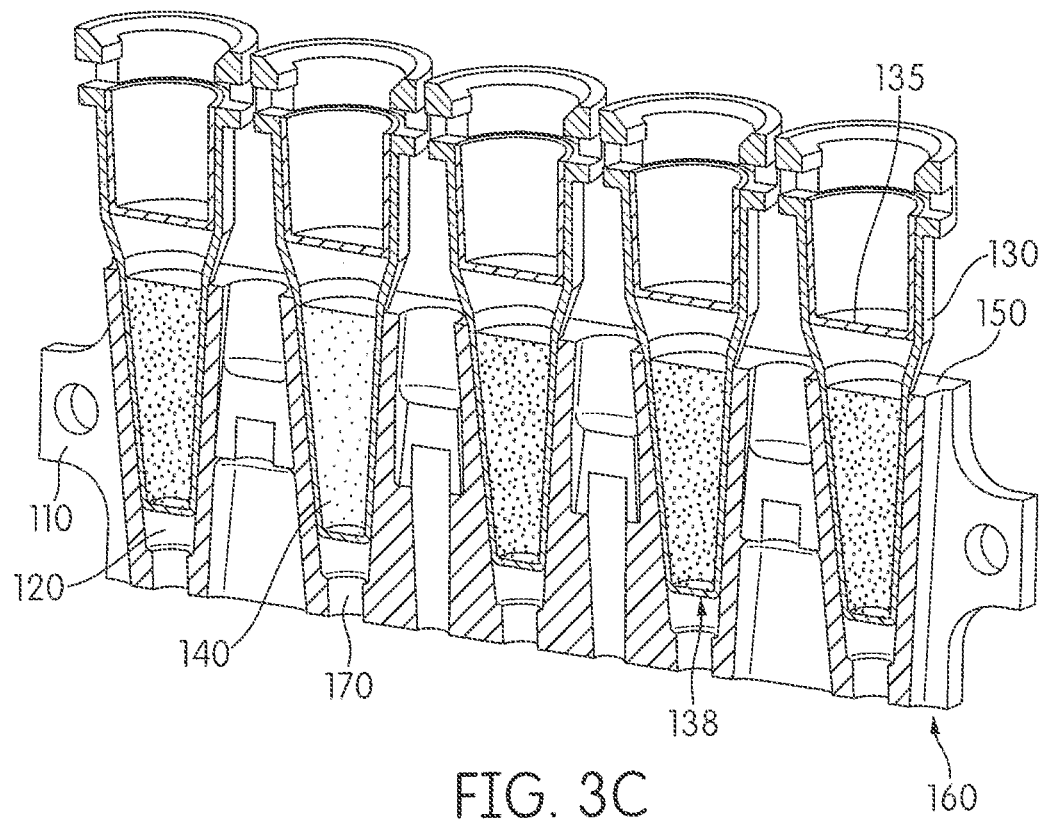

As shown in FIGS. 3A-3C, the receptacle holder 110 includes a plurality (i.e., two or more) of receptacle wells 120 that are configured to receive a receptacle 130 optionally containing a sample or reaction mixture 140. For purposes of explanation, the surface of the receptacle holder into which the receptacles 130 are inserted will be referred to as the "top surface" 150 thereof. Likewise, the surface of the receptacle holder opposite to the surface into which the receptacles 130 are inserted will be referred to as the "bottom surface" 160. In an exemplary embodiment, each receptacle holder 110 includes five or more (i.e., 5, 6, 7, 8, 9, 10, or any whole integer between 1 and 10, or more) receptacle wells 120. In another exemplary embodiment, each receptacle holder 110 includes one to ten receptacle wells. In another exemplary embodiment, each receptacle holder includes three to six receptacle wells. In yet another exemplary embodiment, each receptacle holder includes five receptacle wells. Each of the plurality of receptacle wells within a respective receptacle holder may be disposed in alignment with one another. In an exemplary embodiment, the receptacle wells 120 are disposed in a row extending along the length of the top surface 150 of the receptacle holder 110.

Exemplary materials from which a receptacle holder may be made include, but are not limited to, aluminum, titanium, copper, steel, magnesium, metal composites, metal alloys, ceramics, plastics, plastic composites, or any suitable thermally-conductive material.

As used herein, a receptacle well of the receptacle holder that is "configured to receive" a particular size or shape of receptacle refers to a receptacle well whose dimensions are substantially similar to the size and shape of a receptacle 130 (i.e., a sample tube) such that the receptacle 130 fits snugly within the receptacle well 120, thereby maximizing contact between the surface of the receptacle well 120 and the receptacle 130. In certain embodiments, this maximal contact refers to physical contact of the receptacle well 120 with at least a portion of the receptacle 130. In various embodiments, receptacles 130 in accordance with the present disclosure are individual reaction vessels made from suitable rigid or flexible materials, and shaped and dimensioned to fit within the receptacle wells of the apparatus described herein. In other embodiments, two or more (i.e., 2, 3, 4, 5, or more) receptacles may be manufactured as a single unit configured to fit within a receptacle holder. Each receptacle 130 may be closed or sealed to prevent contamination of and/or evaporation of the contents therein, and/or to facilitate handling or transport of each receptacle. Such seals may be permanent or semi-permanent and may be fluid-tight. In certain embodiments the seal comprises a cap or lid 135.

Within each receptacle well 120 is at least one through-hole 170, which extends from an inner surface 180 of the receptacle well to an outer surface of the receptacle holder. In an exemplary embodiment, the through-hole 170 of a particular receptacle well 120 extends from the bottom-center of inner surface 180 of the receptacle well 120 and extends to the surface of the receptacle holder 110 that is opposite to the surface of the receptacle holder within which the receptacles 130 are inserted (i.e., in this embodiment, the through-hole extends from the bottom of the receptacle well 120 to the bottom surface 160 of the receptacle holder 110). In certain embodiments the diameter of the through-hole 170 is the same as that of the bottom 190 of the inner surface 180 of receptacle well 120. In other embodiments, the through-hole 170 comprises a hole or opening having dimensions smaller than the bottom 190 of the inner surface 180 of receptacle well 120. In other embodiments, the through-hole 170 comprises a hole or opening having dimensions the same size as, or larger than, the bottom 190 of the inner surface 180 of receptacle well 120. The exact dimensions of the through-hole 170 may vary, provided that the presence of the through-hole 170 does not detrimentally affect the ability of the receptacle holder 110 to efficiently transfer heat to and from a receptacle 130 held within the receptacle well 120.

Thermal Element

Figure 5A:
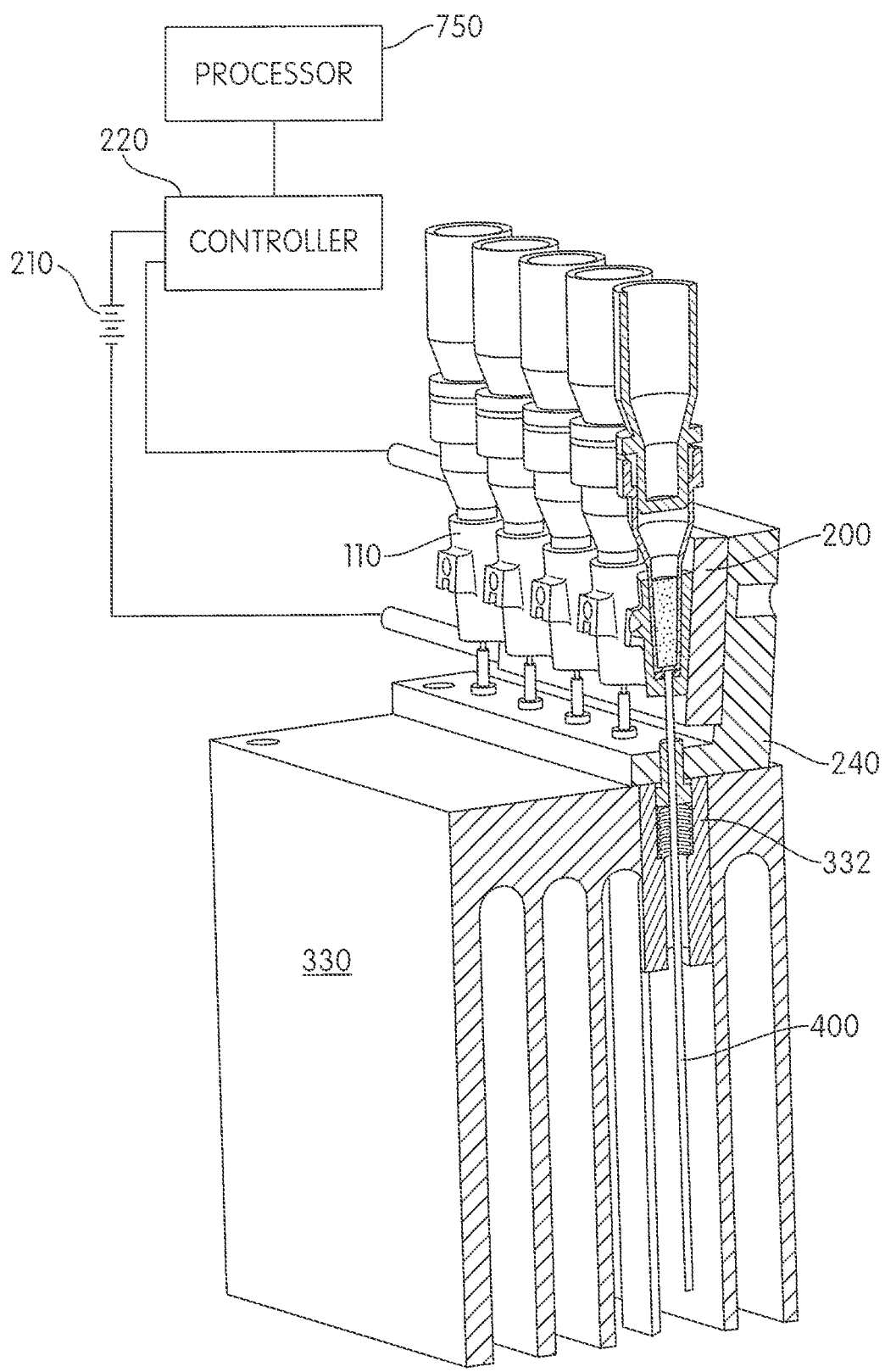
FIGS. 5A-5C are pictorial diagrams showing a receptacle holder mounted in sliding engagement with a support. The support is mounted in thermal communication with a heat sink (FIG. 5A). A cross-brace may be mounted to the support to exert a force onto a front surface of the receptacle holder (FIG. 5B). A detailed view of the support is shown in FIG. 5C.
Figure 5B:
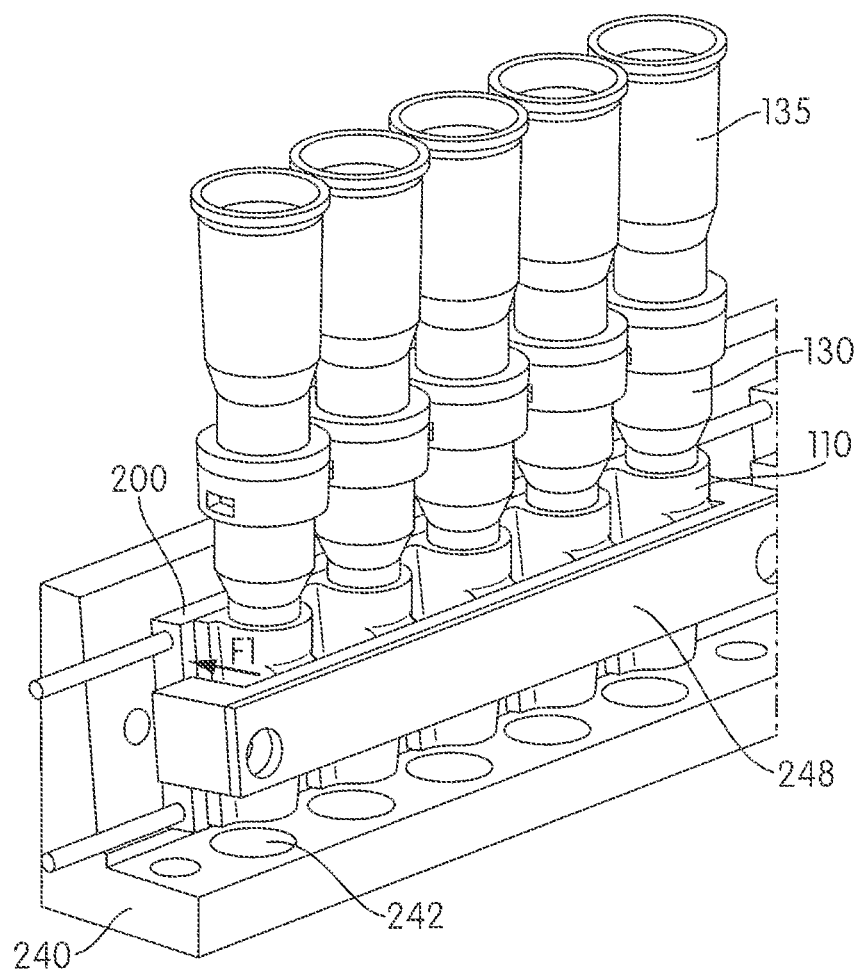

As shown in FIGS. 5A and 5B, positioned proximal to the receptacle holder is one or more thermal elements 200 for altering a temperature or temperatures of the receptacle holder 110. As used herein, the term "thermal element" may include any known heating element for heating and cooling applications. In one embodiment, the thermal element is a resistive heating element, such as a thin metal film that is applied to the receptacle holder 110 by using well-known methods such as sputtering or controlled vapor deposition. The heating element also can be provided as a molded or machined insert (e.g., such as a cartridge) for incorporation into the receptacle holder 110.

In an exemplary embodiment, the thermal element 200 is a thermoelectric device, such as a "Peltier device," which is generally constructed from electron-doped n-p semiconductor pairs that act as miniature heat pumps. When current is applied to the semiconductor pairs, a temperature difference is established whereas one side becomes hot and the other cold. If the current direction is reversed, the hot and cold faces will be reversed. Usually an electrically nonconductive material layer, such as aluminum nitride or polyimide, is disposed over the substrate faces of the thermoelectric modules so as to allow for proper isolation of the semiconductor element arrays.

As used herein, "altered temperature or temperatures" of the receptacle holder refers to the increase or decrease of the temperature of the receptacle holder 110. Often, the increase or decrease of the temperature is determined relative to the ambient temperature. Included in the term is the ability to individually adjust the temperature of one or more receptacle wells 120, while separately adjusting the temperature of other receptacle wells within the same receptacle holder. Thus, the term may refer to uniformly raising/lowering the temperature of all receptacle wells 120 within a receptacle holder 110 or may refer to altering a subset of the receptacle wells 120 within a single receptacle holder 110. As used herein, "ambient temperature" refers to the temperature of a surrounding environment, which may include a fluid (e.g., air or liquid) or solid structure.

The thermal element 200 may be electrically connected to a controllable power source 210 for applying a current across the element to alter the temperature thereof. Control of the power source 210 can be carried out by an appropriately programmed controller 220 (such as a computer) which receives signals from one or more thermal sensors 610 (see FIG. 6A) in thermal communication with the receptacle holder 110, as discussed below, and/or signals from another processor 750 that controls the automated process steps involved with temperature cycling processes.

The thermal element 200 may be held in contact with a side surface 115 (see FIG. 3A) of the receptacle holder 110 by one or more supports 240 (see FIG. 5C), which may be positioned in sliding engagement with the receptacle holder 110. As used herein, being positioned "in sliding engagement" refers to a non-fixed contact between adjacent surfaces of different parts of the apparatus described herein. Thus, when the apparatus 100 includes two or more receptacle holders 110, each of the two or more receptacle holders are configured in sliding engagement with a support 240. As used herein, the term "support" refers to a rigid structure, which can be thermally-conductive. Exemplary materials from which a support may be made include, but are not limited to, aluminum, titanium, copper, steel, magnesium, metal composites, metal alloys, ceramics, plastics, plastic composites, or any suitable rigid thermally-conductive material. Supports may also comprise a structure formed of, or from, a combination of materials, for example, plastic, metal (including alloys and composites), ceramic, or a combination of different types of one or more of these materials.

As is known in the art, thermal elements may require a specific force to achieve adequate thermal contact with a component that is to be heated. For example, certain Peltier devices require a mounting force of approximately 150-300 psi to effectively transfer thermal energy to a device. With reference to FIG. 5B, the apparatus may include one or more cross-braces 248 mounted to a support 240, and which exert a force F1 onto a front surface 117 (see FIG. 3A) of a receptacle holder 110. Force F1 is sufficient to effect thermal transfer of energy from thermal element 200 to receptacle holder 200. In certain embodiments, the apparatus includes one cross-brace 248 for each receptacle holder 110. In other embodiments, the apparatus includes one cross-brace 248 per row of receptacle holders 110. In such embodiments, the cross-brace generally incorporates a portion or layer having low thermal conductivity as the portion that directly contacts the receptacle holder 110. As discussed below, in other embodiments, a body 300 (see FIGS. 6A, 6B, 7A) having low thermal conductivity is used to exert the force required for thermal transfer of energy to the receptacle holder 110.

Support

Figure 5C:
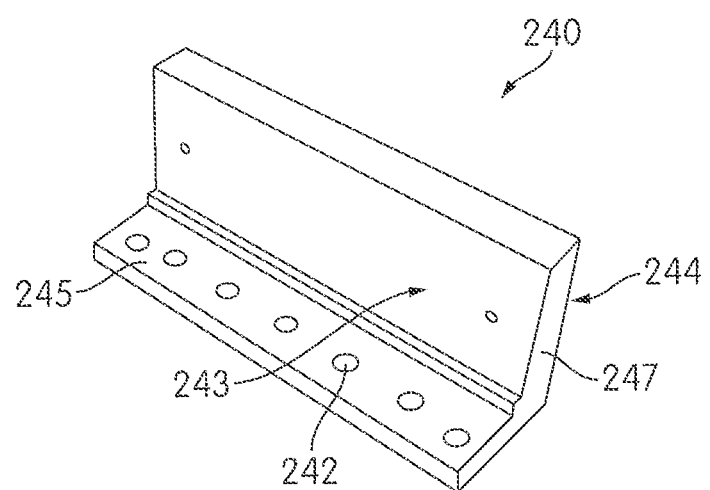

As shown in FIG. 5C, the support 240 may be formed in a shape suitable for use in the apparatus described herein. In an exemplary embodiment, the support is a solid member having a base portion 245 and an upright portion 247. In certain embodiments, the base portion 245 and upright portion 247 comprise a single contiguous material. The upright portion 247 may intersect the base portion at a right angle or may intersect the base portion 245 at an angle greater or less than 90°. Disposed within the base portion is a plurality of through-holes 242, which are preferably in alignment with the through-holes 170 of the bottom surface 160 of the receptacle holder 110 that will be positioned in sliding engagement therewith. Each of the through-holes 242 of the base portion 245 of the support 240 form a channel through which optical fibers 400 (see FIGS. 5A, 7A) and/or associated components such as a fixed or moveable ferrule 450, for example, may pass, thereby providing optical communication between each receptacle well 120 and an excitation signal source and/or an emission signal detector, as discussed below.

The upright portion 247 of the support 240 includes a first side 243 and second side 244. The first side 243 is configured to be positioned proximal to a side surface 115 of the receptacle holder 110, with the thermal element 200 being positioned between the first side 243 of the support 240 and the receptacle holder 110. The second side 244 of the upright portion 247 of the support 240 provides a solid surface to which at least one body 300 having low thermal conductivity may be disposed (see FIGS. 6A, 6B, and 7A).

Body & Linker

Figure 6A:
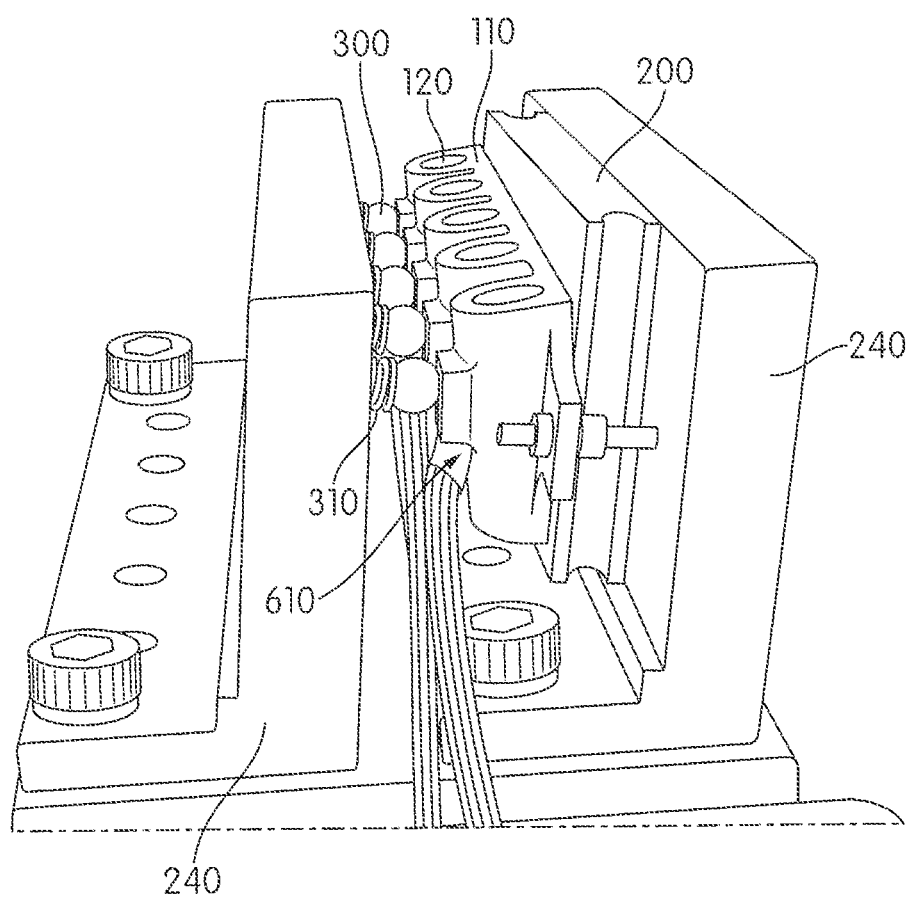
FIGS. 6A and 6B are pictorial diagrams showing a receptacle holder mounted in sliding engagement with a support.
Figure 6B:
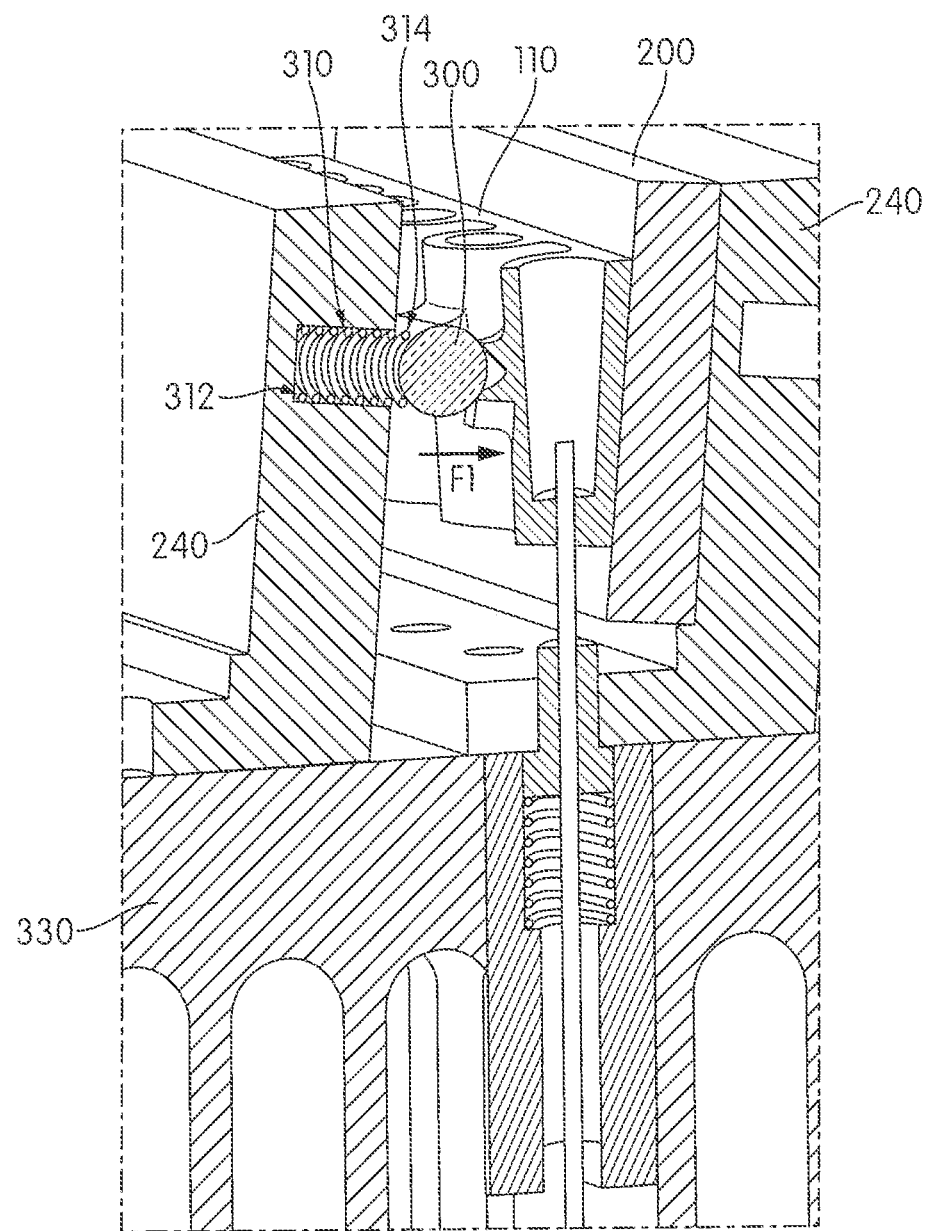
Figure 7A:
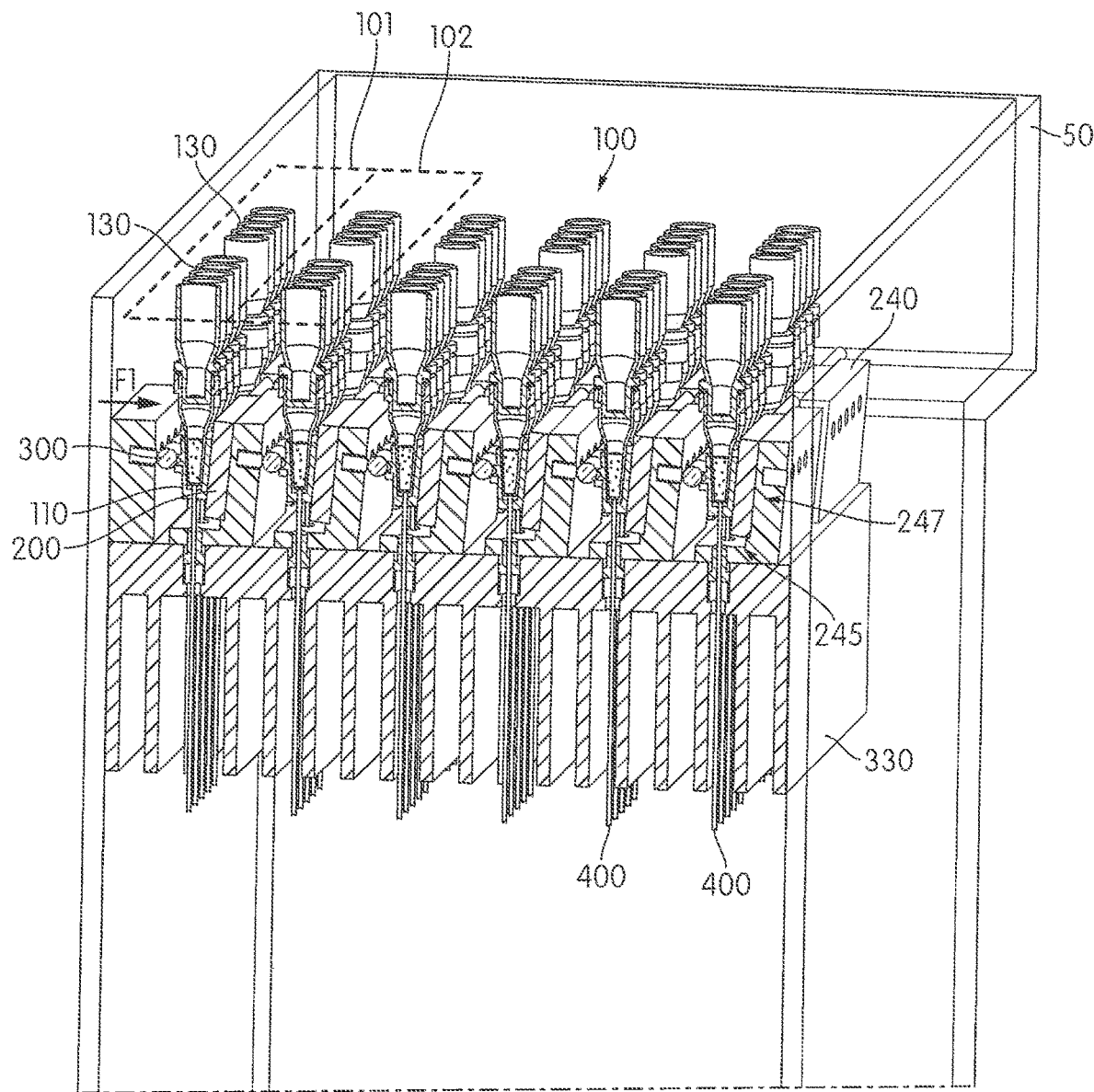
FIGS. 7A and 7B are pictorial diagrams showing multiple rows of receptacle holders disposed in an apparatus of the present disclosure (FIG. 7A), and that cartridge heaters may be disposed within the heat sink of the apparatus (FIG. 7B).

As shown in FIGS. 6A, 6B, and 7A, when the apparatus 100 includes multiple supports 240 that are oriented in rows, as discussed above, the apparatus may include one or more bodies 300 having low thermal conductivity, each associated with a respective receptacle well 120 of a receptacle holder 110. In certain embodiments, the apparatus will include a linker for exerting force F1 through the body 300 onto the receptacle holder 110.

As used herein, the term "linker" refers to any device that can exert a force in the direction that extends away from the surface upon which it is mounted. Exemplary linkers useful in the apparatus include, but are not limited to, springs, spacers, linear expanders, materials formed of elastic or rubbery material, piezoelectric devices, levers, screws, etc. As such, in an exemplary embodiment, a first end 312 of a linker 310 (e.g., spring) is mounted to the second side 243 of the upright portion 247 of a support 240, while a second end 314 contacts and exerts a force F1 onto a body 300 having lower thermal conductivity (e.g., a glass or plastic bead, cap, or insert). Each body 300 then transfers the force F1 exerted upon it by the linker 310 onto the front surface 117 of the receptacle holder 110 opposite to the side surface 115 of the receptacle holder 110 that is in contact with the thermal element 200, thereby ensuring maximal contact between the thermal element 200 and the receptacle holder 110. In one embodiment, the apparatus 100 includes one to ten linkers 310 per support 240, depending on the number of receptacle holders 110 positioned in sliding engagement therewith. In another embodiment, the apparatus 100 includes one linker 310 per receptacle well 120. In yet another embodiment, the apparatus 100 includes two linkers 310 per support 240. In yet another embodiment, the apparatus 100 includes five linkers 310 per support 240.

It is noted that the body 300 should have a lower thermal conductivity than the receptacle holder 110 in order to prevent thermal energy from transferring from the receptacle holder 110 to the body 300 and/or support 240. Exemplary bodies for use in the apparatus include, but are not limited to, glass or plastic beads that are connected, either directly or indirectly, to the receptacle holder by a linker 310 located between the support 240 and the body 300.

Thus, as shown in FIG. 7A, a support 240 of a row of receptacle holders 110 may be provided as a solid surface by which body 300 and linker 310 exert a force F1 to the receptacle holder 110 positioned in sliding engagement with the support 240 located in the row immediately subsequent thereto. For example, the body 300 of a first support 240 positioned in a first row 101 of receptacle holders 110 exerts a force F1 onto the front surface 117 of a receptacle holder 110 positioned in sliding engagement with a second row 102, wherein the first 101 and second 102 rows are adjacent to one another within the apparatus 100, as described herein.

In certain embodiments, the apparatus may include a single support 240 in sliding engagement with all receptacle holders 110, or may include a single support 240 in sliding engagement with each row (e.g., 101-106 in FIGS. 4 and 7A) of receptacle holders 110, or may include a single support 240 in sliding engagement each individual receptacle holder 110.

Thermistors

In various embodiments, the apparatus may further include one or more (i.e., 1, 2, 3, 4, 5, 6, 7, 8, 9, 10, or more) thermal sensors 610 to monitor the temperature of the receptacle holder 110. A wide variety of microsensors are available for determining temperatures, including, e.g., thermocouples having a bimetallic junction which produces a temperature dependent electromotive force (EMF), resistance thermometers which include material having an electrical resistance proportional to the temperature of the material, thermistors, IC temperature sensors, quartz thermometers and the like. See, e.g., Horowitz and Hill, The Art of Electronics, Cambridge University Press 1994 (2nd Ed. 1994). As used herein, the term "thermistor" refers to a type of resistor whose resistance varies significantly with temperature. Such thermistors 610 may be disposed in direct or indirect contact with the receptacle holder 110. In one embodiment, two or more thermistors 610 are disposed in contact with a receptacle holder 110. In another embodiment, one or more thermistors 610 are disposed in contact with each of the receptacle wells 120 of a single receptacle holder 110 to enable monitoring of the temperatures of each of the individual receptacle wells 120.

Figure 5D:
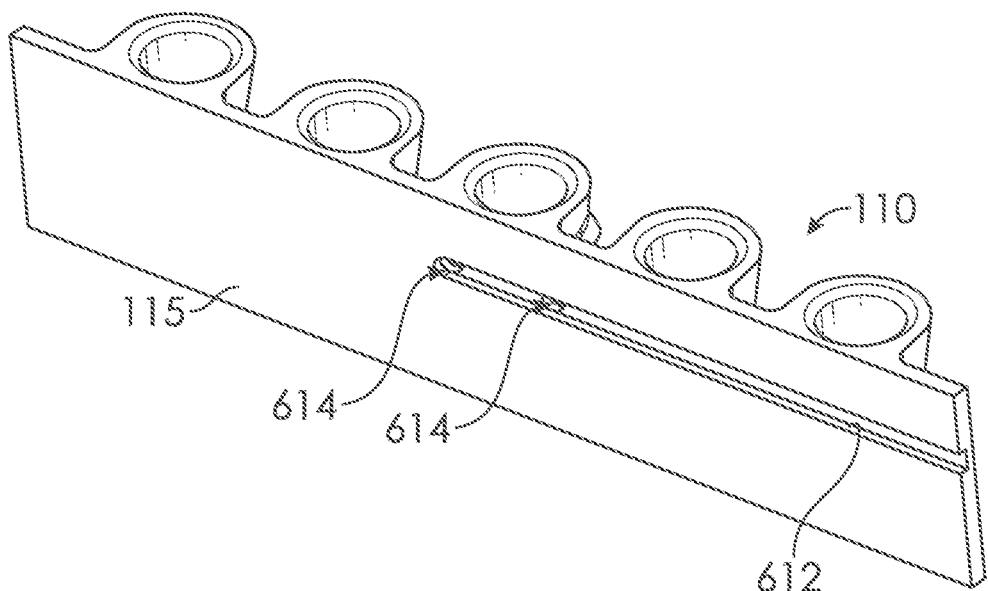
FIGS. 5D and 5E are pictorial diagrams showing an exemplary receptacle holder. The receptacle holder may include a channel through which the wiring and/or electrical connections for one or more thermistors may be disposed (FIG. 5D). The receptacle holder may also include one or more bulges formed corresponding to closed through-holes disposed within the channel for containing the one or more thermistors (FIG. 5E).

As shown in FIG. 5D, in an exemplary embodiment, receptacle holder 110 may include a channel 612 disposed within the side surface 115. In various embodiments, the channel extends from an edge of the side surface 115 to a location corresponding to a center-most receptacle well 120 of the receptacle holder 110. For example, in embodiments wherein the receptacle holder 110 includes five receptacle wells 120, the channel 612 frequently extends to a location that corresponds with the third/central receptacle well 120. The channel 612 is configured to accept therein wires and/or electrical connections for the thermistors 610 of the receptacle block. Disposing the wires and/or electrical connections of the thermistors 610 within the channel 612 shields the thermistors and associated wiring thereof from the heat-depleting effects of ambient temperatures, thereby ensuring accurate monitoring of the temperature of the receptacle holder 110. Provided at the end of the channel 612 corresponding with the center-most receptacle well 120 may be one or more closed through-holes 614 through which the thermistors may be provided such that the thermistors are in contact with the center-most receptacle well 120. In certain embodiments, two through-holes 614 are provided within the channel 612 such that two thermistors may be disposed therein to monitor the temperature of the receptacle holder 110 on opposing sides of the center-most receptacle wells 120. Although not shown, channel 612 may extend the length of the receptacle holder 110, and two closed through-holes 614 corresponding to each of the receptacle wells 120 may be provided therein.

Figure 5E:
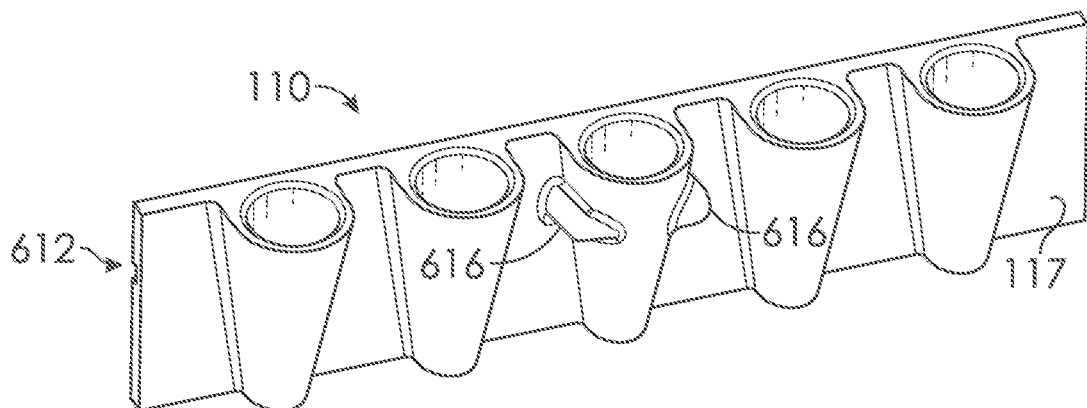

As shown in FIG. 5E, to accommodate the thermistors inserted through through-holes 614, the receptacle holder 110 may be formed to include one or more bulges 616 disposed on opposing sides of the center-most receptacle holder 120. The bulges 616 provide a closed-ended channel surrounding a portion of the receptacle well 120 that extend from the side surface 115 of the receptacle holder 110 and terminating at the front surface 117 opposite to the side surface 115 of the receptacle holder 110. Thus, when two thermistors 610 are provided to monitor the temperature of the receptacle holder 110, one thermistor 610 is provided in each bulge 616 thereof. Although not shown, when channel 612 extends the length of the receptacle holder 110, and two through-holes 614 are provided corresponding to each of the receptacle wells 120, receptacle holder 110 may include one bulge 616 per through-hole 614 to accommodate individual thermistors therein. It is contemplated that additional through-holes 614 may be provided, corresponding to two or more of the receptacle wells, including one or more through-holes 614 for each receptacle well.

Heat Sink

In an exemplary embodiment, each support 240 is a heat sink or is in thermal communication with an individual heat sink 330. As used herein, the term "heat sink" refers to a component that transfers thermal energy from a higher temperature to a lower temperature fluid medium. The fluid medium is frequently air but can also be water or in the case of heat exchangers, refrigerants and oil. A variety of suitable heat sink configurations and related materials are well known in the art. As used herein, the term "thermal communication" refers to the ability to transfer thermal energy from one body to another or from one body to a fluid medium.

Figure 7B:
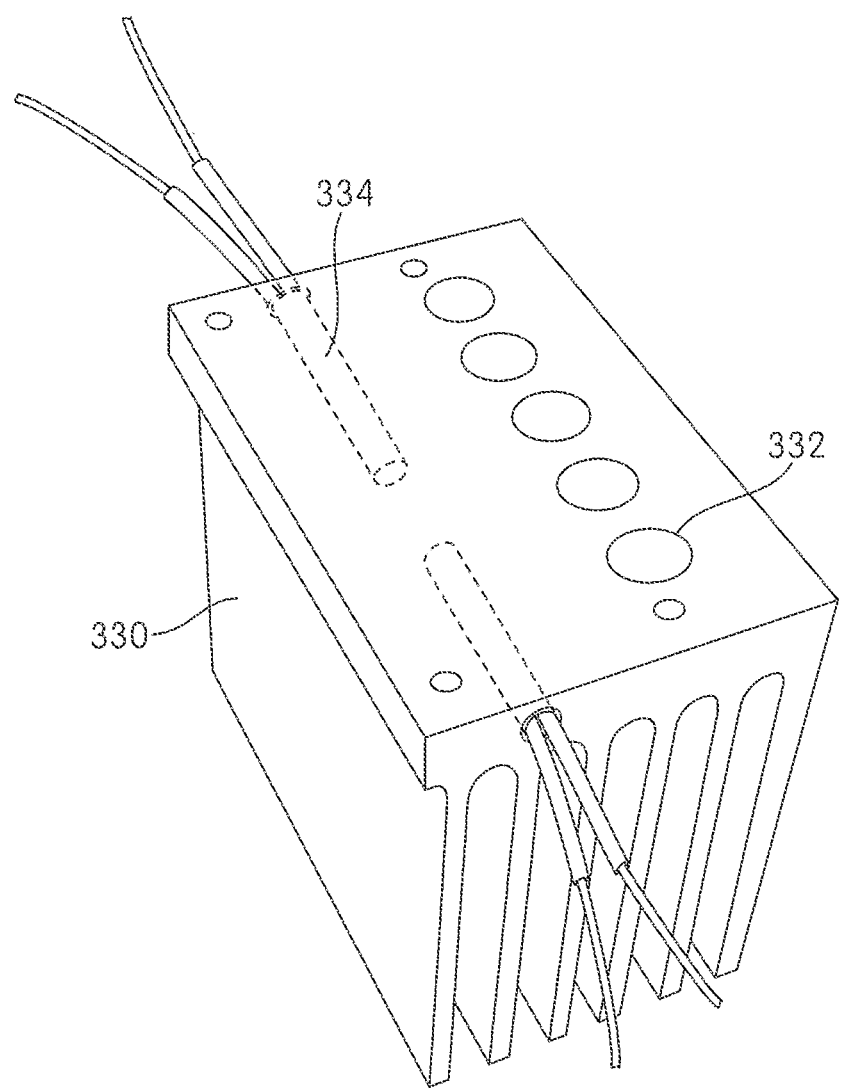

As shown in FIG. 7A, in certain embodiments, each support 240 is provided in thermal communication with a single heat sink 330. Each heat sink 330 positioned in thermal communication with one or more supports 240 of the apparatus 100, may further include a plurality of through-holes 332 (see FIG. 7B) disposed in a surface thereof. Each through-hole 332 may be in direct alignment with the through-holes 242 of the support and/or the through-holes 170 at the bottom surface 160 of the receptacle holders 110 that are positioned in sliding engagement therewith. Such through-holes 332 form a channel through which optical fibers and/or associated components, for example, may pass thereby providing optical communication between each receptacle well 120 and an excitation signal source and/or an emission signal detector, as discussed below.

In certain embodiments, disposed within heat sink 330 may be one or more thermal devices separate from those used to heat the receptacle holders to pre-heat the heat sink prior to the amplification assay. Pre-heating of the heat sink may be desirable to reduce the temperature difference between the receptacle holder 110 undergoing heating and the heat sink, thereby avoiding sapping of the thermal energy being transferred to the receptacle holder 110 by the thermal element 200. It has been found that pre-heating the heat sink, among other things, improves temperature cycling rates and reduces the electric and thermal strain on the thermal element, thus reducing power consumption and increasing the lifespan of the thermal element. The heat sink may be pre-heated to a temperature above ambient temperature, but at or below a nucleic acid annealing temperature, e.g., at or below about 50° C.-64° C., but above about 20° C.-22° C. In another embodiment, the heat sink may be pre-heated to a temperature between an annealing temperature and an elongation/extension temperature, e.g., between about 50° C.-64° C. and about 72° C.-80° C. In another embodiment, the heat sink may be pre-heated to a temperature between an elongation/extension temperature and a melting/denaturation temperature, e.g., between about 72° C.-80° C. to about 94° C.-98° C. In another embodiment, the heat sink may be pre-heated to a temperature between an annealing temperature and a melting/denaturation temperature, e.g., between about 50° C.-64° C. and about 94° C.-98° C. Exemplary thermal devices used for pre-heating the heat sink 330 include, but are not limited to, cartridge heaters 334. In various embodiments, the one or more cartridge heaters 334 pre-heat the heat sink 330 to about 45° C.-50° C., for example, prior to the amplification assay. As should be understood, additional thermistors may be provided in thermal contact with one or more portions of the heat sink to monitor the temperature thereof to avoid sapping of the thermal energy being transferred to the receptacle holder 110 by the thermal element 200.

Cover

As shown in FIGS. 1, 2, 8, and 12, the apparatus 100 may also include a cover 350 that is positioned in movable association with the receptacle holder 110. As can be expected, the cover 350 is movable between an opened position (FIG. 8B) and a closed position (FIG. 8C) relative to the receptacle holder 110 and may be moved to any position between opened and closed, as necessary. In the opened position, the cover 350 does not obstruct access to the receptacle wells 120 within the receptacle holder 110 (see FIG. 8A). When in the closed position, the cover 350 will block and/or obstruct access to the receptacle wells 120. In addition, when closed, the cover 350 may exert a force F2 onto any receptacle within a receptacle well 120 to seat or secure the receptacle 130 into the receptacle well 120 (see FIG. 8C). As discussed above, because the receptacle well 120 is configured to receive a receptacle 130, the force F2 exerted by the cover 350 serves to ensure that the receptacle 130 fits snugly within the receptacle well 120, thereby allowing maximal contact between the inner surface 180 of the receptacle well 120 and the receptacle 130.

The cover 350 may be made from any rigid or semi-rigid material suitable for exerting downward pressure onto a receptacle disposed within a receptacle well. Exemplary materials from which the cover may be made include, but are not limited to, beryllium copper, spring steel, chrome vanadium, chrome silicon, phosphor bronze, stainless steel, aluminum, titanium, tungsten, metal alloys, metal composites, plastic, or any suitable rigid or semi-rigid material.

Figure 8A:
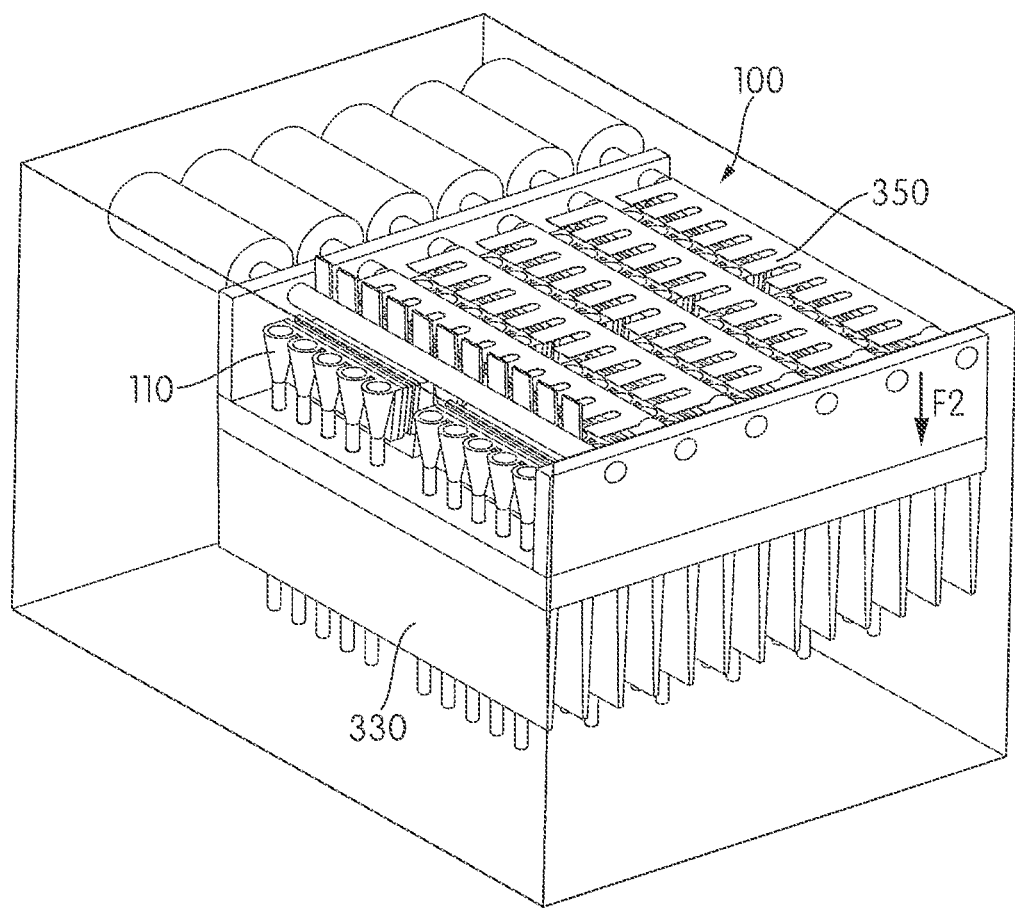
FIGS. 8A-8E are pictorial diagrams showing exemplary covers and stripper plates disposed within the apparatus of the present disclosure.
Figure 8B:
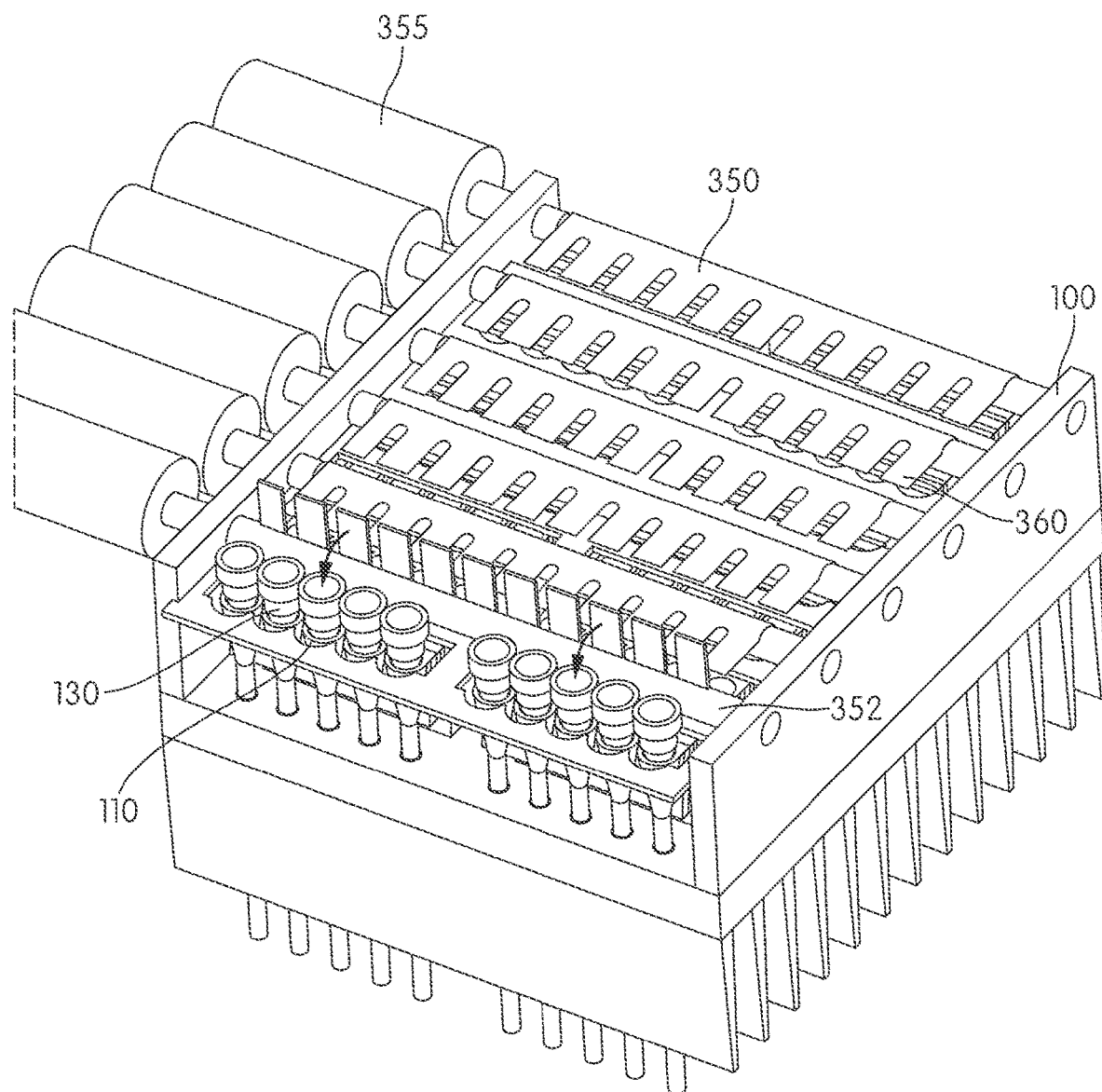
Figure 8C:
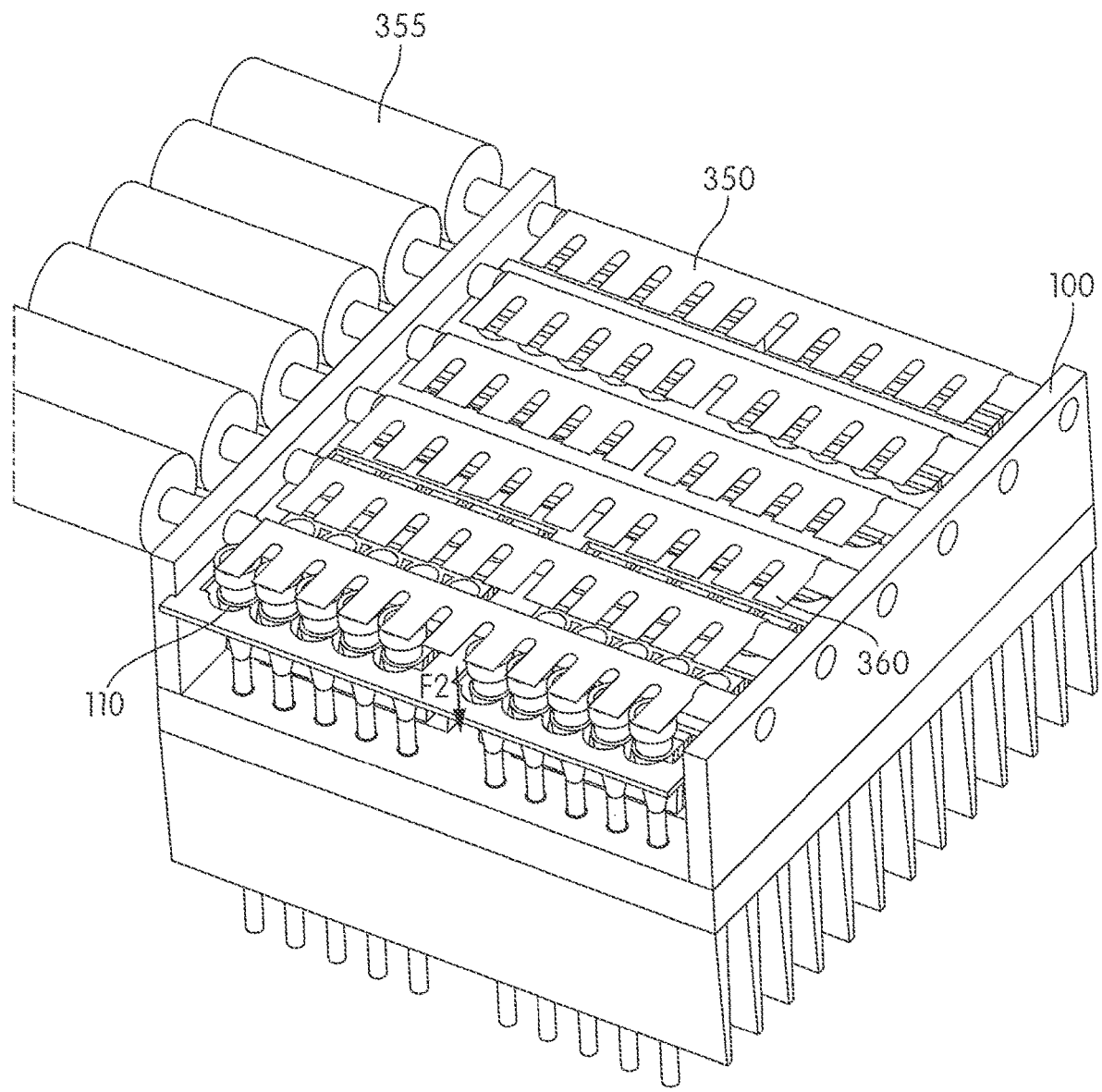
Figure 8D:
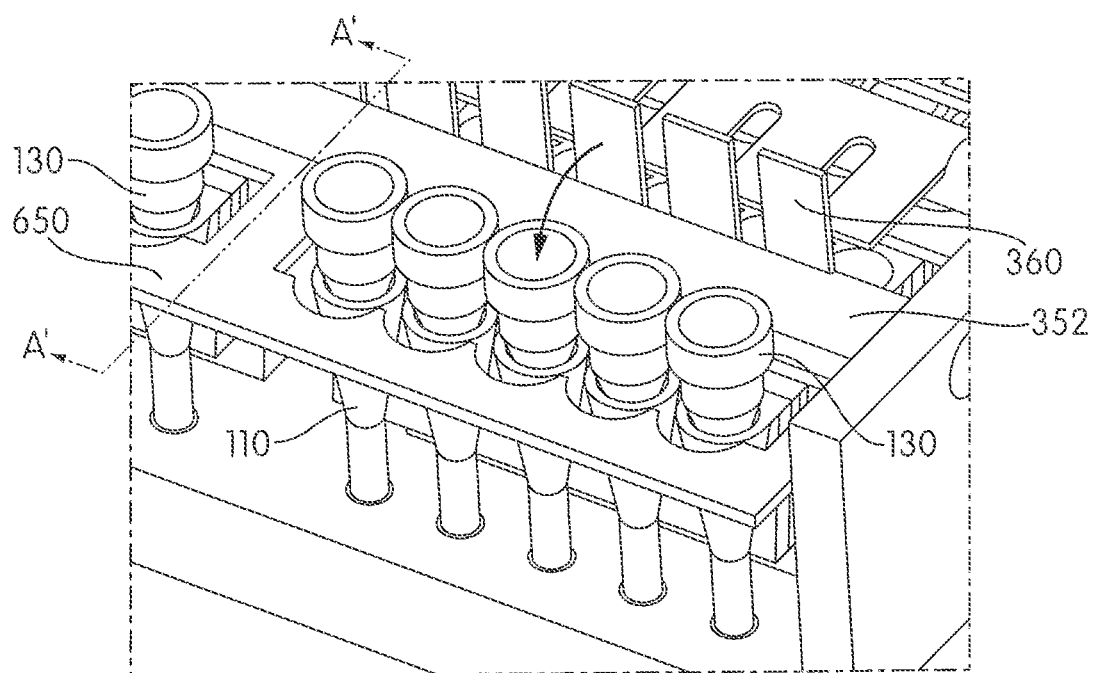
Figure 8E:
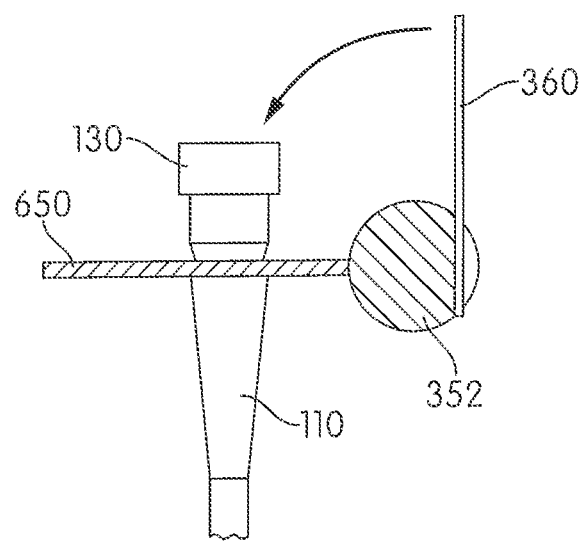

The cover 350 may be movable by any suitable mechanical element included in the apparatus. In one embodiment, the cover 350 is hingedly attached to the apparatus 100 so as to enable movement between the open and closed positions. Attachment points include but are not limited to any of the one or more supports of the apparatus or any suitable location within a housing containing the apparatus. As shown in FIG. 1, the cover 350 may be fixedly attached to a rigid rotatable member 352, which is in movable communication with one or more electric motors 355. The rotatable member may be rotatably mounted to opposing sides of the housing 50 of the apparatus or opposing sides of additional support members thereof, and span a length of the apparatus parallel to the orientation of one or more receptacle holders such that actuation of the rotatable member 352 results in the cover 350 being moved into the opened or closed position relative to the one or more receptacle holders 110. In an exemplary embodiment, the rotatable member 352 is a cylindrical rod having a circular cross-section and an axis of rotation at the center thereof, as shown in FIG. 8E, which is a sectional view taken along A'-A' in FIG. 8D. Exemplary materials from which the rigid rotatable member may be made include, but are not limited to, steel, titanium, aluminum, or any suitable rigid material. As used herein, the term "rotatably mounted" refers to any mounting orientation that allows the rotatable member to rotate about its center axis.

The cover 350 may comprise one or more (i.e., 1, 2, 3, 4, 5, 6, 7, 8, 9, 10, or more) flexible extensions 360 attached to and extending laterally away from, the rigid rotatable member 352. Such flexible extensions 360 are configured to make contact with at least a portion of a receptacle 130 disposed within the receptacle holder 110 when the cover is in, approaching, or for a short distance after leaving, the closed position. As contact is made between the flexible extensions 360 and at least a portion of the receptacle 130, the flexible extensions 360 flex while applying force F2 directly to at least a portion of the receptacle 130. In an exemplary embodiment, the cover 350 includes two or more (i.e., 2, 3, 4, 5, 6, 7, 8, 9, 10, or more) flexible extensions 360 extending in the same direction away from the rigid rotatable member 352. In certain embodiments, the flexible extensions 360 extend laterally away from the hinged attachment of the cover 350 to the apparatus 100. In frequent embodiments, the cover 350 includes one flexible extension 360 per receptacle well 120 of a receptacle holder 110. Also, in frequent embodiments, one flexible extension 360 of the cover 350 may contact at least a portion of more than one receptacle 130 disposed within the receptacle holder 110. Likewise, more than one flexible extension 360 may contact at least a portion of more than one receptacle 130 disposed within the receptacle holder 110.

The cover 350 of the present disclosure often comprises multiple components, such as flexible extensions 360, a rotatable member 352, or other elements, as a single molded cover unit, or in multiple elements comprising the entire cover unit. For example, the flexible extensions 360 may be attached to the rotatable member 352, or a single material may comprise the rotatable member 352 and the flexible extensions 360.

The apparatus 100 may include a single cover 350 in moveable association with all receptacle holders 110 (not shown), or it may include a single cover 350 for each row of receptacle holders 110, or it may include a single cover 350 for each individual respective receptacle holder 110. Movement of each cover 350 may be actuated by an electric motor 355 disposed either within the apparatus 100 or within the housing 50 in which the apparatus is located. When the apparatus 100 includes more than one cover 350, each cover 350 may be actuated by its own motor 355, or more than one cover 350 may be actuated by the same motor 355. As such, when the apparatus 100 includes more than one cover 350, each cover 350 may move independently of the next and/or more than one cover 350 may be moved simultaneously. One of skill in the art would appreciate that independent movement of multiple covers utilizing a single motor may be provided through, for example, appropriate camming of its connection to each cover. The electric motor 355 is electrically connected to a controllable power source 210 for applying a current thereto. Control of the power source 210 can be carried out by an appropriately programmed controller 370 (such as a computer) which may receive signals from another processor 750 that controls the automated process steps involved with temperature cycling processes.

Though several embodiments of the apparatuses and methods of the present disclosure include a cover, a cover is not required, and often not included or desired. For example, in particularly frequent embodiments, the receptacle holder does not have a cover in operable orientation therewith. In such embodiments, receptacles are often held in place in the receptacle holder, for example, by gravity, friction, and/or another mode. When the apparatus is provided without a cover for the receptacles, it will frequently comprise any of the configurations of the apparatus described herein, but lacking the cover, including all associated instrumentation and mechanical and/or electrical elements associated therewith. Frequently, in such embodiments, a pipettor or receptacle transport mechanism will have uninhibited access to the receptacle holder to introduce or remove receptacles at will. An example of an apparatus without a cover is depicted in FIG. 14B. Such an apparatus could be readily attached to a heat sink, in communication with a detection system, and a power source and be fully operational. In frequent embodiments multiple of these apparatuses are incorporated on a single heat sink.

Optical Fibers

Figure 9A:
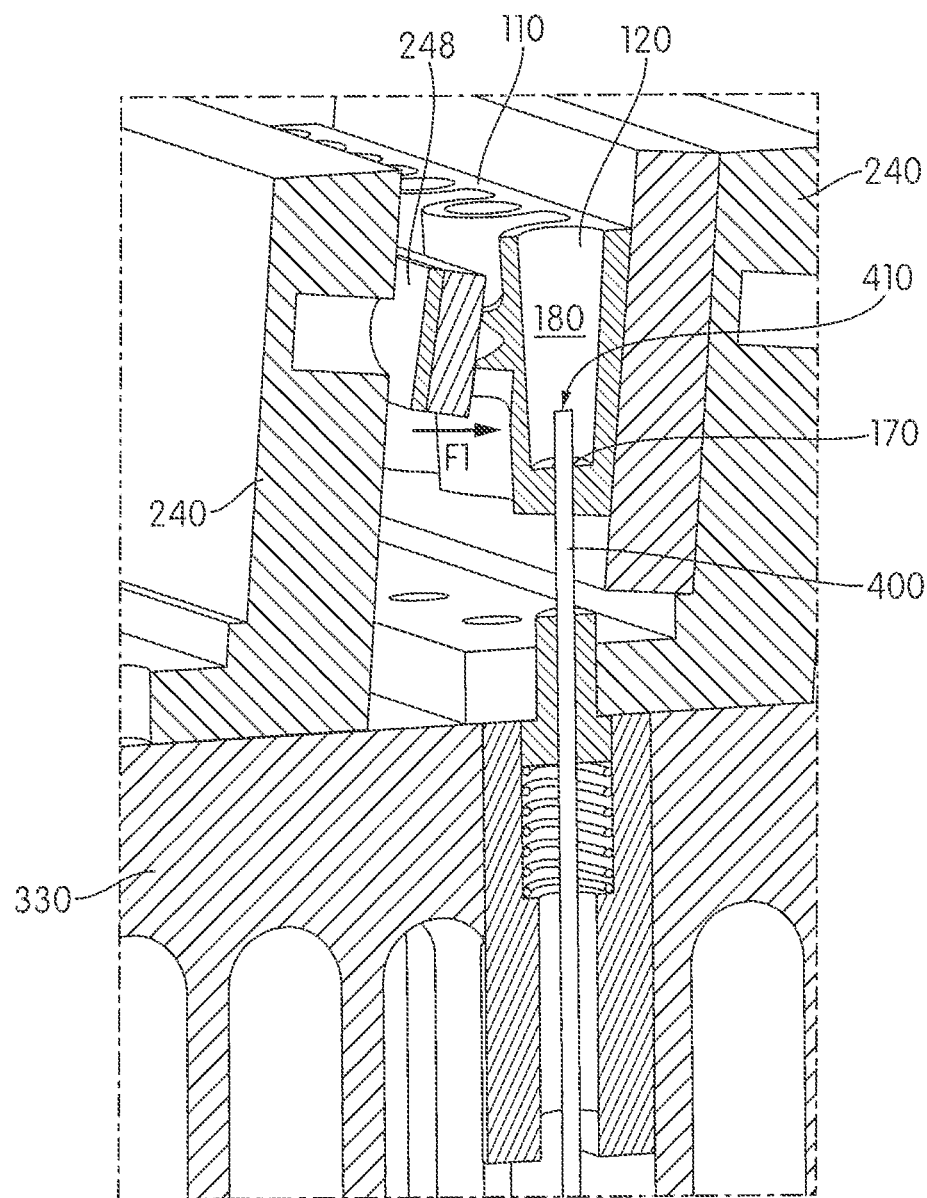
FIGS. 9A-9C are pictorial diagrams showing movement of the optical fibers of the apparatus of the present disclosure and the forces associated therewith prior to and after seating receptacles within the receptacle wells of a receptacle holder.
Figure 9B:
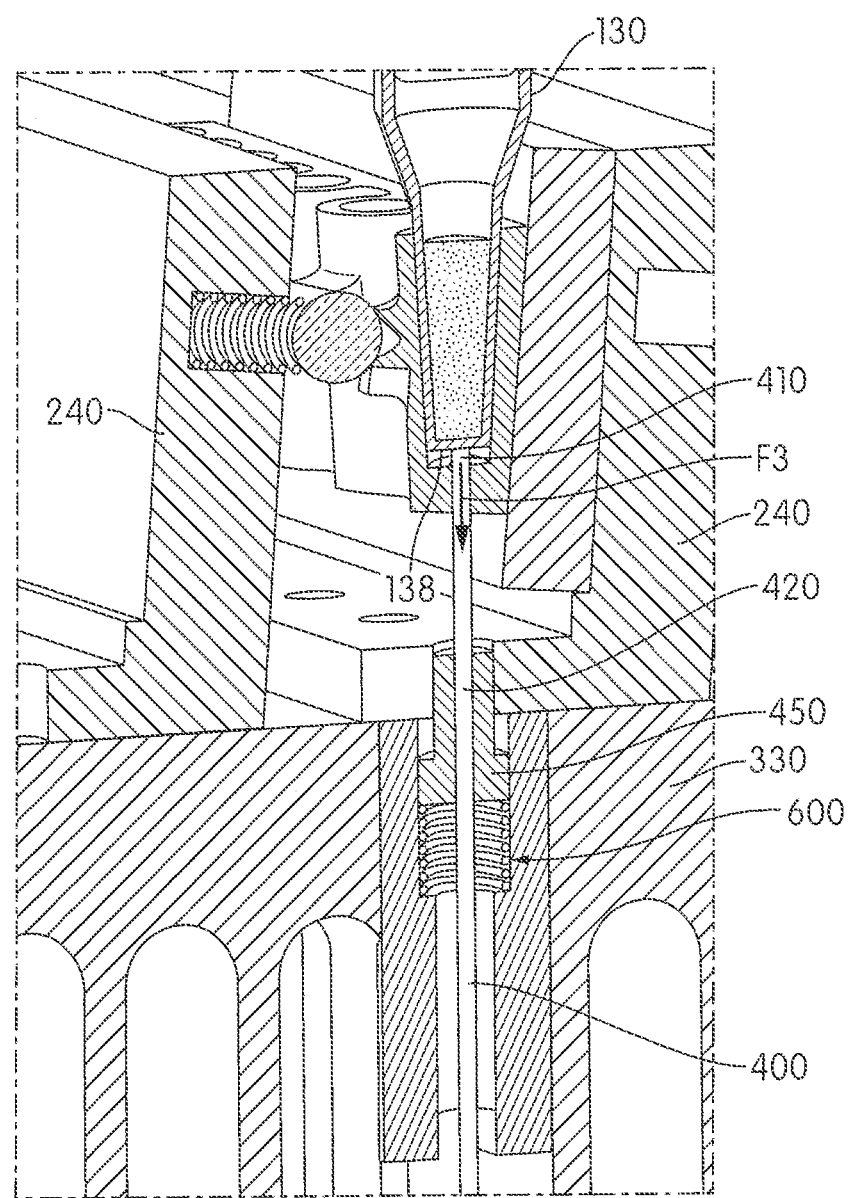
Figure 9C:
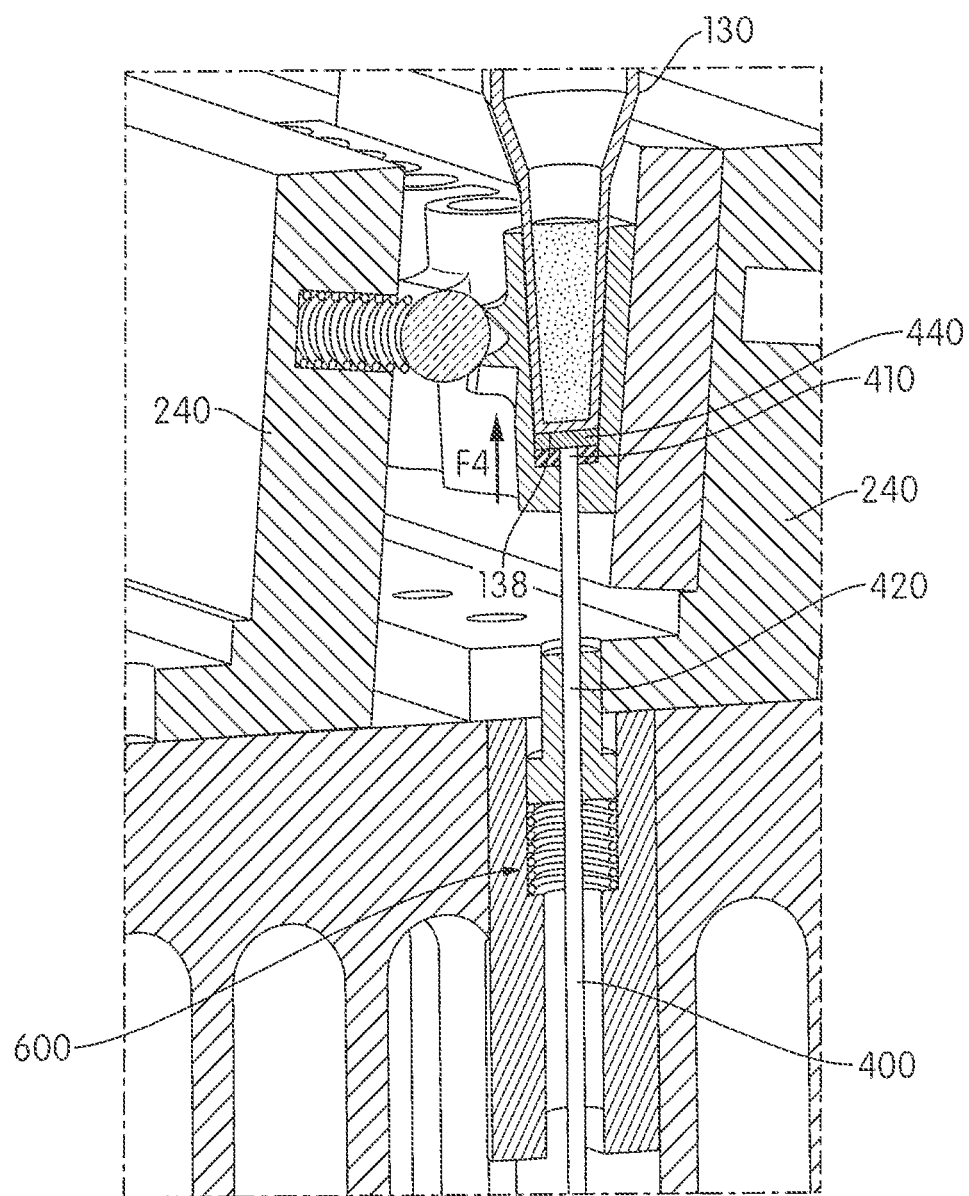
Figure 10:
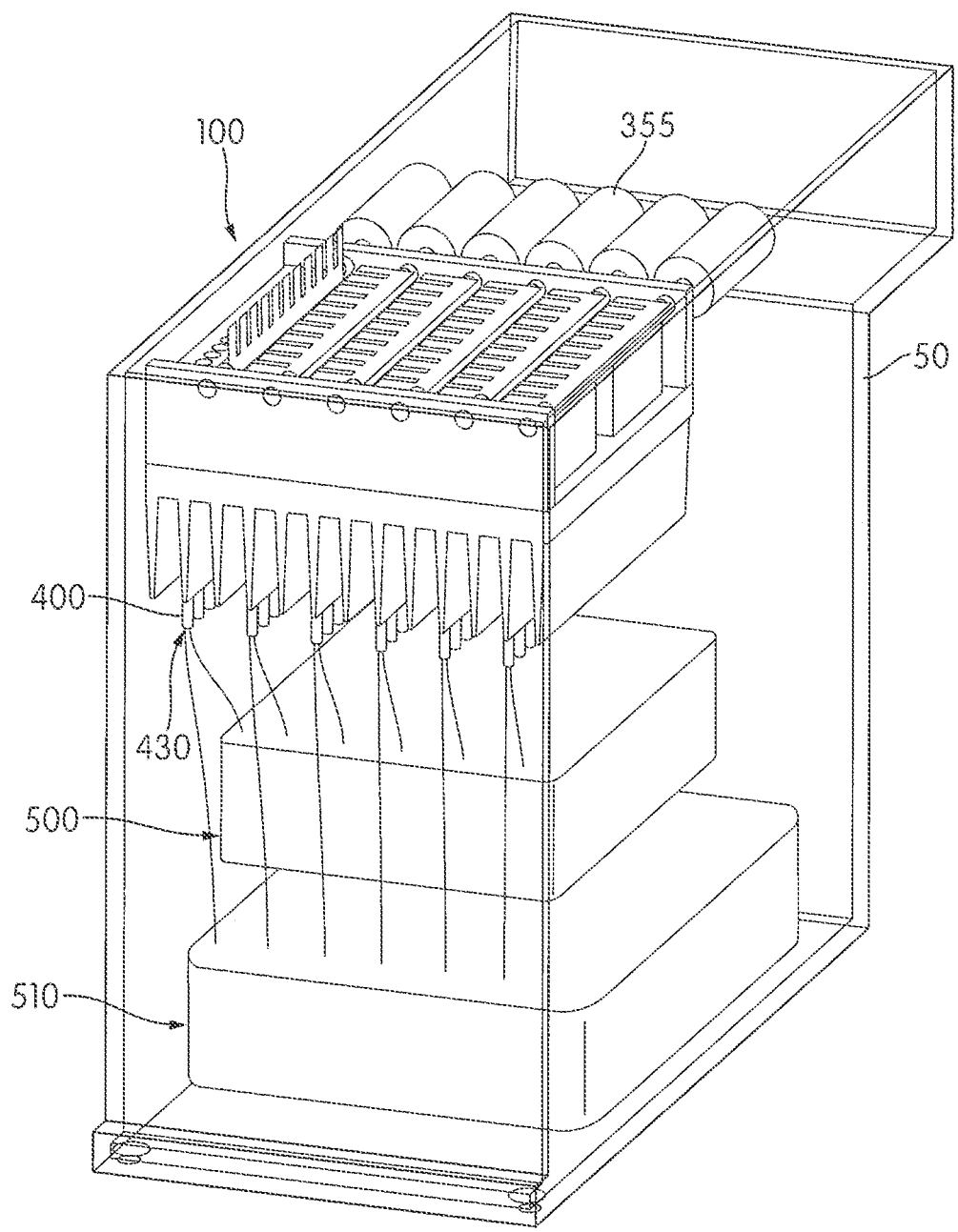
FIG. 10 is a pictorial diagram showing an apparatus in optical communication with an excitation signal source and/or an emission signal detector within a housing of an instrument for performing a biochemical assay.

With reference now to FIGS. 9A-9C, the apparatus 100 further includes a plurality of (i.e., more than one) optical fibers 400 to provide optical communication of a receptacle well with at least one of an excitation signal source 500 and an emission signal detector 510 (see FIG. 10). In one embodiment, the apparatus 100 includes one optical fiber 400 per receptacle well 120. Thus, when the apparatus 100 includes ten receptacles wells 120, at least ten optical fibers 400 will be provided to establish optical communication between the receptacle well 120 and one or more excitation signal sources 500 and/or one or more emission signal detectors 510.

As used herein, an "optical fiber" refers to a flexible, transparent fiber made of glass or plastic that functions as a waveguide to transmit light between the two ends (i.e., the first end and the second end) of the fiber. Typically, optical fibers include a transparent core surrounded by an opaque cladding material with a lower index of refraction and low to no autofluorescence characteristics. It should be understood that an optical pathway or assembly comprising the optical fiber may optionally include one or more filters, lenses, aspheres, etc., to modify and/or focus and excitation or emission signals passing therethrough. Optionally, the apparatus 100 may include an optical interface 440 between the first end 410 of each optical fiber 400 and the receptacle 130 (see FIG. 9C). Such optical interface 440 may include a filter, lens, asphere, nose, cap, or any other element having desired optical properties. However, it should be understood that in various embodiments, the interface 440 is not, and/or does not function as a lens. Exemplary interfaces 440 useful in the apparatus include, but are not limited to, glass or plastic balls, noses or caps covering the first end 410 of the optical fiber 400, or any suitable optically clear material.

The first end 410 of each of the plurality of optical fibers 400 is disposed outside, within, or extending through a through-hole 170 of the receptacle well 120, thereby providing optical communication with a receptacle well 120, and/or a receptacle 130 disposed within the receptacle well 120. When disposed within the receptacle well 120, as shown in FIG. 9A, the first end 410 of the optical fiber 400 may be moveable within the through-hole 170 of the receptacle well 120 relative to the inner surface 180 thereof. A variety of means of movement of the first end 410 of the optical fiber 400 within the through-hole 170 are contemplated. For example, the first end 410 of the optical fiber 400 may extend into the receptacle well 120, and when a receptacle 130 is placed within the well 120, the receptacle 130 contacts the first end 410 of the optical fiber 400, thereby providing optical communication between the receptacle 130 and the optical fiber 400. In an exemplary embodiment, the presence of a receptacle 130 within the receptacle well 120 will cause the optical fiber 400 to move within the through-hole 170 (e.g., through the application of a direct force) in a direction opposite from the inner surface 180 of the receptacle well 120 such that the receptacle 130 can make maximal contact with the inner surface 180 of the receptacle well 120 while maintaining optical communication with the optical fiber 400, as shown in FIG. 9B. In another embodiment, the downward force F2 exerted by the cover 350 and/or the flexible extensions 360 of the cover 350 onto at least a portion of a receptacle 130 disposed within a receptacle well 120 causes the optical fiber 400 to move within the through-hole 170 when the receptacle 130 contacts the optical fiber 400. In such embodiments, the receptacle 130 may apply a force F3 to the first end 410 of optical fiber 400 in substantially the same direction as the force F2 being applied to the receptacle, which is disposed within the well such that the end 410 of the optical fiber 400 moves within the well 120.

As is known in the art, optical fibers are rigid members, thereby having a certain amount of inherent resilience to movement. Thus, one of skill in the art would understand that optical fibers useful in the apparatus 100 should have sufficient rigidity to resist bending or otherwise deforming within the receptacle holder 120 upon application of force F3 onto the first end 410 thereof. Alternatively, a flexible optical fiber 400 may be utilized, but the first end 410 of the optical fiber 410 may be surrounded or protected by a rigid ferrule 450, for example, that optionally moves within the through-hole in response to the application or release of force F3.

Often, the first end 410 of each of the plurality of optical fibers 400, or an area 420 proximal to the first end 410 of each of the plurality of optical fibers 400, is connected, directly or indirectly, to a respective through-hole 170 of a receptacle well 120 with a resilient element 600. The resilient element 600 thereby compresses and/or deforms as the optical fiber 400 moves within the through-hole 170 and returns to its uncompressed and/or original form when the optical fiber 400 returns to its rest position to thereby moderate movement of optical fiber 400. As used herein, the "rest position" of an optical fiber refers to the position of the first end 410 thereof when no receptacle is present within the receptacle well and/or when no downward force F2 is exerted by the cover 350 onto at least a portion of a receptacle 130 disposed within the receptacle well 120. Exemplary resilient elements include, but are not limited to, springs, plastics, opened- or closed-cell foams, rubbers, dampers, pneumatic elements, hydraulic elements, electromagnetic elements, or combinations thereof.

One of skill in the art would understand that the inherent resilience/rigidity of the optical fiber 400 should be taken into consideration when selecting a resilient element 600 for use in the apparatus 100 to avoid having the optical fiber's inherent rigidity interfere with the ability of its movement within the through-hole 170. Thus, in frequent embodiments, each optical fiber 400 in the apparatus 100 has one or more dedicated resilient element(s) 600. Also, in frequent embodiments, two or more optical fibers 400 are in contact with a single resilient element 600 that permits individual or coordinated movement of the two or more optical fibers 400.

In yet another exemplary embodiment, the movement of the optical fiber 400 within the through-hole 170 of the receptacle well 120 is associated with the movement of the cover 350 of the apparatus 100. For example, in such embodiments the optical fiber 400 may be disposed outside, within, or extending through a through-hole 170 of the receptacle well 120 (as shown in FIG. 9A). Here the optical fiber 400 may, for example, be in moveable connection with the motor 355 that actuates the cover 350 such that the same motor 355 actuates movement of the optical fiber 400 within the through-hole 170. Alternatively, the optical fiber 400 may, for example, be in moveable connection with a motor (not shown) that is different than the motor 355 that actuates the cover 350, but the action of the motors on the cover 350 and optical fiber 400 may be coordinated such that the optical fiber 400 moves within the through-hole 170 in a time period that corresponds to the movement of the cover 350. This corresponding time period may comprise an overlapping time period or distinct, but associated, time periods. For example, the fiber 400 may move at the same time as the cover 350, the fiber 400 may move during only a portion of the time the cover 350 is moving, or the fiber 400 may move during a time that is before or after movement of the cover 350. In frequent, non-overlapping time period embodiments, before the cover 350 begins to move toward the closed position, the first end 410 of the optical fiber 400 may move within the through-hole 170 toward the inner surface 180 of the receptacle well 120. Alternatively, in other frequent, non-overlapping time period embodiments, before the first end 410 of the optical fiber 400 begins to move toward the inner surface 180 of the receptacle well 120, the cover 350 moves toward the closed position. Often, however, the movement of the optical fiber 400 and the cover 350 is coordinated such that the first end 410 of the optical fiber 400 moves toward the inner surface 180 of the receptacle well 120 after the cover 350 has begun to move and is approaching a closed position. In such embodiments, the first end 410 of the optical fiber 400 can be actuated to move towards the interior of the receptacle well 120 at the beginning of the movement of the cover 350 away from the closed position, or at another time period.

In another exemplary embodiment, the rest position of the first end 410 of the optical fiber 400 is below the inner surface 180 of the receptacle well 120. In other words, the first end 410 of the optical fiber 400 is at rest within the through-hole 170 of the receptacle holder 110. In such an embodiment, the first end 410 of the optical fiber 400 is therefore moved towards the interior of the receptacle well prior to, during, or after the cover 350 is moved to a closed position in order to bring the first end 410 into contact with at least a portion of the receptacle 130 disposed within a receptacle well 120, or otherwise positioned close to, but not in direct contact with, a portion of the receptacle 130 in order to establish optical communication therewith. As discussed above, the optical fiber 400 may, for example, be in moveable connection with the motor 355 that actuates the cover 350 such that the same motor 355 actuates movement of the optical fiber 400 within the through-hole 170. Alternatively, the optical fiber 400 may, for example, be in moveable connection with a motor (not shown) that is different than the motor 355 that actuates the cover 350, but the action of the motors on the cover 350 and optical fiber 400 may be coordinated such that the optical fiber 400 moves within the through-hole 170 in a time period that corresponds to the movement of the cover 350.

In yet another exemplary embodiment, movement of the optical fiber 400 within through-hole 170 (either into or out of the interior of receptacle well 120) may be actuated through a mechanical connection to the rigid rotatable member 352 of the cover 350. For example, a geared or cammed mechanical connection (not shown) with the rigid rotatable member 352 may be used to coordinate movement of the first end 410 of the optical fiber 400 into and away from the interior of the receptacle well 120 as the cover 350 is moved into the opened or closed position. As such, the optical fiber 400 of the apparatus 100 may move into and out of the receptacle well 120 in conjunction with the opening and closing of the cover 350 of the apparatus 100.

In certain embodiments, placement of a receptacle 130 within the receptacle well 120 generally will not cause the optical fiber 400 to move within the through-hole 170. However, as discussed above, the force F2 exerted by the cover 350 onto at least a portion of the receptacle 130 will prevent movement of the receptacle 130 within the receptacle well 120, and allow for optical communication between the receptacle 130 and the optical fiber 400, while maintaining maximal contact between the receptacle 130 and the inner surface 180 of the receptacle well 120. In embodiments wherein the rest position of the optical fiber 400 results in the first end 410 thereof being disposed below the inner surface 180 of the receptacle well 120, force F2 maintains receptacle 130 in the seated position within receptacle well 120 even after the actuated movement of the optical fiber 400 into the interior of the receptacle well 120. As should be understood, actuation of optical fiber 400 into contact with receptacle 130 often exerts a force F4 (FIG. 9C) onto the closed bottom end 138 of the receptacle 130. In the absence of force F2 exerted by the cover 350 onto at least a portion of the receptacle 130, force F4 may dislodge or otherwise impair optimal contact of the receptacle 130 with the inner surface 180 of the receptacle well 120. Therefore, in such embodiments, force F4 generally has the same magnitude, or has a magnitude smaller than, force F2 or force F3.

Methods of Establishing Optical Communication

Figure 11A:
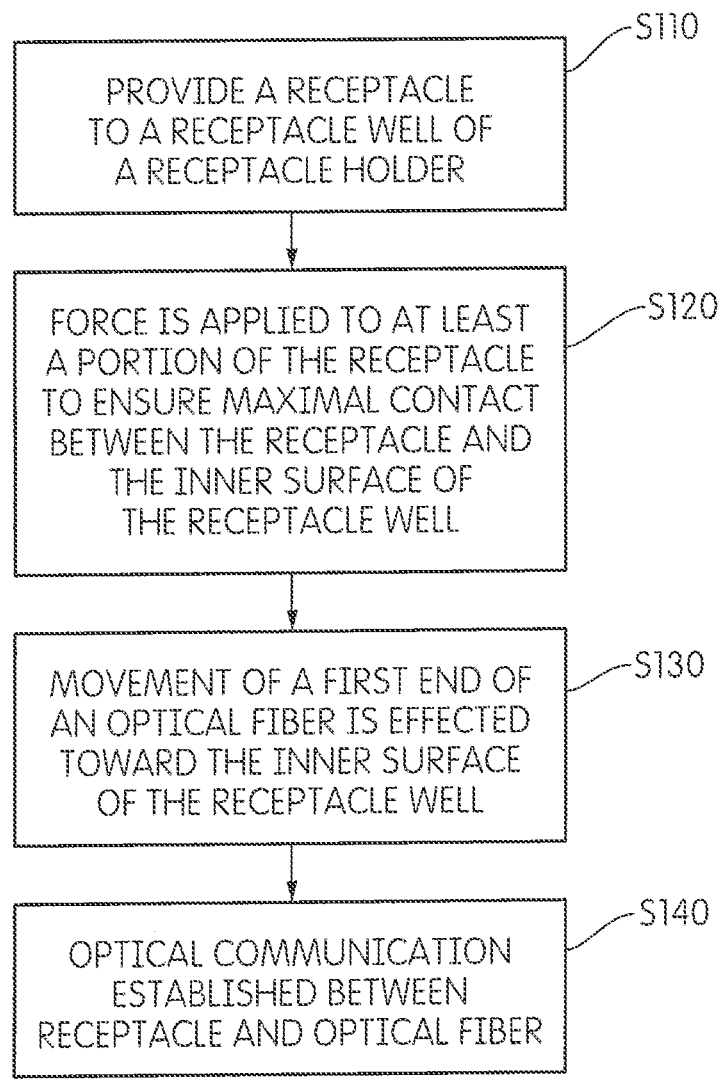
FIGS. 11A and 11B are flow charts showing exemplary steps involved in a method for establishing optical communication between a receptacle and an excitation signal source and/or an emission signal detector within a housing of the apparatus while allowing maximal contact between the surface of the receptacle well and the receptacle.

In another aspect, disclosed herein is provided a method for establishing optical communication between a receptacle and an excitation signal source and/or an emission signal detector within a housing of the apparatus while allowing maximal contact between the surface of the receptacle well and the receptacle (FIG. 11A). As discussed in detail above, the method includes providing a receptacle 130 to a receptacle well 120 of a receptacle holder 110 (step S110). Thereafter, a force F2 is applied to the receptacle 130 or at least a portion of the receptacle 130, such that the receptacle 130 fits snugly within the receptacle well 120, thereby allowing maximal contact between the inner surface 180 of the receptacle well 120 and the receptacle 130 (step S120). While force F2 is being applied to at least a portion of the receptacle 130, movement of a first end 410 of an optical fiber 400 is effected toward the inner surface 180 of the receptacle well 120 (step S130). In such embodiments, the receptacle 130 may apply a force F3 to the optical fiber 400 in substantially the same direction as the force F2 being applied to the receptacle 130, to the first end 410 of the optical fiber 400, which is disposed within the receptacle well 120 such that optical communication is established between the bottom 138 of the receptacle 130 and the first end 410 of the optical fiber 400 (step S140). As discussed above, movement of the first end 410 of the optical fiber 400 is coordinated with movement of cover 350 into the closed position. As such, the method may further include movement of the cover 350 in coordination with the movement of the first end 410 of the optical fiber 400.

Figure 11B:
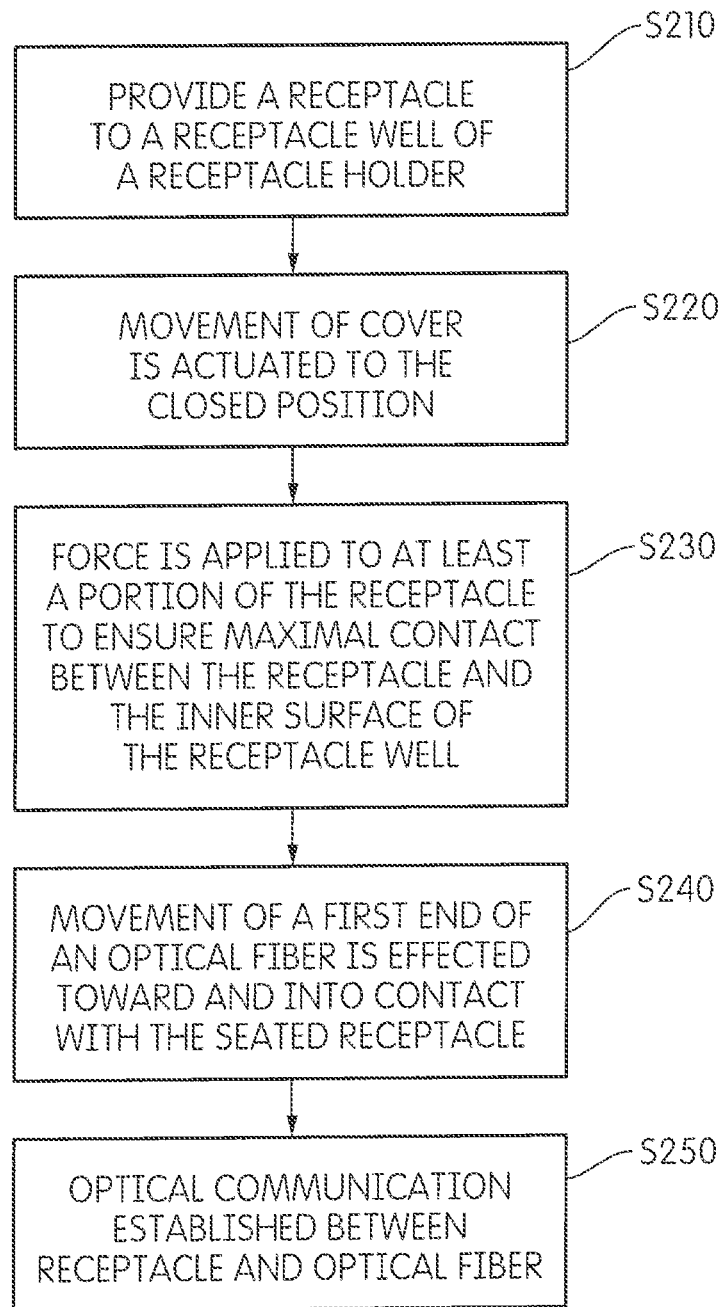

Another exemplary embodiment of the method for establishing optical communication between a receptacle and an excitation signal source and/or an emission signal detector within a housing of the apparatus while allowing maximal contact between the surface of the receptacle well and the receptacle is shown in FIG. 11B. In this embodiment, the method includes providing a receptacle 130 to a receptacle well 120 of a receptacle holder 110 (step S210). Thereafter, a cover 350 is moved into the closed position (step S220), thereby exerting a force F2 onto the receptacle 130 or at least a portion of the receptacle 130, such that the receptacle 130 fits snugly within the receptacle well 120, thereby allowing maximal contact between the inner surface 180 of the receptacle well 120 and the receptacle 130 (step S230). Prior to, during, or after movement of the cover 350 into the closed position, movement of a first end 410 of an optical fiber 400 is effected toward and into contact with the seated receptacle 130 (step S240). Upon contact of the first end 410 of the optical fiber 400 with the closed end 138 of the receptacle 130, force F4 is exerted by the first end 410 onto the receptacle 130. In such embodiments, the receptacle 130 may apply a force F3, which is greater than force F4, onto the first end 410 of the optical fiber 400 in substantially the same direction as the force F2. As such, optical communication is established between the first end 410 of the optical fiber and the receptacle 130, while ensuring maximal contact between the receptacle 130 and the inner wall 180 of the receptacle well 120 (step S250). As discussed above, movement of the first end 410 of the optical fiber 400 is coordinated with movement of cover 350 into the closed position.

Often, the first end 410 of each of the plurality of optical fibers 400, or an area 420 proximal to the first end 410 of each of the plurality of optical fibers 400, is connected, directly or indirectly, to a respective through-hole 170 of a receptacle well 120 with a resilient element 600, as discussed above. The resilient element 600 thereby compresses and/or deforms as the optical fiber 400 moves within the through-hole 170 and returns to its uncompressed and/or original form when the optical fiber 400 returns to its rest position.

Stripper Plate

Figure 12A:
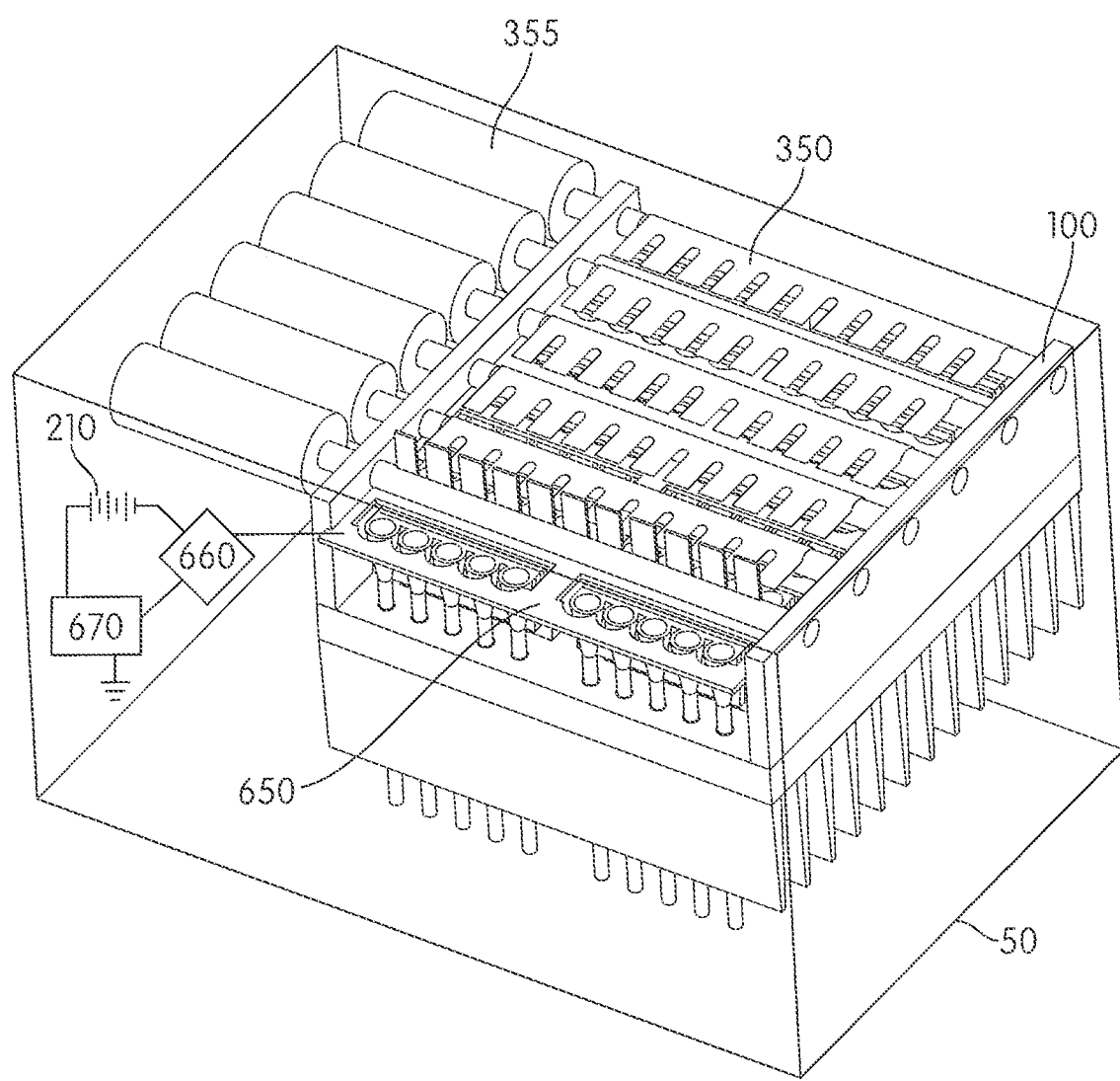
FIGS. 12A-12D are pictorial diagrams showing exemplary steps involved in loading receptacles into the receptacle wells of a receptacle holder of an apparatus of the present disclosure.
Figure 12B:
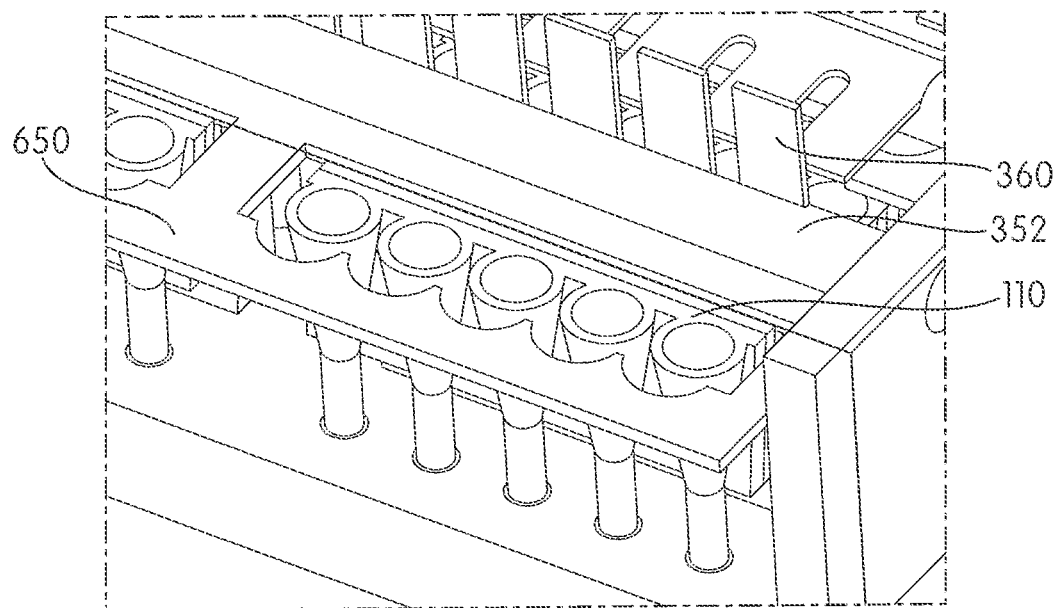
Figure 12C:
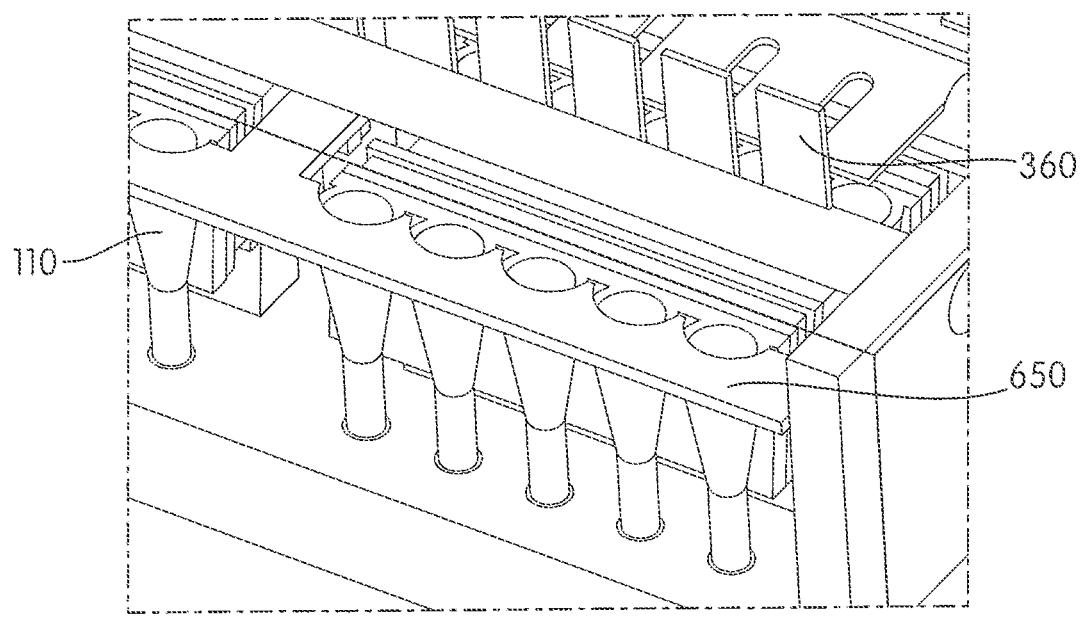
Figure 12D:
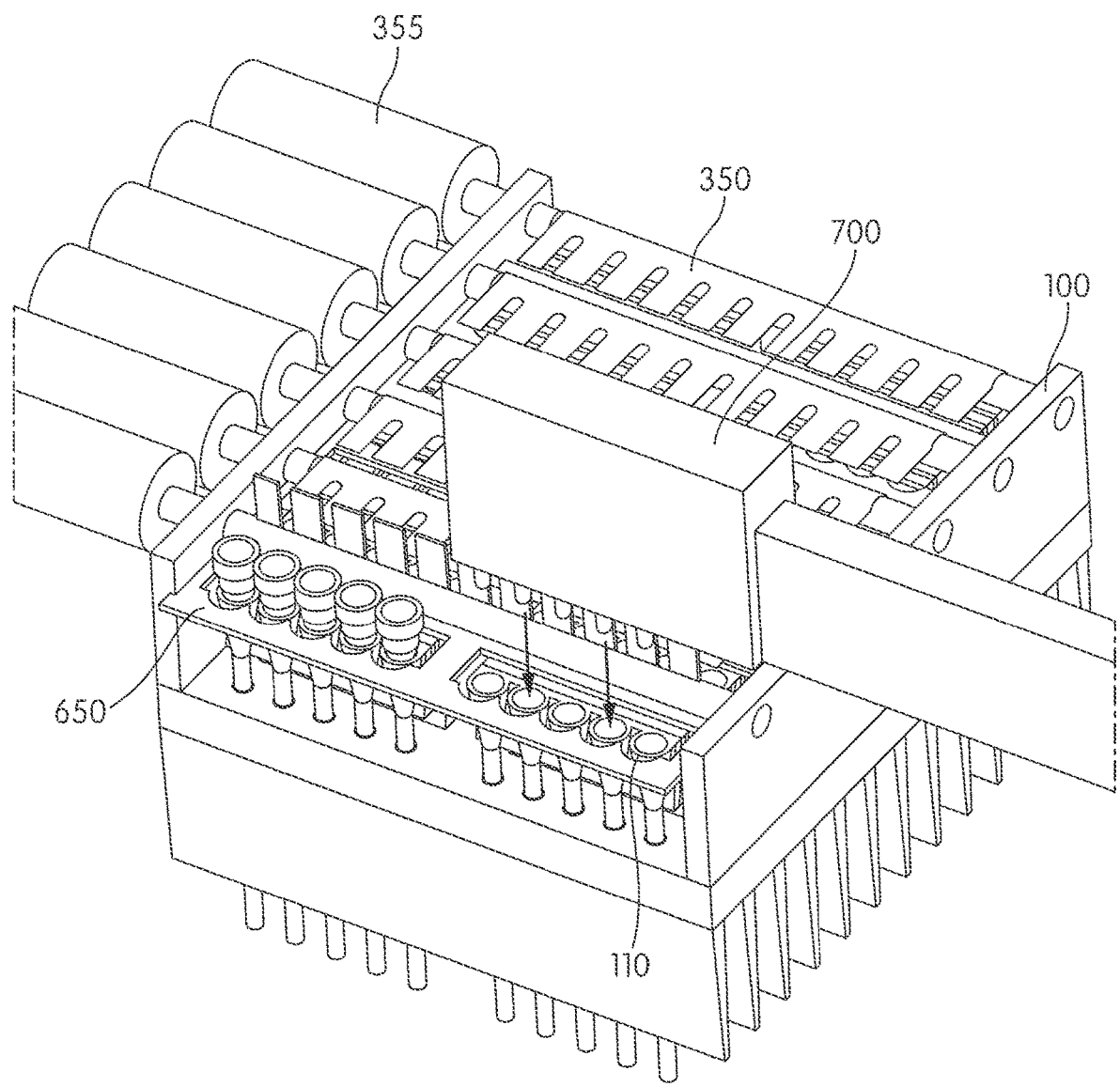

With reference now to FIGS. 12A-12D, the apparatus 100 may further include one or more stripper plates 650 mounted in moveable association with the receptacle holder 110. Like the cover 350, the stripper plate 350 is movable between an opened and closed position, which in reference to the stripper plate 650, will be referred to as the "unlocked position" and the "locked position." When in the unlocked position (FIG. 12B), the stripper plate 650 permits transfer to and removal of a receptacle 130 into or out of a receptacle well 120. When in the locked position (FIG. 12C), the stripper plate 650 inhibits removal of a receptacle 130 disposed within a receptacle well 120, thereby permitting a receptacle transport mechanism 700, such as a pipettor or pick-and-place robot, to withdraw from receptacle 130 (FIG. 12D). It should be understood that when in the locked position, the stripper plate 650 does not inhibit access to the top of the receptacle 130 by a receptacle transport mechanism 700 used to deliver to and/or remove receptacles 130 but will prevent removal of the receptacle 130. Thus, removal of the receptacle 130 may only occur, if the stripper plate 650 is present, when the stripper plate 650 is in the unlocked position.

When present, the stripper plate 650 may be made from any rigid material suitable for removing a receptacle 130 from a receptacle transport mechanism 700. Exemplary materials from which the stripper plate may be made include, but are not limited to, beryllium copper, spring steel, aluminum, titanium, plastic, or any suitable rigid material.

In various embodiments, the apparatus 100 may include a single stripper plate 650 in moveable association with all receptacle holders 110, or it may include a single stripper plate 650 for each row of receptacle holders 110, or it may include a single stripper plate 650 for each individual receptacle holder 110. Movement of the stripper plate 650 may be actuated by an electric motor 660 disposed either within the apparatus 100 or within the housing 50 in which the apparatus is located. When more than one stripper plate 650 is provided in the apparatus, each stripper plate 650 may be actuated by its own motor 660, or more than one stripper plate 650 may be actuated by the same motor 660. As such, when the apparatus 100 includes more than one stripper plate 650, each stripper plate 650 may move independently of the next and/or more than one stripper plate 650 may be moved simultaneously. The electric motors 660 effecting movement of the one or more stripper plates 650 are electrically connected to a controllable power source 210 for applying a current thereto. Control of the power source 210 can be carried out by an appropriately programmed processor 670 (such as a computer) which may receive signals from another processor that controls the automated process steps involved with thermal cycling processes.

As with movement of the optical fibers 400 discussed above, movement of the stripper plate 650 between the locked and unlocked positions may be associated with the movement of the cover 350 of the apparatus 100. For example, in such embodiments the stripper plate 650 may be disposed in moveable connection with the motor 355 that actuates the cover 350 such that the same motor 355 actuates movement of the stripper plate 650 as necessary. Thus, the action of the motors on the cover 350 and stripper plate 650 may be coordinated such that the stripper plate 650 moves in a time period that corresponds to the movement of the cover 350. This corresponding time period may comprise an overlapping time period or distinct, but associated, time periods. For example, the stripper plate 650 may move at the same time as the cover 350, the stripper plate 650 may move during only a portion of the time the cover 350 is moving, or the stripper plate 650 may move during a time that is before or after movement of the cover 350. However, movement of the stripper plate must be timed such that the receptacle transport mechanism 700 may withdraw from receptacle 130 without interfering with the movement of the cover 350.

In other exemplary embodiments, the stripper plate 650 may be movable between the locked and unlocked positions by any suitable mechanical element included in the apparatus. In an exemplary embodiment, the stripper plate 650 is hingedly attached to the apparatus 100 so as to enable movement between the locked and unlocked positions. Attachment points include, but are not limited to, any of the one or more supports of the apparatus or any suitable location within a housing 50 containing the apparatus 100. In another embodiment, the stripper plate 650 is slidingly attached to opposing sides of a support of the apparatus 100. For example, the stripper plate 650 may laterally slide in a direction perpendicular to the orientation of the rows (101-106) of receptacle holders 110. While a stripper plate may be utilized in certain embodiments described herein, it is often not incorporated as a feature when the receptacle transport mechanism 700 is provided with a receptacle release such as a tip stripper, ejection mechanism, or other receptacle release mechanism known in the art.

Second Exemplary Embodiment of the Apparatus

With reference now to FIGS. 14A-14D and 16, there is provided a second exemplary embodiment of the apparatus 800 described herein. The description will be provided based on the differences from the first exemplary embodiment discussed above. As such any reference to like elements should be understood as described above.

As in the previous exemplary embodiment, the apparatus 800 includes one or more (i.e., 1, 2, 3, 4, 5, 6, 7, 8, 9, 10, 11, 12, or any whole number between 1 and 20, or more) receptacle holders 110 (see also FIG. 3). When multiple receptacle holders 110 are provided in an apparatus described herein, each receptacle holder 110 disposed within the apparatus may be disposed in alignment with one another to facilitate the automated processing steps involved in nucleic acid amplification assays. Such an apparatus 800 may include a housing 50 (see FIGS. 2 and 4) within which the one or more receptacle holders 110 are located. The housing 50 may be made from any suitable structural material such as, for example, plastic or metal.

Figure 14A:
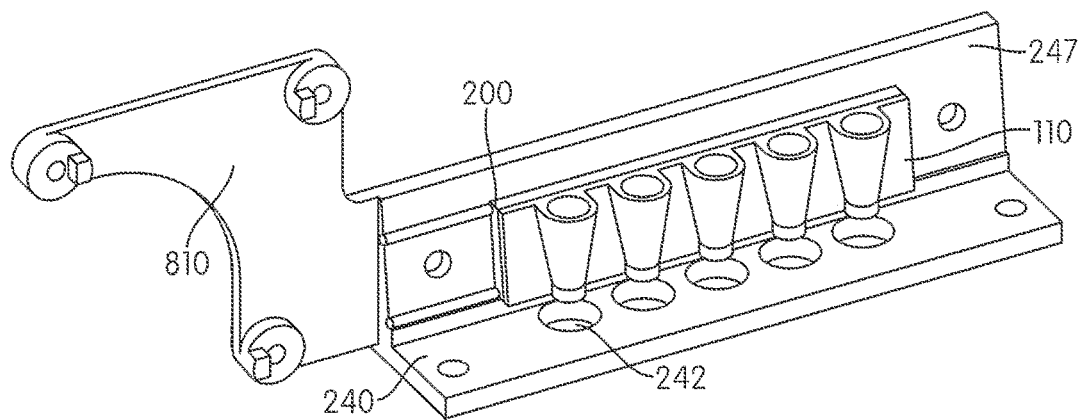
FIGS. 14A-14D are pictorial diagrams showing a second exemplary embodiment of an apparatus of the present disclosure.
Figure 14B:
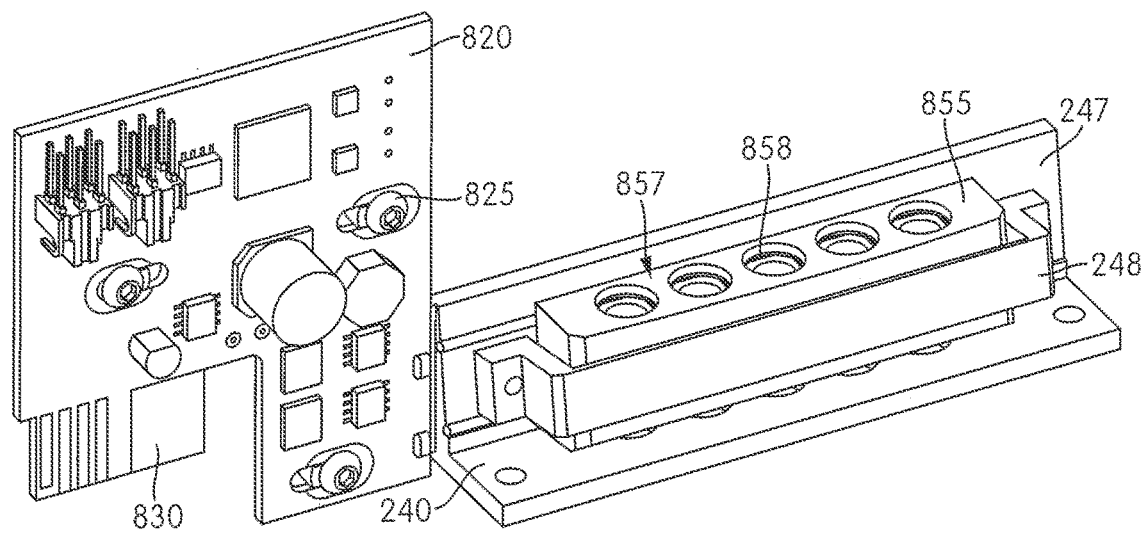

As shown in FIG. 14A, the upright portion 247 of the support 240 includes a mount 810 projecting from a third side thereof, for attachment to a controller board 820 shown in FIG. 14B. Attachment of the controller board 820 to the mount 810 of the support 240 may be accomplished by any means known in the art. For example, the controller board 820 may be fixedly attached by rivets or screws 825. Often, the attachment is by way of a mechanism that permits independent lateral movement between the support 240 and the controller board 820. Such an attachment may be by way of the use of shoulder screws or machining of the attachment points in the support 240 such that the controller board can move laterally over them regardless of the type of securing means that is utilized, including standard-threaded screws. Such lateral movement of the controller board 820 facilitates the mounting of the support 240/controller board 820 unit to the heat sink 330, and allows for proper alignment of through-holes 242 of the support 240 with through-holes 332 of the heat sink 330, thereby providing optimal positioning of optical fibers 400 for examination of the contents of a receptacle well 120.

The controller board 820 may include logic and control circuitry for performing one or more of the motorization and temperature control functions described above. In various embodiments, the controller board 820 includes at least one electronic connection point 830 for electrical connection to a second controller board 835 (see FIG. 16) disposed on the apparatus 800. In frequent embodiments, the entire unit (or apparatus), including the circuitry on the controller board 820, depicted in FIG. 14B represents an independently calibrated unit that can be utilized when plugged into a power source and oriented in communication with a detection system, such as an optical system or another detection system. In such embodiments, the controller board 820 has been configured to operate with the installed elements identified in FIGS. 14A-14D, with or without the primary or secondary cover 840/850, or any other cover means. In essence, the unit exemplified in FIG. 14B may be operated and utilized as a "plug-and-play" type of apparatus, whereby it can be installed, removed, or replaced with a different unit, at will, without the need for independent calibration of the overall detection system after installation. As discussed above, disposed between the receptacle holder 110 and the upright portion 247 of the support 240 is a thermal element 200, such as a "Peltier device." A compressive housing 855 having a top surface 857 is configured for securable attachment over the receptacle holder 110. Disposed in the top surface 857 of the compressive housing 855 are a plurality of through-holes, each corresponding to and in alignment with a receptacle well 120 of the receptacle holder 110. One or more cross-braces 248 are mounted to the support 240 and exert a force F1 (FIG. 5B) onto a side surface of the compressive housing 855, which in turn exerts the force F1 onto the receptacle holder 110. The support 240 and compressive housing 855 may each be formed from a material having low thermal conductivity such as plastic. In certain embodiments, the material from which the support 240 and compressive housing 855 are formed may be the same material or may be different materials.

Figure 14C:
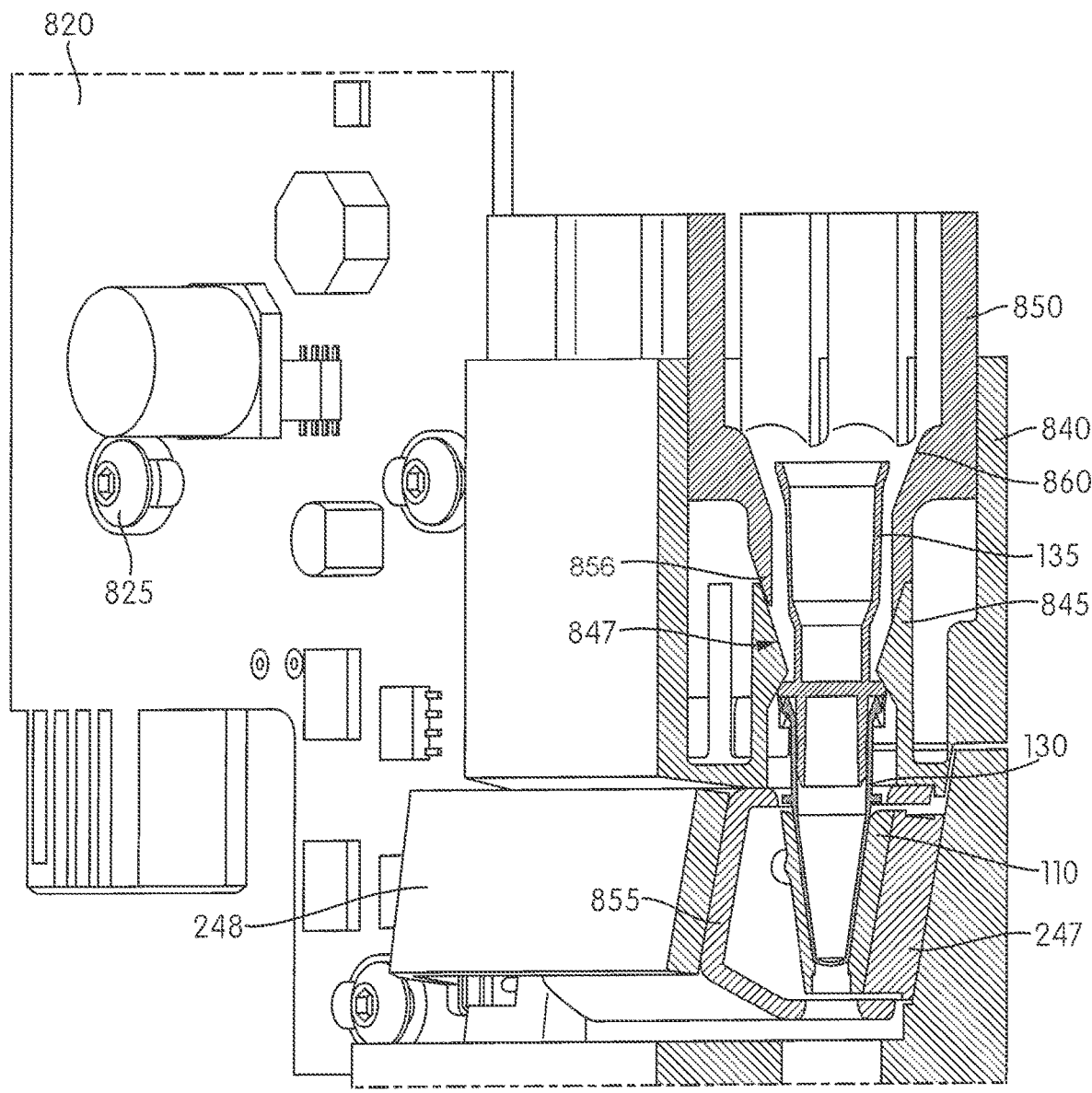
Figure 14D:
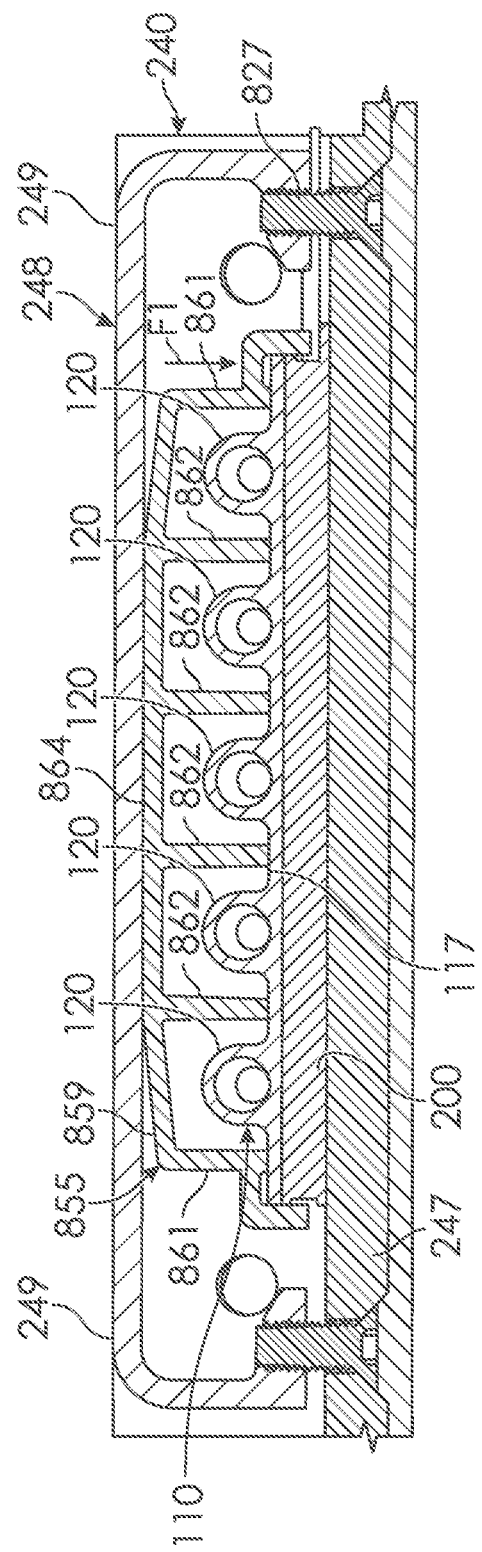

FIG. 14D depicts a top view of a portion of the apparatus 800 provided in FIGS. 14A-14C. In various embodiments, the compressive housing 855 has a side wall 864 with sloped ends 859 that are oriented toward the receptacle holder 110. The sloped ends 859 enhance the uniformity of the compressive force of the compressive housing 855 on the receptacle holder 110, while simplifying the compressive connection, installation ease, and serviceability of the unit. In this embodiment, screws 827 may be threaded through the upright portion 247 and into the cross-brace 248. When the screws 827 are tightened, the cross-brace 248 exerts a force on the outer surface of the side wall 864 (i.e., the surface facing away from the receptacle holder 110), and the outer ends 249 of the cross-brace 248 are pulled toward the upright portion 247, resulting in a bowed curvature (not shown) of the cross-brace 248 around the compressive housing 855. The sloping ends 859 permit cross-brace 248 bowing while enhancing the overall uniformity of the applied compressive force F1. The compressive housing 855 illustrated in FIG. 14D further includes a plurality of ribs, including end ribs 861 and intermediate ribs 862, extending from the inner surface of side wall 864 (i.e., the surface facing the receptacle holder 110) and contacting the front surface 117 of the receptacle holder 110 adjacent the receptacle wells 120. The end ribs 861 in the illustrated embodiment contact the receptacle holder 110 at locations outside the endmost receptacle wells 120, and the intermediate ribs contact the receptacle holder 110 between adjacent pairs of receptacle wells 120. One of skill in the art would appreciate that additional orientations and configurations of the cross-brace 248/compressive housing 855 connection could be provided without departing from the scope of the present disclosure.

Figure 16:
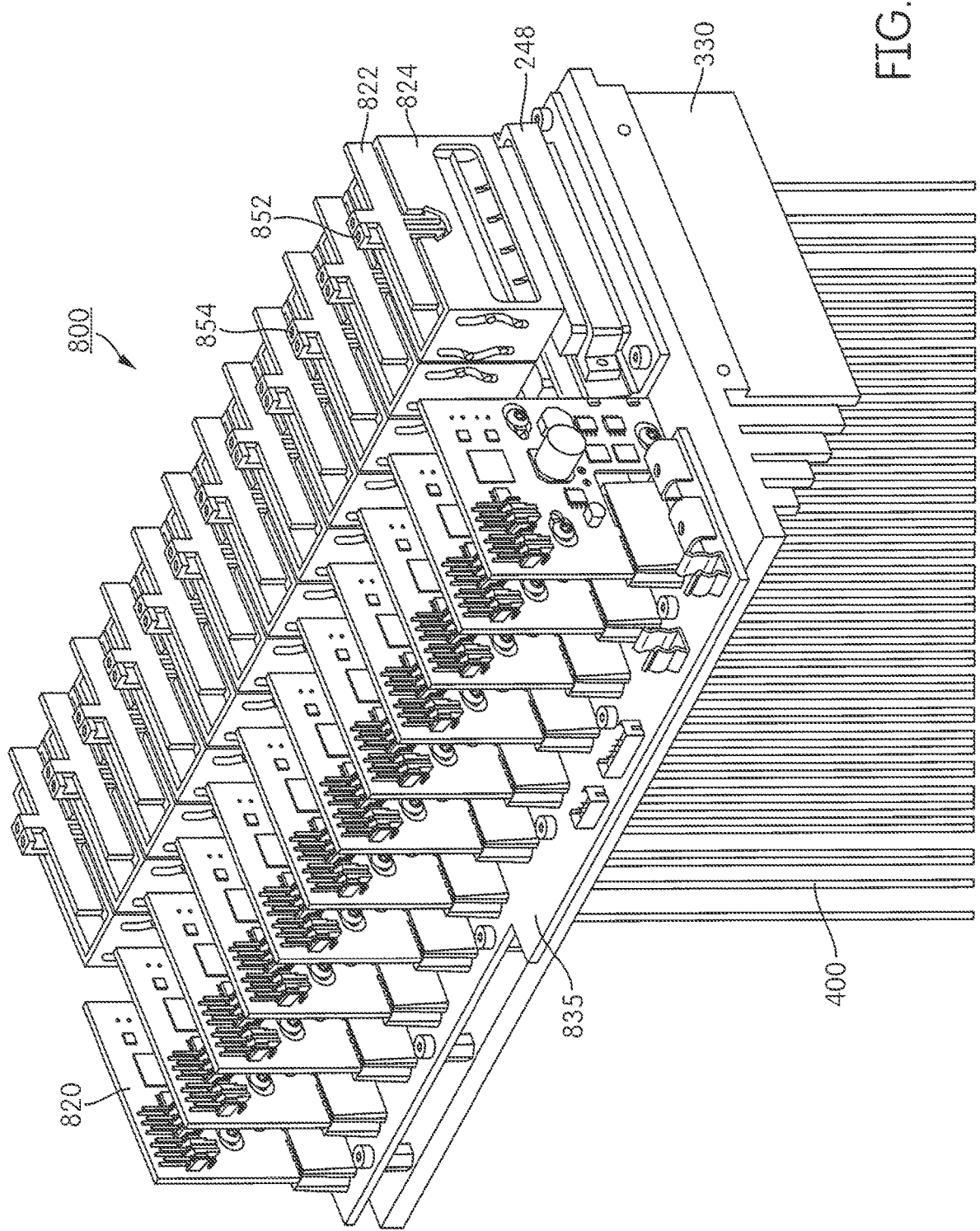
FIG. 16 is a pictorial diagram showing a perspective view of an alternative exemplary embodiment of the cover mechanism of the apparatus.

With reference now to FIG. 16, each support 240 may be a heat sink, may be in thermal communication with an individual heat sink 330, or may be in thermal communication with a single heat sink 330. Each heat sink 330 positioned in thermal communication with one or more supports 240 of the apparatus 800, may further include a plurality of through-holes 332 (see FIG. 7B) disposed in a surface thereof. Each through-hole 332 may be in direct alignment with the through-holes 242 of the support and/or the through-holes 170 at the bottom surface 160 of the receptacle holders 110 that are positioned in engagement therewith. Such through-holes 332 form a channel through which optical fibers and/or associated components, for example, may pass thereby providing optical communication between each receptacle well 120 and an excitation signal source and/or an emission signal detector, as discussed above.

As shown in FIG. 14C, the apparatus 800 may also include a primary cover 840 that is fixedly positioned over the receptacle holder 110. The primary cover 840 may be formed with one or more (i.e., 1, 2, 3, 4, 5, 6, 7, 8, 9, 10, or more) securing arms 845 in direct alignment with and circumscribing each receptacle well 120 of the receptacle holder 110. In certain embodiments, the primary cover 840 is formed with four securing arms 845 in direct alignment with and disposed in a surrounding arrangement with each receptacle well 120 of the receptacle holder 110. The securing arms 845 are configured for securable attachment to at least a portion of the receptacle or cap 135 that is attached to a receptacle 130. Such securable attachment is analogous to the force F2 exerted by the cover 350, as discussed above, for ensuring that the receptacle 130 fits snugly within the receptacle well 120, thereby allowing maximal contact between the inner surface 180 of the receptacle well 120 and the receptacle 130. The securing arms can be made of any suitable material, including plastic, metal, or a metal composite.

The apparatus 800 may further include a secondary cover 850 fixedly positioned over the primary cover 840. The secondary cover 850 may be formed with one or more (i.e., 1, 2, 3, 4, 5, 6, 7, 8, 9, 10, or more) releasing arms 856, each in direct alignment and in sliding contact with the securing arms 845 of the primary cover. In various embodiments, the securing arms 845 of the primary cover include an angled surface 847 upon which the corresponding releasing arm 856 of the secondary cover 850 may slide when actuated during an automated process. The secondary cover 850 may further include one or more (i.e., 1, 2, 3, 4, 5, 6, 7, 8, 9, 10, or more) actuators 860 that are fixedly connected to the releasing arms 856, and are positioned such that when a force is applied thereon, the force is transferred from the actuator 860 to the releasing arms 856, which in turn, press onto the angled surface 847 of the primary cover 840 and release the securable attachment to the cap 135 that is attached to a receptacle 130.

Figure 15C:
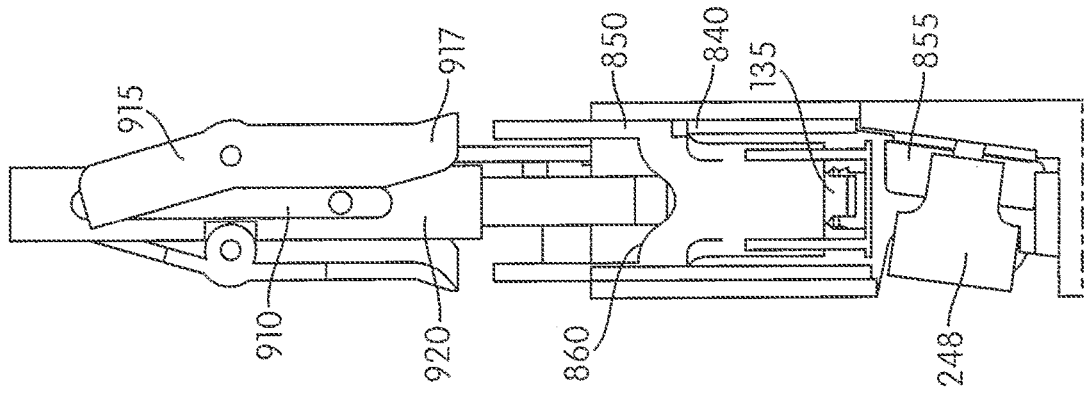
FIGS. 15A-15C are pictorial diagrams showing a modified pipettor for use as a receptacle transport mechanism within a system of the present disclosure.
Figure 15B:
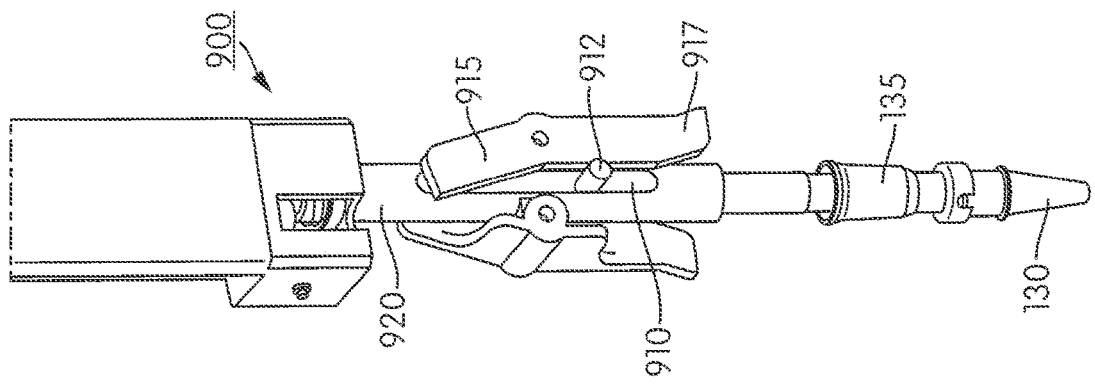
Figure 15A:
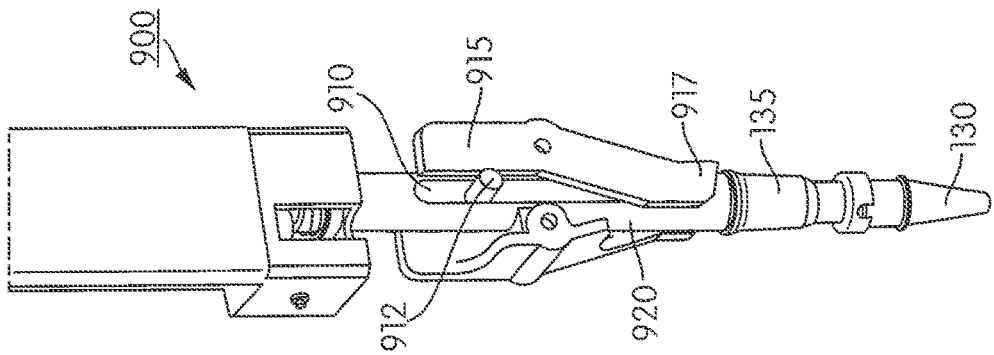

It is therefore contemplated that the housing 50 within which the apparatus 800 is located will include at least one modified pipettor 900, as shown in FIGS. 15A and 15B. As shown in FIG. 15A, the modified pipettor 900 is modified such that a plunger 910 is slidingly coupled to one or more limbs 915, which are hingedly attached to a body 920 of the modified pipettor 900. Thus, when the modified pipettor 900 causes the plunger 910 to be in a first position (as shown in FIG. 15A), the one or more limbs 915 are in a retracted position such that a lower portion 917 thereof are positioned in close proximity to the body 920. When the modified pipettor 900 causes the plunger 910 to be in a lowered second position (as shown in FIG. 15B), the one or more limbs 915 are then moved into an extended position such that the lower portions 917 thereof are moved away from the body 920.

This modified pipettor 900 is useful for engaging the secondary cover 850 and pressing on the secondary cover 850 in a downward movement that actuates the release of the securing arms 845 by the physical action of the releasing arms 856. When the releasing arms 856 are depressed in this manner, the securing arms 845 are pulled axially away from the receptacle 130 and cap 135, permitting its unencumbered release and lifting out by the pipettor. In such circumstances it is advantageous that the releasing arms 856 maintain contact with, and depress in a radially outward manner, the securing arms 845 for the time period required for the pipettor plunger 910 to frictionally engage the receptacle cap and to lift the receptacle and cap vertically clear of the securing arms 845.

FIG. 16 depicts an alternate embodiment of a cover mechanism 824 that is actuated by an automated pipettor or a modified pipettor 900, as described above. In this embodiment the end or plunger 910 of a pipettor 900 contacts and depresses a cover release mechanism 852, which opens the cover 822, permitting access of the receptacle 130 to the well 120. Once the receptacle 130 is placed in the well 120, the pipettor end or plunger is utilized to depress a cover securing mechanism 854, which causes a force to be exerted on the cap 135 and/or receptacle 130 which then is securely seated in the well 120. The force is analogous to the force F2 exerted by the cover 350, as discussed above, for ensuring that the receptacle 130 fits snugly within the receptacle well 120, thereby allowing maximal contact between the inner surface 180 of the receptacle well 120 and the receptacle 130. The cover 822 may be motor-actuated, as discussed above, may be actuated through one or more torsion springs disposed on the rigid rotatable member 352 (FIG. 8B) to which the cover 822 is fixedly attached, or may be actuated by a spring mechanism that causes the cover 822 to move vertically with respect to the receptacle holder 110. In various embodiments, the spring-loaded cover 822 may include a push-lock fastener, which may lock the spring-loaded cover 822 into the locked position. The push-lock mechanism may be directly or indirectly associated with the cover release mechanism 852 and/or the cover securing mechanism 854.

In certain embodiments, any of the apparatuses described herein will not include a cover or a mechanism to exert force F2 onto the capped receptacle 130. In such embodiments, the receptacle 130 fits snugly within the receptacle well 120, thereby allowing maximal contact between the inner surface 180 of the receptacle well 120 and the receptacle 130 without the need for a force F2.

In certain embodiments, any of the apparatuses described herein may include a cover but will not include a mechanism to exert force F2 onto the capped receptacle 130. In such embodiments, the cover does not contact the capped receptacle, as the receptacle 130 fits snugly within the receptacle well 120, thereby allowing maximal contact between the inner surface 180 of the receptacle well 120 and the receptacle 130 without the need for a force F2.

Use of the Apparatus in a Biochemical Assay

Figure 13:
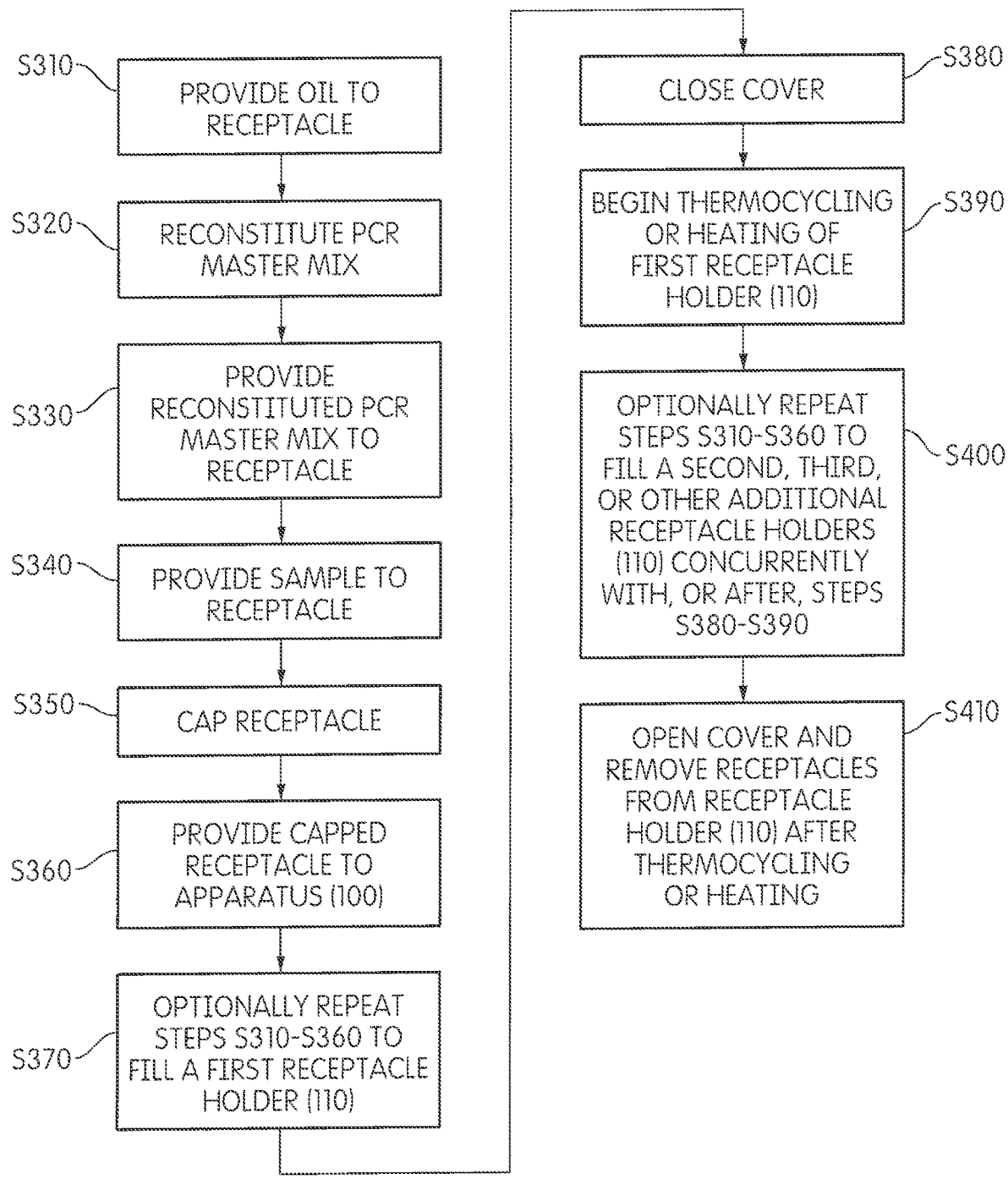
FIG. 13 is a flow chart showing exemplary steps involved in a method of conducting automated, random-access temperature cycling processes.

Use of the apparatus described herein is envisioned as, but is not limited to, being part of an automated process for performing a biochemical assay, such as nucleic acid amplification. Thus, in another aspect, there is provided a method of conducting automated, random-access temperature cycling processes (see FIG. 13). A reaction mixture is prepared by first providing oil to a first receptacle 130 or first set of receptacles (step S310), reconstituting a PCR master mix (step S320) and providing the reconstituted PCR master mix to the receptacle 130 (step S330). The sample to be assayed is thereafter inserted into the receptacle 130 containing the PCR master mix (step S340), thereby forming a reaction mixture 140, and the receptacle 130 is capped (step S350). The first receptacle 130 or first set of receptacles, each containing a reaction mixture 140 is transferred by a receptacle transport mechanism 700 to a first receptacle holder 110 of the apparatus 100 (step S360). The steps of preparing a reaction mixture may optionally be repeated to fill a particular receptacle holder 110 and/or a particular row (step S370).

If a cover 350 and/or stripper plate 650 associated with the particular receptacle holder 110 is present and in the closed and/or locked position, the cover and/or stripper plate is moved to the opened and/or unlocked position to receive the first receptacle 130 or first set of receptacles. Alternatively, if the apparatus includes an alternative embodiment of the cover 824, the receptacle transport mechanism 700, a didi (i.e., end of a pipettor), or a modified pipettor 900, may depress a cover releasing mechanism 852, thereby causing the cover 822 to be moved to the opened position. Yet in another alternative embodiment, if no cover is present, then any step involving movement of the cover is unnecessary and therefore may be omitted. Once the cover 350 and/or stripper plate 650 associated with the receptacle holder 110 is in the opened and/or unlocked position, the receptacle transport mechanism 700 places the first receptacle 130 or first set of receptacles into one or more receptacle wells 120 of the first receptacle holder 110 (step S360). Prior to withdrawal of the receptacle transport mechanism 700, if present, the stripper plate 650 is moved into the locked position to prevent removal of the transferred first receptacle 130, or set thereof, from the first receptacle holder 110 (not shown). In alternative embodiments the receptacle transport mechanism 700 is provided with a mechanism to remove receptacles without utilizing a stripper plate (see, e.g., U.S. Pub. No. 2010/0179687; U.S. Pub. No. 2005/0244303; U.S. Pat. Nos. 6,869,571; 6,824,024; and 6,431,015), thus rendering the use of a stripper plate 650 or equivalent mechanism on the apparatus optional. The transferred receptacle 130 or set thereof may then be released from the receptacle transport mechanism 700 upon contact with the stripper plate 650 as the receptacle transport mechanism 700 withdraws therefrom. After the area surrounding the first receptacle holder is clear of the receptacle transport mechanism, the cover 350 is moved into the closed position (step S380). If the alternative embodiment of the cover mechanism 824 is present in the apparatus, the receptacle transport mechanism 700, the didi, or the modified pipettor 900 depresses a cover securing mechanism 854, thereby causing the cover 822 to be moved to the closed position. As discussed above, once in the closed position, the cover may exert a force F2 onto at least a portion of the receptacle 130 or a set of receptacles. However, in certain embodiments, the cover does not exert force F2 onto the receptacle 130.

As used herein, a "set" of receptacles refers to one or more receptacle(s) 130 held within a receptacle holder 110. For example, a "set" of receptacles 130 refers to the number of receptacles 130 required to at least partially, or to completely, fill a particular receptacle holder 110. Thus, a set of receptacles 130 may refer to a single receptacle 130 being processed by the apparatus 100, or it may refer to any whole number of receptacles 130 up to and including the maximum number of receptacle wells 120 within a particular receptacle holder 110.

The first receptacle holder 110 is then subjected to a first incubation process (step S390), which includes applying a voltage to a first thermal element 200 of the apparatus 100 to alter the temperature of the first receptacle holder 110. By altering the temperature or temperatures of the first receptacle holder 110, the first set of receptacles 130 within the first receptacle holder 110, including the reaction mixture(s) 140 contained in each receptacle 130, is brought to a predetermined temperature and optionally sustained at the temperature for a predetermined time.

During the first incubation process, a second set of receptacles 130, each containing a reaction mixture 140, is optionally transferred by the receptacle transport mechanism 700 to a second receptacle holder 110 of the apparatus 100 (step S400). As with the first set of receptacles, if a cover 350 and/or stripper plate 650 associated with the second receptacle holder 110 is present and in the closed and/or locked position, the cover and/or stripper plate is moved to the opened position and/or unlocked position to receive the second set of receptacles. Once the cover 350 and/or stripper plate 650 associated with the second receptacle holder 110 is in the open position and/or unlocked position, the receptacle transport mechanism 700 places the second set of receptacles into the receptacle wells 120 of the second receptacle holder 110. If a stripper plate 650 is utilized, prior to withdrawal of the receptacle transport mechanism 700, the stripper plate 650 is moved into the locked position to prevent removal of the transferred second set of receptacles from the second receptacle holder 110. The transferred second set of receptacles 130 may then be released from the receptacle transport mechanism 700 upon contact with the stripper plate 650 as the receptacle transport mechanism 700 withdraws therefrom. When the area surrounding the second receptacle holder 110 is clear of the receptacle transport mechanism 700, the cover 350 associated therewith is moved into the closed position. As discussed above, once in the closed position, the cover 350 exerts a force F2 onto at least a portion of the respective set of receptacles.

The second receptacle holder 110 is then subject to a second incubation process, which may be the same as or different—in terms of temperature and duration thereof—than the first incubation process. It should be understood that the first and second incubation processes may occur simultaneously or subsequent to one another. It should be further understood that a third or higher (i.e., third, fourth, fifth, sixth, seventh, eighth, ninth, tenth, eleventh, twelfth, or higher) set of receptacles 130 may be transferred to the apparatus 100, which may thereafter, subject the third or higher set of receptacles 130 to a third or higher (i.e., third, fourth, fifth, sixth, seventh, eighth, ninth, tenth, eleventh, twelfth, or higher) incubation process. Such additional sets of receptacles 130 may be transferred and/or subject to the additional incubation processes either simultaneously or sequentially, as necessary. The transfer of each subsequent set of receptacles 130 may be begun prior to completion of the incubation process for each immediately preceding set of receptacles 130.

In one exemplary embodiment, the first set of receptacles 130 is removed (step S410 of FIG. 13) from the first receptacle holder 110 immediately following placement of the last of the second, or subsequent, set of receptacles 130 within the second receptacle holder 110. In a related exemplary embodiment, the second set of receptacles 130 is removed from the second receptacle holder 110 immediately following placement of the last of the third, or subsequent, set of receptacles 130 within the second receptacle holder 110, and so forth. It will be appreciated by those of skill in the art that the terms "first," "second," "third," and higher terms are relative terms, and are therefore not limited to the positioning or orientation of the receptacle holders 110 within the apparatus 100. Similarly, it will be appreciated by those of skill in the art that the terms "first," "second," "third," and higher terms are not limited to the timing of the incubation process relative to the timing that the apparatus 100 is set up. These terms are merely intended to be relative to the timing of placement and incubation of any particular set of receptacles 130 within each respective receptacle holder 110. For example, the $50^{th}$ set of receptacles may be considered to be the first set of receptacles relative to the $51^{st}$ set of receptacles.

Use of the second exemplary embodiment of the apparatus 800 described herein, like the first exemplary apparatus, is also envisioned as, but is not limited to, being part of an automated process for performing a biochemical assay, such as nucleic acid amplification. As above, if no cover, primary cover, or secondary cover is present, then any step involving movement of the covers is unnecessary and therefore may be omitted. As above, a reaction mixture is prepared by first providing oil to a first receptacle 130 or first set of receptacles (step S310), reconstituting a PCR master mix (step S320) and providing the reconstituted PCR master mix to the receptacle 130 (step S330). The sample to be assayed is thereafter inserted into the receptacle 130 containing the PCR master mix (step S340), thereby forming a reaction mixture 140, and the receptacle 130 is capped (step S350). The first receptacle 130 or first set of receptacles, each containing a reaction mixture 140 is transferred by a receptacle transport mechanism 700 to a first receptacle holder 110 of the apparatus 100 (step S360). The steps of preparing a reaction mixture may optionally be repeated to fill a particular receptacle holder 110 and/or a particular row (step S370). Transferring of the first receptacle 130 or first set of receptacles is accomplished by first performing an automated motion of moving the plunger 910 of a modified pipettor 900 into the raised position (as shown in FIG. 15A), thereby causing the knob 912 to slidingly contact the one or more limbs 915 and move the limbs 915 into a retracted position such that a lower portions 917 thereof are placed in close proximity to the body 920 of the pipettor 900. The pipettor 900, having a capped first receptacle 130 or first set of receptacles frictionally attached thereto, places the first receptacle 130 or first set of receptacles into one or more receptacle wells 120 of the first receptacle holders 110 (step S360). As the first receptacle 130 or first set of receptacles is lowered into the receptacle well 120, the first receptacle 130 or first set of receptacles contacts at least a portion of the securing arms 845 of the primary cover 840. The downward force applied by receptacle to the securing arms 845 cause the securing arms 845 to flex in a radial outward direction in relation to the axial center of the receptacle well 120 such that the lower portion of the cap clears the securing arms 845. Once the lower portion of the cap 135 clears the securing arms 845, the securing arms return to their rest position, thereby securably contacting at least a portion of the cap 135, ensuring that the capped receptacle fits snugly within the receptacle well 120, thereby allowing maximal contact between the inner surface 180 of the receptacle well 120 and the receptacle 130.

The first receptacle holder 110 is then subjected to a first incubation process (step S390), which includes applying a voltage to a first thermal element 200 of the apparatus 100 to alter the temperature of the first receptacle holder 110. By altering the temperature or temperatures of the first receptacle holder 110, the first set of receptacles 130 within the first receptacle holder 110, including the reaction mixture(s) 140 contained in each receptacle 130, is brought to a predetermined temperature and optionally sustained at the temperature for a predetermined time or fluctuated between a series of temperatures.

As above, during the first incubation process, a second set of receptacles 130, each containing a reaction mixture 140, is optionally transferred by the receptacle transport mechanism 700 to a second receptacle holder 110 of the apparatus 100 (step S400).

Upon completion of the incubation process, removal of the first receptacle 130 or set of receptacles from the second exemplary embodiment of the apparatus 800 is accomplished by performing an automated motion of moving the plunger 910 of a modified pipettor 900 into the lowered position (as shown in FIG. 15B), thereby causing the knob 912 to slidingly contact the one or more limbs 915 and move the limbs 915 into an extended position such that a lower portions 917 thereof are moved away from the body 920. Thereafter, the modified pipettor 900 is lowered into the open end of the cap 135 of the first receptacle 130 or set of receptacles. As shown in FIG. 15C, upon lowering of the modified pipettor 900, the extended lower portions 917 of the limbs 915 contact the actuators 860 of the secondary cover 850 and apply a downward force thereto. The downward force causes the releasing arms 856 to slidingly contact the securing arms 845 of the primary cover 840, causing the securing arms 845 to flex in a radial outward direction relative to the axial center of the receptacle well 120, as the modified pipettor 900 frictionally engages the open end of the cap 135. The flexing of the securing arms 845 releases the capped receptacle 130/135 or set of receptacles, allowing the capped receptacle to be removed from the receptacle well 120 as the modified pipettor 900 is raised therefrom.

In certain embodiments, it is desirable to preheat the heat sink 330 of the apparatus 100 prior to or during the incubation process. In those embodiments, prior to, during, or after the first receptacle 130 or first set of receptacles, each containing a reaction mixture 140 is transferred by a receptacle transport mechanism 700 to a first receptacle holder 110 of the apparatus 100, a voltage is applied to a thermal element 334 that is in thermal communication with the heat sink 330. As discussed above, the heat sink may be warmed to about 45-50° C., for example, prior to the biochemical assay. The transferred receptacle 130 or set thereof may then be released from the receptacle transport mechanism 700 upon contact with the stripper plate 650 as the receptacle transport mechanism 700 withdraws therefrom. After the area surrounding the first receptacle holder is clear of the receptacle transport mechanism, the cover 350 is moved into the closed position. As discussed above, once in the closed position, the cover exerts a force F2 onto at least a portion of the receptacle 130 or a set of receptacles. Thereafter, the first receptacle holder 110 is then subjected to a first incubation process, which includes applying a voltage to a first thermal element 200 of the apparatus 100 to alter the temperature of the first receptacle holder 110. By altering the temperature or temperatures of the first receptacle holder 110, the first set of receptacles 130 within the first receptacle holder 110, including the reaction mixture(s) 140 contained in each receptacle 130, is brought to a predetermined temperature and optionally sustained at the temperature for a predetermined time.

In various embodiments, the temperature of the receptacle holder 110 will be above ambient temperature as a result of a prior incubation process performed on a previous receptacle 130 or set thereof, or due to pre-heating of the heat sink 330. In these embodiments, pre-heating or additional heating of the heat sink 330 may or may not be desired due to a lessened risk of heat sap, as discussed above.

Each of the first and second sets of receptacles 130 (and/or any additional sets of receptacles) may be transferred to the apparatus 100 by a single receptacle transport mechanism 700 or may be transferred by more than one receptacle transport mechanism 700, depending on the configuration of the apparatus 100, system, or biochemical instrument.

Each set of receptacles 130 may undergo a single incubation process or a plurality of incubation processes prior to completion of the biochemical assay. Alternatively, or in conjunction, each set of receptacles 130 may undergo a single temperature ramp for purposes of, for example, a melt curve analysis. If a set of receptacles 130 undergoes multiple temperature cycles, each subsequent temperature cycle may be the same as or different from the temperature cycle immediately preceding it. During the single or plurality of incubation processes, during the temperature ramp, or upon completion of a predetermined number of incubation processes, an excitation signal source 500 transmits an excitation signal via optical fibers 400 of the apparatus 100 to the set of receptacles 130. Any emission signals resulting therefrom are thereafter transmitted via the optical fibers 400 to one or more emission signal detectors 510. Though FIG. 10 depicts separate optical fibers branching out to the excitation signal source 500 and emission signal detector 510, various embodiments of the present disclosure utilize a single optical fiber (i.e., a light pipe) between the excitation signal source 500 and its corresponding emission signal detector 510. One of skill in the art will appreciate that a collection of mirrors, dichroics, and/or filters can be utilized to split the excitation and emission signals travelling through the single optical fiber between the excitation signal source 500 and its corresponding emission signal detector 510. In these embodiments, one end of the single optical fiber terminates in or at a single receptacle well, and the other end of the single optical fiber terminates at location in optical communication with the excitation signal source 500 and its corresponding emission signal detector 510. Often, in such a configuration, every receptacle well in the apparatus will be outfitted with a similar optical fiber arrangement.

Following completion of all incubation processes and/or detection steps, the respective set of receptacles 130 is removed from the respective receptacle holder 110 of the apparatus 100. Removal of a set of receptacles 130 often proceeds as follows. The cover 350, if present, that is associated with the receptacle holder 110 in which the assayed receptacles 130 are seated is moved to the opened position. Either simultaneously or shortly thereafter, the stripper plate 650, if present and in the locked position, is moved to the unlocked position. The receptacle transport mechanism 700 is moved into position and lowered toward the receptacle holder 110 to contact the tops of each of the receptacles 130 seated therein. In frequent embodiments, the receptacle transport mechanism 700 contacts a single receptacle 130 at any particular time. In certain embodiments the receptacle transport mechanism 700 is capable of contacting and removing a set of receptacles 130. Upon withdrawal of the receptacle transport mechanism 700, any receptacles contacted therewith are removed from the receptacle holder 110. It should be understood that assayed receptacles 130 or sets thereof, may be removed prior to, during, or after completion of the temperature cycling process of any previous or subsequent sets of receptacles.

Thus, a first set of receptacles may be removed from the first receptacle holder 110 prior to completion of the second incubation process of the second set of receptacles 130 within the second receptacle holder 110. Likewise, a second set of receptacles 130 may be removed from the second receptacle holder 110 prior to completion of a third or higher incubation process of a third or higher set of receptacles 130 within the third or higher receptacle holder 110.

Because the present apparatus 100, 800 is capable of simultaneously conducting a variety of different assays, it is also envisioned that due to the requirements of a particular assay, sample, reagents, or any other reason, a second set of receptacles 130 may be subjected to a shorter incubation process than a first set of receptacles 130 such that the second or subsequent set of receptacles may be removed prior to removal of the first set of receptacles.

Accordingly, the apparatus 100, 800 described herein provides the ability to automate incubation processes, simultaneously involving the same or different biochemical assays. In an exemplary embodiment, the apparatus includes six rows (101-106) of receptacle holders 110 with two receptacle holders 110 per row and five receptacle wells 120 per receptacle holder 110. As such, the apparatus of the exemplary embodiment is capable of simultaneously incubating up to sixty receptacles 130 at any given time. Assuming an incubation time of sixty minutes for each set of receptacles 130 within each receptacle holder, and population of each receptacle holder 110 (containing five receptacle wells 120) with a set of receptacles 130 every five minutes, the first set of receptacles will complete the incubation, about sixty five minutes after the first receptacle 130 is placed in a receptacle well 120. Thereafter, every five minutes another set of five receptacles will complete its incubation period. When each set of receptacles has completed its incubation, the set is removed from the receptacle holder and replaced with a fresh set of receptacles for another incubation period. Thus, when an apparatus 100, 800 is used in conjunction with an automated instrument for performing a biochemical assay, such as PCR, the apparatus increases instrument throughput productivity within a typical 8-hour shift.

System for Automated Random-Access Incubation

In another aspect, the present disclosure provides a system for automated random-access incubation for nucleic acid amplification assays. The system includes one or more of the apparatus 100, 800 and allows for simultaneous or individualized assays to be performed. The system includes a housing 50 into which the one or more apparatuses 100, 800 are located. As discussed above, the thermal element 200 corresponding to each receptacle holder 110 may be independently controllable to only alter the temperature of its corresponding receptacle holder 110. Thus, the system may include more than one controller 220, each of which is electrically connected to a single thermal element 200 and one or more thermistors 610 of an individual receptacle holder 110, and/or connected to a controllable power source 212 connected to a motor 355 effecting movement to a cover 350, if present, and/or a motor 660 effecting movement of a stripper plate 650, if present, of the individual receptacle holder 110. It should be understood that any one or more controllers (220, 370, 670) may be combined to effect independent control of more than one thermal element 200 and/or controllable power source 212 connected to an electric motor (355, 660). Thus, the system may include a single controller electrically connected to each of the thermal elements 200 and to one or more motors 355 disposed in moveable communication with the cover 350 and/or stripper plate 650 corresponding to each receptacle holder 110. Likewise, the system may include an appropriately programmed processor 750 (such as a computer) which is electrically connected to each controller (220, 370, 670) to send and/or receive signals/commands for performing an incubation process. In certain embodiments, the controller (220, 370, 670) and the processor 750 will be configured in the same unit, thereby reducing the number of components within the system.

As discussed above, the system will include at least one heat sink 330. Thus, each of the one or more apparatuses 100, 800 within the system may be disposed in independent thermal communication with a single heat sink 330 (i.e., one heat sink per apparatus), or every apparatus 100, 800 may be in thermal communication with a single heat sink 330. In certain embodiments, each receptacle holder 110 of each apparatus 100, 800 of the system will be disposed in independent thermal communication with a dedicated heat sink 330 (i.e., one heat sink per receptacle holder), as discussed above.

As shown in FIG. 10, the system may further include one or more excitation signal sources 500 and one or more emission signal detectors 510 to which the second ends 430 of the optical fibers 400 of the apparatus 100, 800 included therein are in optical communication. Excitation signal sources 500 and emission signal detectors 510 contemplated by the present disclosure include, but are not limited to, fluorometers, luminometers, spectrophotometers, infrared detectors and charged-coupled devices. Each of these types of optical detection systems can be positioned within the housing of the apparatus 100, 800, within the housing of the system, or within the overall housing of the biochemical analysis instrument, as appropriate. Multiple types of signal sources 500 and signal detectors 510 may be movably mounted on a platform to facilitate different detection methods for different processes. The system may also include multiple detectors of the same or different types for detecting signals emitted from different receptacles 130 simultaneously. As discussed above, though FIG. 10 depicts separate optical fibers branching out to the excitation signal source 500 and emission signal detector 510, certain embodiments of the present disclosure utilize a single optical fiber (e.g., a light pipe) between the excitation signal source 500 and its corresponding emission signal detector 510.

The system may further include a receptacle transport mechanism 700 (e.g., a pick-and-place mechanism, a pipettor, or a modified pipettor) that is positioned within the housing of the system or within the overall housing of the instrument. The receptacle transport mechanism 700 is configured to transfer and/or remove one or more receptacles 130, either individually or as a set, from a receptacle holder 110 of the apparatus 100. In various embodiments, the modified pipettor 900 includes a body having a plunger slidingly disposed therein, and one or more limbs hingedly attached to the body and positioned in sliding communication with a knob fixedly attached to the plunger. When the plunger is in a first position, a lower portion of the one or more limbs are proximal to the body, and when the plunger is in a second position, the lower portion of the one or more limbs are extended in a radial outward direction relative to the body. In certain embodiments, the receptacle transport mechanism 700 is configured to additionally dispense into and/or remove liquids from individual receptacles 130.

Although the present disclosure has been described with reference to the above example, it will be understood that modifications and variations are encompassed within the spirit and scope of the disclosed subject matter. Accordingly, the present disclosure is limited only by the following claims.

What is claimed is:

1. An apparatus for performing nucleic acid amplification reactions, the apparatus comprising:
    a thermally-conductive receptacle holder, the receptacle holder comprising a plurality of receptacle wells, each of the receptacle wells being configured to receive a receptacle, and each of the receptacle wells having a through-hole extending from an inner surface of the receptacle well to an outer surface of the receptacle holder;
    a cover movable between an open position and a closed position relative to the receptacle holder, the cover being configured to seat or secure receptacles disposed within the receptacle wells when the cover moves from the open position to the closed position; and
    a plurality of optical fibers, each of the optical fibers having a first end and a second end, the first end of each optical fiber being in optical communication with an associated one of the receptacle wells, and the second end of each optical fiber being in optical communication with at least one of an excitation signal source and an emission signal detector, wherein the first end of each of the optical fibers extends through the through-hole of the associated receptacle well and into the associated receptacle well when a receptacle is not present in the associated receptacle well and the cover is in the closed position, and wherein the first end of each of the optical fibers contacts a receptacle disposed in the associated receptacle well when the cover is in the closed position.

2. The apparatus of claim 1, wherein the through-hole of each of the receptacle wells is positioned at a bottom-center of the receptacle well.

3. The apparatus of claim 1, wherein the receptacle wells support one or more receptacles containing a reaction mixture, and wherein each of the receptacles is closed with a cap, the cap being situated above a top surface of the receptacle holder.

4. The apparatus of claim 3, wherein each of the receptacles is a single unit.

5. The apparatus of claim 1, wherein each of the optical fibers is in optical communication with the excitation signal source and the emission signal detector.

6. The apparatus of claim 1, wherein the cover is affixed to a rigid rotatable member in movable communication with an electric motor.

7. The apparatus of claim 6, wherein the rotatable member comprises a cylindrical rod having a circular cross-section and an axis of rotation at the center thereof.

8. The apparatus of claim 6, wherein the cover comprises a plurality of flexible extensions attached to and extending laterally away from the rotatable member.

9. The apparatus of claim 8, wherein each of the flexible extensions is configured to contact a receptacle in a corresponding one of the receptacle wells as the cover is rotated from the open position to the closed position, such that each of the flexible extensions contacts at least a portion of the receptacle in the corresponding receptacle well.

10. The apparatus of claim 9, wherein each of the flexible extensions is configured to apply a force to at least a portion of the receptacle in the corresponding receptacle well when the cover is in the closed position, thereby seating or securing the receptacle in the corresponding receptacle well.

11. The apparatus of claim 1, further comprising:
    a thermally-conductive support; and
    a thermal element positioned between the support and the receptacle holder.

12. The apparatus of claim 11, wherein the thermal element is electrically connected to a controllable power source for applying a current across the thermal element, to thereby alter the temperature of the receptacle holder.

13. The apparatus of claim 11, wherein:
    the support comprises a base portion and an upright portion, the base portion having a plurality of through-holes, wherein each of the through-holes of the base portion is in alignment with a corresponding one of the through-holes of the receptacle holder; and
    the thermal element is positioned between a side surface of the upright portion and an opposed side surface of the receptacle holder.

14. The apparatus of claim 13, wherein each of the through-holes of the base portion of the support forms a channel supporting a fixed or moveable ferrule and through which a corresponding one of the optical fibers passes.

15. The apparatus of claim 14, further comprising a spring biased against each ferrule and wherein each ferrule is movably supported in the channel so that the spring urges the first end of the corresponding optical fiber into the associated receptacle well.

16. The apparatus of claim 13, further comprising a heat sink in thermal communication with the support.

17. The apparatus of claim 16, wherein the base portion of the support is disposed on a top surface of the heat sink, and wherein the heat sink comprises a plurality of through-holes, each of the through-holes of the heat sink being in alignment with one of the through-holes of the receptacle holder, and wherein each of the optical fibers passes through a corresponding one of the through-holes of the heat sink.

18. The apparatus of claim 1, further comprising a spring coupled to the first end of each optical fiber and configured to urge the first end of the optical fiber into the associated receptacle well.

19. The apparatus of claim 1, wherein the first end of each of the optical fibers is moveable with respect to the through-hole relative to the inner surface of the associated receptacle well, and wherein movement of the first end of each of the optical fibers with respect to the through-hole of the associated receptacle well is caused by movement of the cover to the open position or by movement of the cover to the closed position.

20. A system for performing nucleic acid amplification reactions, the system comprising:
    the apparatus of claim 1; and
    a receptacle transport mechanism for transferring receptacles to and from the receptacle wells.

21. The system of claim 20, wherein the receptacle transport mechanism is a pipettor.

22. The system of claim 20 further comprising a stripper plate mounted in moveable association with the receptacle holder, the stripper plate being moveable between an unlocked position and a locked position, wherein a receptacle can be transferred to or removed from any one of the receptacle wells when the stripper plate is in the unlocked position, and wherein a receptacle disposed in any one of the receptacle wells is inhibited from removal when the stripper plate is in the locked position.

23. The system of claim 22, wherein the stripper plate is configured to move to the locked position after one or more receptacles have been transferred to one or more of the receptacle wells by the receptacle transport mechanism and before the receptacle transport mechanism is withdrawn from the one or more receptacle wells.

24. The apparatus of claim 1, wherein movement of the first end of each of the optical fibers with respect to the through-hole of the associated receptacle well is caused by movement of the cover into contact with the receptacle within the associated receptacle well or by movement of the cover out of contact with the receptacle within the associated receptacle well.

\* \* \* \* \*